(12) United States Patent
Chen et al.

(10) Patent No.: US 7,507,794 B2
(45) Date of Patent: Mar. 24, 2009

(54) ISOLATED SOLUBLE CORTICOTROPIN RELEASING FACTOR RECEPTOR TYPE 2 (SCRFR2)

(75) Inventors: Alon Chen, Rehovot (IL); Marilyn Perrin, La Jolla, CA (US); Wylie Vale, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 2 days.

(21) Appl. No.: 11/350,411

(22) Filed: Feb. 8, 2006

(65) Prior Publication Data
US 2007/0042954 A1 Feb. 22, 2007

Related U.S. Application Data

(60) Provisional application No. 60/650,866, filed on Feb. 8, 2005.

(51) Int. Cl.
C07K 1/00 (2006.01)
C07K 14/00 (2006.01)
C07K 17/00 (2006.01)
A01N 37/18 (2006.01)
A61K 38/00 (2006.01)

(52) U.S. Cl. .......................................... 530/350; 514/2
(58) Field of Classification Search ................. None
See application file for complete search history.

(56) References Cited

U.S. PATENT DOCUMENTS

| 5,063,245 | A | 11/1991 | Abreu et al. | ................. | 514/404 |
| 5,225,538 | A | 7/1993 | Capon et al. | ............. | 530/387.3 |
| 5,786,203 | A * | 7/1998 | Lovenberg et al. | ........ | 435/252.3 |
| 6,831,158 | B2 | 12/2004 | Nissen et al. | ............... | 530/397 |

FOREIGN PATENT DOCUMENTS

WO WO 2006/031322 3/2006

OTHER PUBLICATIONS

Chen et al., "A soluble mouse brain splice variant of type 2alpha corticotropin-releasing factor (CRF) receptor binds ligands and modulates their activity," Proc. Natl. Acad. Sci. USA, 102:2620-2625, 2005.
Grace et al., "NMR structure and peptide hormone binding site of the first extracellular domain of a type B1 G protein-coupled receptor," Proc. Natl. Acad. Sci. USA, 101:12836-12841, 2004.
Liaw et al., "Cloning and Characterization of the Human Corticotropin-Releasing Factor-2 Receptor Complementary Deoxyribonucleic Acid," Endocrinol., 137:72-77, 1996.
Liaw et al., "Localization of agonist- and antagonist-binding domains of human corticotropin-releasing factor receptors," Mol. Endocrinol., 11:2048-2053, 1997.
Perrin et al., "A soluble form of the first extracellular domain of mouse type 2beta corticotropin-releasing factor receptor reveals differential ligand specificity," J. Biol. Chem., 278:15595-15600, 2003.
Perrin et al., "Expression, purification, and characterization of a soluble form of the first extracellular domain of the human type 1 corticotropin releasing factor receptor," J. Biol. Chem., 276:31528-31534, 2001.
Bale and Vale, "CRF and CRF receptors: Role in stress responsivity and other behaviors," Annu. Rev. Pharmacol. Toxicol., 44:525-557, 2004.
Bale et al., "Mice deficient for corticotropin-releasing hormone receptor-2 display anxiety-like behaviour and are hypersensitive to stress," Nat. Genet., 24:410-414, 2000.
Baud et al., "EMR1, an unusual member in the family of hormone receptors with seven transmembrane segments," Genomics, 26:334-344, 1995.
Brar et al., In: Encyclopedia of Hormones & Related Cell Regulators, Henry (Ed.), AN (Academic Press), 3:13-325. 2002.
Chalmers et al., "Corticotrophin-releasing factor receptors: from molecular biology to drug design," Trends Pharmoacol. Sci., 17:166-172, 1996.
Chang et al., "Identification of a seven transmembrane helix receptor for corticotropin-releasing factor and sauvagine in mammalian brain," Neuron., 11:1187-1195, 1993.
Chen et al., "Mouse corticotropin-releasing factor receptor type 2α gene: Isolation, distribution, pharmacological characterization and regulation by stress and glucocorticoids," Mol. Endocrinol., 19:441-458, 2005.
Chen et al., "Expression cloning of a human corticotropin-releasing-factor receptor," Proc. Natl. Acad. Sci. USA, 90:8967-8971, 1993.
Dautzenberg et al., "N-Terminal splice variants of the Type I PACAP receptor: Isolation, characterization and ligand binding/selectivity determinants," J. Neuroendocrinol., 11:941-949, 1999.
Eason et al., "Evaluation of recombinant human soluble dimeric tumor necrosis factor receptor for prevention of OKT3-associated acute clinical syndrome," Transplantation, 61:224-228, 1996.
Grammatopoulos et al., "A novel spliced variant of the type 1 corticotropin-releasing hormone receptor with a deletion in the seventh transmembrane domain present in the human pregnant term myometrium and fetal membranes," Mol. Endocrinol., 13:2189-2202, 1999.
Graves et al., "Cloning and sequencing of a 1.3 KB variant of human thyrotropin receptor mRNA lacking the transmembrane domain," Biochem. Biophys. Res. Commun., 187:1135-1143, 1992.

(Continued)

Primary Examiner—Robert Landsman
(74) Attorney, Agent, or Firm—Fulbright & Jaworski L.L.P.

(57) ABSTRACT

The present invention is directed to compositions and methods related to soluble G-protein coupled receptors (sGPCR). In ceratin aspects the invention includes compositions and methods related to a soluble corticotropin releasing factor receptor related protein, sCRFR2, as well as its effects on CRFR signaling and interaction between CRF family ligand and CRFR receptors, including but not limited to CRFR2, CRFR1 and functional or signaling capable variants thereof.

22 Claims, 5 Drawing Sheets

OTHER PUBLICATIONS

Hamann et al., "Expression cloning and chromosomal mapping of the leukocyte activation antigen CD97, a new seven-span transmembrane molecule of the secretion receptor superfamily with an unusual extracellular domain," *J. Immunol.*, 155:1942-1950, 1995.

Hsu and Hsueh, "Human stresscopin and stresscopin-related peptide are selective ligands for the type 2 corticotropin-releasing hormone receptor," *Nat. Med.*, 7:605-7611, 2001.

Jacobson et al., "Impact of potent antiretroviral therapy on the incidence of Kaposi's sarcoma and non-Hodgkin's lymphomas among HIV-1-infected individuals," *J. Acquir. Immune. Defic. Syndr.*, 21:S34-41, 1999.

Ji et al., "Selective inhibition by kringle 5 of human plasminogen on endothelial cell migration, an important process in angiogenesis," *Biochem. Biophys. Res. Commun.*, 247:414-419, 1998.

Kehne and Lombaert, "Non-peptidic CRF1 receptor antagonists for the treatment of anxiety, depression and stress disorders," *Curr. Drug Targets CNS Neurol. Disord.*, 1:467-493, 2002.

Kenakin, "Are receptors promiscuous? Intrinsic efficacy as a transduction phenomenon," *Life Sci.*, 43:1095-1101, 1998.

Khan et al., "Cloning of alternately spliced mRNA transcripts coding for variants of ovine testicular follitropin receptor lacking the G protein coupling domains," *Biochem. Biophys. Res. Commun.*, 190:888-894, 1993.

Kishimoto et al., " A sauvagine/corticotropin-releasing factor receptor expressed in heart and skeletal muscle," *Proc Natl. Acad. Sci. USA*, 92:1108-1112, 1995.

Koob and Heinrichs, "A role for corticotropin releasing factor and urocortin in behavioral responses to stressors," *Brain Res.*, 848:141-152, 1999.

Kostich et al., "Molecular identification and analysis of a novel human corticotropin-releasing factor (CRF) receptor: the CRF2gamma receptor," *Mol. Endocrinol.*, 12:1077-1085, 1998.

Lewis et al., "Identification of urocortin III, an additional member of the corticotropin-releasing factor (CRF) family with high affinity for the CRF2 receptor," *Proc. Natl. Acad. Sci. USA*, 98:7570-7575, 2001.

Liu et al., "On the origin of mRNA encoding the truncated dopamine D3-type receptor D3nf and detection of D3nf-like immunoreactivity in human brain," *J. Biol. Chem.*, 269:29220-29226, 1994.

Lovenberg et al., "Cloning and characterization of a functionally distinct corticotropin-releasing factor receptor subtype from rat brain," *Proc. Natl. Sci. USA*, 92:836-840, 1995.

Lovenberg et al., "CRF2 alpha and CRF2 beta receptor mRNAs are differentially distributed between the rat central nervous system and peripheral tissues," *Endocrinology*, 136:4139-4142, 1995.

Malherbe et al., "Cloning and functional expression of alternative spliced variants of the human metabotropic glutamate receptor 8," *Brain Res. Mol. Brain Res.*, 67:201-210, 1999.

Mannstadt et al., "Receptors for PTH and PTHrP: their biological importance and functional properties," *Am. J. Physiol.*, 277:F665-675, 1999.

Marchese et al., "Novel GPCRs and their endogenous ligands: expanding the boundaries of physiology and pharmacology," *Trends Pharmacol Sci.*, 20:370-375, 1999.

Meij et al., "Regulation of G protein function: implications for heart disease," *Mol. Cell Biochem.*, 157:31-38, 1996.

Muglia et al., "Corticotropin-releasing hormone deficiency reveals major fetal but not adult glucocorticoid need," *Nature*, 373:427-432, 1995.

Murphy et al., "Vaccine protection against simian immunodeficiency virus by recombinant strains of herpes simplex virus," *J. Virol.*, 74:7745-7754, 2000.

Owens et al., "The effects of alprazolam on corticotropin-releasing factor neurons in the rat brain: acute time course, chronic treatment and abrupt withdrawal," *J. Pharmacol. Exp. Ther.*, 258:349-356, 1991.

Palczewski et al., "Crystal structure of rhodopsin: A G protein-coupled receptor," *Science*, 289:739-745, 2000.

Perrin and Vale, "Corticotropin releasing factor receptors and their ligand family," *Ann. N.Y. Acad. Sci.*, 885:312-328, 1999.

Perrin et al., "Identification of a second corticotropin-releasing factor receptor gene and characterization of a cDNA expressed in heart," *Proc. Natl. Acad. Sci. USA*, 92:2969-2973, 1995.

Perrin et al., "Identification of a second corticotropin-releasing factor receptor gene and characterization of a cDNA expressed in heart," *J. Biol. Chem.*, 276:31528-31534, 2001.

Pisarchik and Slominski, "Molecular and functional characterization of novel CRFR1 isoforms from the skin," *Eur. J. Biochem.*, 271:2821-2830, 2004.

Rekaski et al., "Isolation and sequencing of cDNAs for splice variants of growth hormone-releasing hormone receptors from human cancers," *Proc. Natl. Acad. Sci. USA*, 97:10561-10566, 2000.

Reyes et al., "Urocortin II: a member of the corticotropin-releasing factor (CRF) neuropeptide family that is selectively bound by type 2 CRF receptors," *Proc. Natl. Acad. Sci. USA*, 98:2843-2848, 2001.

Rivier and Vale, "Modulation of stress-induced ACTH release by corticotropin-releasing factor, catecholamines and vasopressin ," *Nature*, 305:325-327, 1983.

Schwarz et al., "Characterization of gamma-aminobutyric acid receptor GABAB(1e), a GABAB(1) splice variant encoding a truncated receptor," *J. Biol. Chem.*, 275:32174-32181, 2000.

Seck et al., "The alternatively spliced deltae13 transcript of the rabbit calcitonin receptor dimerizes with the C1a isoform and inhibits its surface expression," *J. Biol. Chem.*, 278:23085-23093, 2003.

Smith et al., "Corticotropin releasing factor receptor 1-deficient mice display decreased anxiety, impaired stress response, and aberrant neuroendocrine development," *Neuron.*, 20:1093-1102, 1998.

Stenzel et al., "Identification of a novel murine receptor for corticotropin-releasing hormone expressed in the heart," *Mol. Endocrinol.*, 9:637-645, 1995.

Timpl et al., "Impaired stress response and reduced anxiety in mice lacking a functional corticotropin-releasing hormone receptor 1," *Nat. Genet.*, 19:162-166, 1998.

Vale et al., "Characterization of a 41-residue ovine hypothalamic peptide that stimulates secretion of corticotropin and beta-endorphin," *Science*, 213:1394-1397, 1981.

Valerio et al., "Alternative splicing of mGlu6 gene generates a truncated glutamate receptor in rat retina," *Neuroreport*, 12:2711-2715, 2001.

van Dullemen et al., "Treatment of Crohn's disease with anti-tumor necrosis factor chimeric monoclonal antibody (cA2)," *Gastroenterology*, 109:129-135, 1995.

Van Pett et al., "Distribution of mRNAs encoding CRF receptors in brain and pituitary of rat and mouse," *J. Comp. Neurol.*, 428:191-212, 2000.

Vaughan et al., "Urocortin, a mammalian neuropeptide related to fish urotensin I and to corticotropin-releasing factor," *Nature*, 378:287-292, 1995.

Vita et al., "Primary structure and functional expression of mouse pituitary and human brain corticotrophin releasing factor receptors," *FEBS Lett.*, 335:1-5, 1993.

Wilson et al., "Orphan G-protein-coupled receptors: the next generation of drug targets?," *Br. J. Pharmacol.*, 125:1387-1392, 1998.

Wilson et al., In: *G-protein- coupled receptors*, CRC press, Boca Raton, 97-114, 1999.

You et al., "Three different turkey luteinizing hormone receptor (tLH-R) isoforms I: characterization of alternatively spliced tLH-R isoforms and their regulated expression in diverse tissues," *Biol. Reprod.*, 62:108-116, 2000.

Zhu et al., "Cloning of novel splice variants of mouse mGluR1," *Brain Res. Mol. Brain Res.*, 73:93-103, 1999.

\* cited by examiner

SEQUENCE LISTING

```
<160> NUMBER OF SEQ ID NOS: 17

<210> SEQ ID NO 1
<211> LENGTH: 2107
<212> TYPE: DNA
```

<213> ORGANISM: homo sapien
<220> FEATURE:
<221> NAME/KEY: CDS
<222> LOCATION: (1)..(1233)

<400> SEQUENCE: 1

| | | | | | | | | | | | | | | | | |
|---|---|---|---|---|---|---|---|---|---|---|---|---|---|---|---|---|
| atg | gac | gcg | gca | ctg | ctc | cac | agc | ctg | ctg | gag | gcc | aac | tgc | agc | ctg | 48 |
| Met | Asp | Ala | Ala | Leu | Leu | His | Ser | Leu | Leu | Glu | Ala | Asn | Cys | Ser | Leu | |
| 1 | | | | 5 | | | | | 10 | | | | | 15 | | |
| gcg | ctg | gct | gaa | gag | ctg | ctc | ttg | gac | ggc | tgg | ggg | cca | ccc | ctg | gac | 96 |
| Ala | Leu | Ala | Glu | Glu | Leu | Leu | Leu | Asp | Gly | Trp | Gly | Pro | Pro | Leu | Asp | |
| | | | | 20 | | | | | 25 | | | | | 30 | | |
| ccc | gag | ggt | ccc | tac | tcc | tac | tgc | aac | acg | acc | ttg | gac | cag | atc | gga | 144 |
| Pro | Glu | Gly | Pro | Tyr | Ser | Tyr | Cys | Asn | Thr | Thr | Leu | Asp | Gln | Ile | Gly | |
| | | | 35 | | | | | 40 | | | | | 45 | | | |
| acg | tgc | tgg | ccc | cgc | agc | gct | gcc | gga | gcc | ctc | gtg | gag | agg | ccg | tgc | 192 |
| Thr | Cys | Trp | Pro | Arg | Ser | Ala | Ala | Gly | Ala | Leu | Val | Glu | Arg | Pro | Cys | |
| | 50 | | | | | 55 | | | | | 60 | | | | | |
| ccc | gag | tac | ttc | aac | ggc | gtc | aag | tac | aac | acg | acc | cgg | aat | gcc | tat | 240 |
| Pro | Glu | Tyr | Phe | Asn | Gly | Val | Lys | Tyr | Asn | Thr | Thr | Arg | Asn | Ala | Tyr | |
| 65 | | | | | 70 | | | | | 75 | | | | | 80 | |
| cga | gaa | tgc | ttg | gag | aat | ggg | acg | tgg | gcc | tca | aag | atc | aac | tac | tca | 288 |
| Arg | Glu | Cys | Leu | Glu | Asn | Gly | Thr | Trp | Ala | Ser | Lys | Ile | Asn | Tyr | Ser | |
| | | | | 85 | | | | | 90 | | | | | 95 | | |
| cag | tgt | gag | ccc | att | ttg | gat | gac | aag | cag | agg | aag | tat | gac | ctg | cac | 336 |
| Gln | Cys | Glu | Pro | Ile | Leu | Asp | Asp | Lys | Gln | Arg | Lys | Tyr | Asp | Leu | His | |
| | | | 100 | | | | | 105 | | | | | 110 | | | |
| tac | cgc | atc | gcc | ctt | gtc | gtc | aac | tac | ctg | ggc | cac | tgc | gta | tct | gtg | 384 |
| Tyr | Arg | Ile | Ala | Leu | Val | Val | Asn | Tyr | Leu | Gly | His | Cys | Val | Ser | Val | |
| | | | | 115 | | | | | 120 | | | | | 125 | | |
| gca | gcc | ctg | gtg | gcc | gcc | ttc | ctg | ctt | ttc | ctg | gcc | ctg | cgg | agc | att | 432 |
| Ala | Ala | Leu | Val | Ala | Ala | Phe | Leu | Leu | Phe | Leu | Ala | Leu | Arg | Ser | Ile | |
| | | 130 | | | | | 135 | | | | | 140 | | | | |
| cgc | tgt | ctg | cgg | aat | gtg | att | cac | tgg | aac | ctc | atc | acc | acc | ttt | atc | 480 |
| Arg | Cys | Leu | Arg | Asn | Val | Ile | His | Trp | Asn | Leu | Ile | Thr | Thr | Phe | Ile | |
| 145 | | | | | 150 | | | | | 155 | | | | | 160 | |
| ctg | cga | aat | gtc | atg | tgg | ttc | ctg | ctg | cag | ctc | gtt | gac | cat | gaa | gtg | 528 |
| Leu | Arg | Asn | Val | Met | Trp | Phe | Leu | Leu | Gln | Leu | Val | Asp | His | Glu | Val | |
| | | | | 165 | | | | | 170 | | | | | 175 | | |
| cac | gag | agc | aat | gag | gtc | tgg | tgc | cgc | tgc | atc | acc | acc | atc | ttc | aac | 576 |
| His | Glu | Ser | Asn | Glu | Val | Trp | Cys | Arg | Cys | Ile | Thr | Thr | Ile | Phe | Asn | |
| | | | 180 | | | | | 185 | | | | | 190 | | | |
| tac | ttc | gtg | gtg | acc | aac | ttc | ttc | tgg | atg | ttt | gtg | gaa | ggc | tgc | tac | 624 |
| Tyr | Phe | Val | Val | Thr | Asn | Phe | Phe | Trp | Met | Phe | Val | Glu | Gly | Cys | Tyr | |
| | | | | 195 | | | | | 200 | | | | | 205 | | |
| ctg | cac | acg | gcc | att | gtc | atg | acc | tac | tcc | act | gag | cgc | ctg | cgc | aag | 672 |
| Leu | His | Thr | Ala | Ile | Val | Met | Thr | Tyr | Ser | Thr | Glu | Arg | Leu | Arg | Lys | |
| | | 210 | | | | | 215 | | | | | 220 | | | | |
| tgc | ctc | ttc | ctc | ttc | atc | gga | tgg | tgc | atc | ccc | ttc | ccc | atc | atc | gtc | 720 |
| Cys | Leu | Phe | Leu | Phe | Ile | Gly | Trp | Cys | Ile | Pro | Phe | Pro | Ile | Ile | Val | |
| 225 | | | | | 230 | | | | | 235 | | | | | 240 | |
| gcc | tgg | gcc | atc | ggc | aag | ctc | tac | tat | gag | aat | gaa | cag | tgc | tgg | ttt | 768 |
| Ala | Trp | Ala | Ile | Gly | Lys | Leu | Tyr | Tyr | Glu | Asn | Glu | Gln | Cys | Trp | Phe | |
| | | | | 245 | | | | | 250 | | | | | 255 | | |
| ggc | aag | gag | cct | ggc | gac | ctg | gtg | gac | tac | atc | tac | caa | ggc | ccc | atc | 816 |
| Gly | Lys | Glu | Pro | Gly | Asp | Leu | Val | Asp | Tyr | Ile | Tyr | Gln | Gly | Pro | Ile | |
| | | | 260 | | | | | 265 | | | | | 270 | | | |
| att | ctc | gtg | ctc | ctg | atc | aat | ttc | gta | ttt | ctg | ttc | aac | atc | gtc | agg | 864 |
| Ile | Leu | Val | Leu | Leu | Ile | Asn | Phe | Val | Phe | Leu | Phe | Asn | Ile | Val | Arg | |
| | | | | 275 | | | | | 280 | | | | | 285 | | |

| | | |
|---|---|---|
| atc cta atg aca aag tta cgc gcg tcc acc aca tcc gag aca atc cag<br>Ile Leu Met Thr Lys Leu Arg Ala Ser Thr Thr Ser Glu Thr Ile Gln<br>290                         295                   300 | | 912 |
| tac agg aag gca gtg aag gcc acc ctg gtg ctc ctg ccc ctc ctg ggc<br>Tyr Arg Lys Ala Val Lys Ala Thr Leu Val Leu Leu Pro Leu Leu Gly<br>305                     310                   315                   320 | | 960 |
| atc acc tac atg ctc ttc ttc gtc aat ccc ggg gag gac gac ctg tca<br>Ile Thr Tyr Met Leu Phe Phe Val Asn Pro Gly Glu Asp Asp Leu Ser<br>                  325                   330                   335 | | 1008 |
| cag atc atg ttc atc tat ttc aac tcc ttc ctg cag tcg ttc cag ggt<br>Gln Ile Met Phe Ile Tyr Phe Asn Ser Phe Leu Gln Ser Phe Gln Gly<br>           340                   345                   350 | | 1056 |
| ttc ttc gtg tct gtc ttc tac tgc ttc ttc aat gga gag gtg cgc tca<br>Phe Phe Val Ser Val Phe Tyr Cys Phe Phe Asn Gly Glu Val Arg Ser<br>                 355                   360                   365 | | 1104 |
| gcc gtg agg aag agg tgg cac cgc tgg cag gac cat cac tcc ctt cga<br>Ala Val Arg Lys Arg Trp His Arg Trp Gln Asp His His Ser Leu Arg<br>370                         375                   380 | | 1152 |
| gtc ccc atg gcc cgg gcc atg tcc atc cct aca tca ccc aca cgg atc<br>Val Pro Met Ala Arg Ala Met Ser Ile Pro Thr Ser Pro Thr Arg Ile<br>385                     390                   395                   400 | | 1200 |
| agc ttc cac agc atc aag cag acg gcc gct gtg tgaccccctcg gtcgcccacc<br>Ser Phe His Ser Ile Lys Gln Thr Ala Ala Val<br>                  405                   410 | | 1253 |
| tgcacagctc ccctgtcctc ctccaccttc ttcctctggg ttctctgtgc tgggcaggct | | 1313 |
| ctcgtggggc aggagatggg aggggagaga ccagctctcc agcctggcag gaaagagggg | | 1373 |
| gtgcggcagc caagggggac tgcaagggac agggatgagt gggggccacc aggctcagcg | | 1433 |
| caagaggaag cagagggaat tcacaggacc ccctgagaag agccagtcag atgtctgcag | | 1493 |
| gcatttgccc atcccagcct ctctggccag ggccttactg gcccagagc agagaaggac | | 1553 |
| ctgtccaaca cacacagcta tttatagtag cagacacagg gctcccctgc cctactcatg | | 1613 |
| gagccagcag ccaggcaatg gtgtggccct gcactggccc ttggactcca cactcagtgg | | 1673 |
| tgccctgcag ttgggtgggt tacgccagca aggatcagt ttggctgcct tatcccaggg | | 1733 |
| ctgtcaccta gagaggctca cttgtacccc accctgttcc tgtgtcccct ccccagccat | | 1793 |
| cctcccgcct tggggctcc atgaaggat caggcttcca ggcctggctt cctctcttgg | | 1853 |
| gagacccctt ctctgcctag tccacagatt aggcaatcaa ggaagacgcc atcagggaag | | 1913 |
| ccacatcctt agtcaaccag ttgcatcgtg cggggcaaaa tgaggagcag aggcatggag | | 1973 |
| gagggaggcg tgggatggga atagcagaac caccatgtct tcagtgattg aaactcatac | | 2033 |
| cccattgccc tttgccctcc agtctccct tcagaaacat ctctgctctc tgtgaaataa | | 2093 |
| accatgcctc ttgg | | 2107 |

```
<210> SEQ ID NO 2
<211> LENGTH: 411
<212> TYPE: PRT
<213> ORGANISM: homo sapien

<400> SEQUENCE: 2
```

Met Asp Ala Ala Leu Leu His Ser Leu Leu Glu Ala Asn Cys Ser Leu
1               5                   10                  15

Ala Leu Ala Glu Glu Leu Leu Leu Asp Gly Trp Gly Pro Pro Leu Asp
                20                   25                   30

Pro Glu Gly Pro Tyr Ser Tyr Cys Asn Thr Thr Leu Asp Gln Ile Gly
                   35                   40                   45

Thr Cys Trp Pro Arg Ser Ala Gly Ala Leu Val Glu Arg Pro Cys
50                  55                  60

Pro Glu Tyr Phe Asn Gly Val Lys Tyr Asn Thr Thr Arg Asn Ala Tyr
65                  70                  75                  80

Arg Glu Cys Leu Glu Asn Gly Thr Trp Ala Ser Lys Ile Asn Tyr Ser
                85                  90                  95

Gln Cys Glu Pro Ile Leu Asp Asp Lys Gln Arg Lys Tyr Asp Leu His
            100                 105                 110

Tyr Arg Ile Ala Leu Val Val Asn Tyr Leu Gly His Cys Val Ser Val
        115                 120                 125

Ala Ala Leu Val Ala Ala Phe Leu Leu Phe Leu Ala Leu Arg Ser Ile
    130                 135                 140

Arg Cys Leu Arg Asn Val Ile His Trp Asn Leu Ile Thr Thr Phe Ile
145                 150                 155                 160

Leu Arg Asn Val Met Trp Phe Leu Leu Gln Leu Val Asp His Glu Val
                165                 170                 175

His Glu Ser Asn Glu Val Trp Cys Arg Cys Ile Thr Thr Ile Phe Asn
            180                 185                 190

Tyr Phe Val Val Thr Asn Phe Phe Trp Met Phe Val Glu Gly Cys Tyr
        195                 200                 205

Leu His Thr Ala Ile Val Met Thr Tyr Ser Thr Glu Arg Leu Arg Lys
    210                 215                 220

Cys Leu Phe Leu Phe Ile Gly Trp Cys Ile Pro Phe Pro Ile Ile Val
225                 230                 235                 240

Ala Trp Ala Ile Gly Lys Leu Tyr Tyr Glu Asn Glu Gln Cys Trp Phe
                245                 250                 255

Gly Lys Glu Pro Gly Asp Leu Val Asp Tyr Ile Tyr Gln Gly Pro Ile
            260                 265                 270

Ile Leu Val Leu Leu Ile Asn Phe Val Phe Leu Phe Asn Ile Val Arg
        275                 280                 285

Ile Leu Met Thr Lys Leu Arg Ala Ser Thr Thr Ser Glu Thr Ile Gln
    290                 295                 300

Tyr Arg Lys Ala Val Lys Ala Thr Leu Val Leu Leu Pro Leu Leu Gly
305                 310                 315                 320

Ile Thr Tyr Met Leu Phe Phe Val Asn Pro Gly Glu Asp Asp Leu Ser
                325                 330                 335

Gln Ile Met Phe Ile Tyr Phe Asn Ser Phe Leu Gln Ser Phe Gln Gly
            340                 345                 350

Phe Phe Val Ser Val Phe Tyr Cys Phe Phe Asn Gly Glu Val Arg Ser
        355                 360                 365

Ala Val Arg Lys Arg Trp His Arg Trp Gln Asp His His Ser Leu Arg
    370                 375                 380

Val Pro Met Ala Arg Ala Met Ser Ile Pro Thr Ser Pro Thr Arg Ile
385                 390                 395                 400

Ser Phe His Ser Ile Lys Gln Thr Ala Ala Val
                405                 410

<210> SEQ ID NO 3
<211> LENGTH: 1997
<212> TYPE: DNA
<213> ORGANISM: homo sapien
<220> FEATURE:
<221> NAME/KEY: CDS
<222> LOCATION: (1)..(405)

<400> SEQUENCE: 3

```
atg gac gcg gca ctg ctc cac agc ctg ctg gag gcc aac tgc agc ctg      48
Met Asp Ala Ala Leu Leu His Ser Leu Leu Glu Ala Asn Cys Ser Leu
1               5                   10                  15 gcg ctg gct gaa gag ctg ctc ttg gac ggc tgg ggg cca ccc ctg gac      96
Ala Leu Ala Glu Glu Leu Leu Leu Asp Gly Trp Gly Pro Pro Leu Asp
                20                  25                  30 ccc gag ggt ccc tac tcc tac tgc aac acg acc ttg gac cag atc gga     144
Pro Glu Gly Pro Tyr Ser Tyr Cys Asn Thr Thr Leu Asp Gln Ile Gly
            35                  40                  45 acg tgc tgg ccc cgc agc gct gcc gga gcc ctc gtg gag agg ccg tgc     192
Thr Cys Trp Pro Arg Ser Ala Ala Gly Ala Leu Val Glu Arg Pro Cys
        50                  55                  60 ccc gag tac ttc aac ggc gtc aag tac aac acg acc cgg aat gcc tat     240
Pro Glu Tyr Phe Asn Gly Val Lys Tyr Asn Thr Thr Arg Asn Ala Tyr
65                  70                  75                  80 cga gaa tgc ttg gag aat ggg acg tgg gcc tca aag atc aac tac tca     288
Arg Glu Cys Leu Glu Asn Gly Thr Trp Ala Ser Lys Ile Asn Tyr Ser
                85                  90                  95 cag tgt gag ccc att ttg gat gac aag gag cat tcg ctg tct gcg gaa     336
Gln Cys Glu Pro Ile Leu Asp Asp Lys Glu His Ser Leu Ser Ala Glu
                100                 105                 110 tgt gat tca ctg gaa cct cat cac cac ctt tat cct gcg aaa tgt cat     384
Cys Asp Ser Leu Glu Pro His His His Leu Tyr Pro Ala Lys Cys His
            115                 120                 125 gtg gtt cct gct gca gct cgt tgaccatgaa gtgcacgaga gcaatgaggt        435
Val Val Pro Ala Ala Ala Arg
        130                 135 ctggtgccgc tgcatcacca ccatcttcaa ctacttcgtg gtgaccaact tcttctggat   495
gtttgtggaa ggctgctacc tgcacacggc cattgtcatg acctactcca ctgagcgcct   555
gcgcaagtgc tcttcctct tcatcggatg gtgcatcccc ttccccatca tcgtcgcctg    615
ggccatcggc aagctctact atgagaatga acagtgctgg tttggcaagg agcctggcga   675
cctggtggac tacatctacc aaggccccat cattctcgtg ctcctgatca atttcgtatt   735
tctgttcaac atcgtcagga tcctaatgac aaagttacgc gcgtccacca catccgagac   795
aatccagtac aggaaggcag tgaaggccac cctggtgctc ctgccctcc tgggcatcac    855 ctacatgctc ttcttcgtca atcccgggga ggacgacctg tcacagatca tgttcatcta   915
tttcaactcc ttcctgcagt cgttccaggg tttcttcgtg tctgtcttct actgcttctt   975
caatggagag gtgcgctcag ccgtgaggaa gaggtggcac cgctggcagg accatcactc   1035
ccttcgagtc cccatggccc gggccatgtc catccctaca tcacccacac ggatcagctt   1095
ccacagcatc aagcagacgg ccgctgtgtg acccctcggt cgcccacctg cacagctccc   1155
ctgtcctcct ccaccttctt cctctgggtt ctctgtgctg ggcaggctct cgtggggcag   1215
gagatgggag gggagagacc agctctccag cctggcagga agaggggt gcggcagcca    1275 agggggactg caagggacag ggatgagtgg gggccaccag gctcagcgca agaggaagca   1335
gagggaattc acaggacccc ctgagaagag ccagtcagat gtctgcaggc atttgcccat   1395
cccagcctct ctggccaggg ccttactggg cccagagcag agaaggacct gtccaacaca   1455
cacagctatt tatagtagca gacacagggc tcccctgccc tactcatgga gccagcagcc   1515
aggcaatggt gtgccctgc actggcccctt ggactccaca ctcagtggtg ccctgcagtt   1575
gggtgggtta cgccagcaaa ggatcagttt ggctgcctta tcccagggct gtcacctaga   1635
gaggctcact tgtaccccac cctgttcctg tgtcccctcc ccagccatcc tcccgccttg   1695
```

-continued

```
ggggctccat gaaggatgca ggcttccagg cctggcttcc tctcttggga gaccccttct      1755
ctgcctagtc cacagattag gcaatcaagg aagacgccac cagggaagcc acatccttag      1815
tcaaccagtt gcatcgtgcg ggcaaaatg aggagcagag gcatggagga gggaggcgtg      1875
ggatgggaat agcagaacca ccatgtcttc agtgattgaa actcataccc cattgccctt      1935
tgccctccag tctcccttc agaaacatct ctgctctctg tgaaataaac catgcctctt      1995
gg                                                                     1997
```

<210> SEQ ID NO 4
<211> LENGTH: 135
<212> TYPE: PRT
<213> ORGANISM: homo sapien

<400> SEQUENCE: 4

```
Met Asp Ala Ala Leu Leu His Ser Leu Leu Glu Ala Asn Cys Ser Leu
1               5                   10                  15

Ala Leu Ala Glu Glu Leu Leu Leu Asp Gly Trp Gly Pro Pro Leu Asp
            20                  25                  30

Pro Glu Gly Pro Tyr Ser Tyr Cys Asn Thr Thr Leu Asp Gln Ile Gly
        35                  40                  45

Thr Cys Trp Pro Arg Ser Ala Ala Gly Ala Leu Val Glu Arg Pro Cys
    50                  55                  60

Pro Glu Tyr Phe Asn Gly Val Lys Tyr Asn Thr Thr Arg Asn Ala Tyr
65                  70                  75                  80

Arg Glu Cys Leu Glu Asn Gly Thr Trp Ala Ser Lys Ile Asn Tyr Ser
                85                  90                  95

Gln Cys Glu Pro Ile Leu Asp Asp Lys Glu His Ser Leu Ser Ala Glu
            100                 105                 110

Cys Asp Ser Leu Glu Pro His His Leu Tyr Pro Ala Lys Cys His
        115                 120                 125

Val Val Pro Ala Ala Ala Arg
    130                 135
```

<210> SEQ ID NO 5
<211> LENGTH: 1320
<212> TYPE: DNA
<213> ORGANISM: homo sapien
<220> FEATURE:
<221> NAME/KEY: CDS
<222> LOCATION: (1)..(1314)

<400> SEQUENCE: 5

```
atg agg ggt ccc tca ggg ccc cca ggc ctc ctc tac gtc cca cac ctc       48
Met Arg Gly Pro Ser Gly Pro Pro Gly Leu Leu Tyr Val Pro His Leu
1               5                   10                  15 ctc ctc tgc ctg ctc tgc ctc ctc cca ccg ccg ctc caa tac gca gcc       96
Leu Leu Cys Leu Leu Cys Leu Leu Pro Pro Pro Leu Gln Tyr Ala Ala
            20                  25                  30 ggg cag agc cag atg ccc aaa gac cag ccc ctg tgg gca ctt ctg gag      144
Gly Gln Ser Gln Met Pro Lys Asp Gln Pro Leu Trp Ala Leu Leu Glu
        35                  40                  45 cag tac tgc cac acc atc atg acc ctc acc aac ctc tca ggt ccc tac      192
Gln Tyr Cys His Thr Ile Met Thr Leu Thr Asn Leu Ser Gly Pro Tyr
    50                  55                  60 tcc tac tgc aac acg acc ttg gac cag atc gga acg tgc tgg ccc cgc      240
Ser Tyr Cys Asn Thr Thr Leu Asp Gln Ile Gly Thr Cys Trp Pro Arg
65                  70                  75                  80 agc gct gcc gga gcc ctc gtg gag agg ccg tgc ccc gag tac ttc aac      288
```

```
                    -continued

Ser Ala Ala Gly Ala Leu Val Glu Arg Pro Cys Pro Glu Tyr Phe Asn
                85               90                   95 ggc gtc aag tac aac acg acc cgg aat gcc tat cga gaa tgc ttg gag    336
Gly Val Lys Tyr Asn Thr Thr Arg Asn Ala Tyr Arg Glu Cys Leu Glu
            100              105                  110 aat ggg acg tgg gcc tca aag atc aac tac tca cag tgt gag ccc att    384
Asn Gly Thr Trp Ala Ser Lys Ile Asn Tyr Ser Gln Cys Glu Pro Ile
        115                  120                  125 ttg gat gac aag cag agg aag tat gac ctg cac tac cgc atc gcc ctt    432
Leu Asp Asp Lys Gln Arg Lys Tyr Asp Leu His Tyr Arg Ile Ala Leu
    130                  135                  140 gtc gtc aac tac ctg ggc cac tgc gta tct gtg gca gcc ctg gtg gcc    480
Val Val Asn Tyr Leu Gly His Cys Val Ser Val Ala Ala Leu Val Ala
145                  150                  155                  160 gcc ttc ctg ctt ttc ctg gcc ctg cgg agc att cgc tgt ctg cgg aat    528
Ala Phe Leu Leu Phe Leu Ala Leu Arg Ser Ile Arg Cys Leu Arg Asn
                165                  170                  175 gtg att cac tgg aac ctc atc acc acc ttt atc ctg cga aat gtc atg    576
Val Ile His Trp Asn Leu Ile Thr Thr Phe Ile Leu Arg Asn Val Met
            180                  185                  190 tgg ttc ctg ctg cag ctc gtt gac cat gaa gtg cac gag agc aat gag    624
Trp Phe Leu Leu Gln Leu Val Asp His Glu Val His Glu Ser Asn Glu
        195                  200                  205 gtc tgg tgc cgc tgc atc acc acc atc ttc aac tac ttc gtg gtg acc    672
Val Trp Cys Arg Cys Ile Thr Thr Ile Phe Asn Tyr Phe Val Val Thr
    210                  215                  220 aac ttc ttc tgg atg ttt gtg gaa ggc tgc tac ctg cac acg gcc att    720
Asn Phe Phe Trp Met Phe Val Glu Gly Cys Tyr Leu His Thr Ala Ile
225                  230                  235                  240 gtc atg acc tac tcc act gag cgc ctg cgc aag tgc ctc ttc ctc ttc    768
Val Met Thr Tyr Ser Thr Glu Arg Leu Arg Lys Cys Leu Phe Leu Phe
                245                  250                  255 atc gga tgg tgc atc ccc ttc ccc atc atc gtc gcc tgg gcc atc ggc    816
Ile Gly Trp Cys Ile Pro Phe Pro Ile Ile Val Ala Trp Ala Ile Gly
            260                  265                  270 aag ctc tac tat gag aat gaa cag tgc tgg ttt ggc aag gag cct ggc    864
Lys Leu Tyr Tyr Glu Asn Glu Gln Cys Trp Phe Gly Lys Glu Pro Gly
        275                  280                  285 gac ctg gtg gac tac atc tac caa ggc ccc atc att ctc gtg ctc ctg    912
Asp Leu Val Asp Tyr Ile Tyr Gln Gly Pro Ile Ile Leu Val Leu Leu
    290                  295                  300 atc aat ttc gta ttt ctg ttc aac atc gtc agg atc cta atg aca aag    960
Ile Asn Phe Val Phe Leu Phe Asn Ile Val Arg Ile Leu Met Thr Lys
305                  310                  315                  320 tta cgc gcg tcc acc aca tcc gag aca atc cag tac agg aag gca gtg    1008
Leu Arg Ala Ser Thr Thr Ser Glu Thr Ile Gln Tyr Arg Lys Ala Val
                325                  330                  335 aag gcc acc ctg gtg ctc ctg ccc ctg ctg ggc atc acc tac atg ctc    1056
Lys Ala Thr Leu Val Leu Leu Pro Leu Leu Gly Ile Thr Tyr Met Leu
            340                  345                  350 ttc ttc gtc aat ccc ggg gag gac gac ctg tca cag atc atg ttc atc    1104
Phe Phe Val Asn Pro Gly Glu Asp Asp Leu Ser Gln Ile Met Phe Ile
        355                  360                  365 tat ttc aac tcc ttc ctg cag tcg ttc cag ggt ttc ttc gtg tct gtc    1152
Tyr Phe Asn Ser Phe Leu Gln Ser Phe Gln Gly Phe Phe Val Ser Val
    370                  375                  380 ttc tac tgc ttc ttc aat gga gag gtg cgc tca gcc gtg agg aag agg    1200
Phe Tyr Cys Phe Phe Asn Gly Glu Val Arg Ser Ala Val Arg Lys Arg
385                  390                  395                  400
```

```
tgg cac cgc tgg cag gac cat cac tcc ctt cga gtc ccc atg gcc cgg    1248
Trp His Arg Trp Gln Asp His His Ser Leu Arg Val Pro Met Ala Arg
                405                 410                 415 gcc atg tcc atc cct aca tca ccc aca cgg atc agc ttc cac agc atc    1296
Ala Met Ser Ile Pro Thr Ser Pro Thr Arg Ile Ser Phe His Ser Ile
        420                 425                 430 aag cag acg gcc gct gtg tgaccc                                      1320
Lys Gln Thr Ala Ala Val
        435
```

<210> SEQ ID NO 6
<211> LENGTH: 438
<212> TYPE: PRT
<213> ORGANISM: homo sapien

<400> SEQUENCE: 6

```
Met Arg Gly Pro Ser Gly Pro Pro Gly Leu Leu Tyr Val Pro His Leu
1               5                   10                  15

Leu Leu Cys Leu Leu Cys Leu Leu Pro Pro Leu Gln Tyr Ala Ala
            20                  25                  30

Gly Gln Ser Gln Met Pro Lys Asp Gln Pro Leu Trp Ala Leu Leu Glu
        35                  40                  45

Gln Tyr Cys His Thr Ile Met Thr Leu Thr Asn Leu Ser Gly Pro Tyr
    50                  55                  60

Ser Tyr Cys Asn Thr Thr Leu Asp Gln Ile Gly Thr Cys Trp Pro Arg
65                  70                  75                  80

Ser Ala Ala Gly Ala Leu Val Glu Arg Pro Cys Pro Glu Tyr Phe Asn
                85                  90                  95

Gly Val Lys Tyr Asn Thr Thr Arg Asn Ala Tyr Arg Glu Cys Leu Glu
            100                 105                 110

Asn Gly Thr Trp Ala Ser Lys Ile Asn Tyr Ser Gln Cys Glu Pro Ile
        115                 120                 125

Leu Asp Asp Lys Gln Arg Lys Tyr Asp Leu His Tyr Arg Ile Ala Leu
    130                 135                 140

Val Val Asn Tyr Leu Gly His Cys Val Ser Val Ala Ala Leu Val Ala
145                 150                 155                 160

Ala Phe Leu Leu Phe Leu Ala Leu Arg Ser Ile Arg Cys Leu Arg Asn
                165                 170                 175

Val Ile His Trp Asn Leu Ile Thr Thr Phe Ile Leu Arg Asn Val Met
            180                 185                 190

Trp Phe Leu Leu Gln Leu Val Asp His Glu Val His Glu Ser Asn Glu
        195                 200                 205

Val Trp Cys Arg Cys Ile Thr Thr Ile Phe Asn Tyr Phe Val Val Thr
    210                 215                 220

Asn Phe Phe Trp Met Phe Val Glu Gly Cys Tyr Leu His Thr Ala Ile
225                 230                 235                 240

Val Met Thr Tyr Ser Thr Glu Arg Leu Arg Lys Cys Leu Phe Leu Phe
                245                 250                 255

Ile Gly Trp Cys Ile Pro Phe Pro Ile Ile Val Ala Trp Ala Ile Gly
            260                 265                 270

Lys Leu Tyr Tyr Glu Asn Glu Gln Cys Trp Phe Gly Lys Glu Pro Gly
        275                 280                 285

Asp Leu Val Asp Tyr Ile Tyr Gln Gly Pro Ile Ile Leu Val Leu Leu
    290                 295                 300

Ile Asn Phe Val Phe Leu Phe Asn Ile Val Arg Ile Leu Met Thr Lys
305                 310                 315                 320
```

```
Leu Arg Ala Ser Thr Thr Ser Glu Thr Ile Gln Tyr Arg Lys Ala Val
                325                 330                 335

Lys Ala Thr Leu Val Leu Leu Pro Leu Leu Gly Ile Thr Tyr Met Leu
            340                 345                 350

Phe Phe Val Asn Pro Gly Glu Asp Leu Ser Gln Ile Met Phe Ile
            355                 360                 365

Tyr Phe Asn Ser Phe Leu Gln Ser Phe Gln Gly Phe Phe Val Ser Val
    370                 375                 380

Phe Tyr Cys Phe Phe Asn Gly Glu Val Arg Ser Ala Val Arg Lys Arg
385                 390                 395                 400

Trp His Arg Trp Gln Asp His His Ser Leu Arg Val Pro Met Ala Arg
                405                 410                 415

Ala Met Ser Ile Pro Thr Ser Pro Thr Arg Ile Ser Phe His Ser Ile
            420                 425                 430

Lys Gln Thr Ala Ala Val
            435

<210> SEQ ID NO 7
<211> LENGTH: 1249
<212> TYPE: DNA
<213> ORGANISM: homo sapien
<220> FEATURE:
<221> NAME/KEY: CDS
<222> LOCATION: (1)..(525)

<400> SEQUENCE: 7 atg agg ggt ccc tca ggg ccc cca ggc ctc ctc tac gtc cca cac ctc    48
Met Arg Gly Pro Ser Gly Pro Pro Gly Leu Leu Tyr Val Pro His Leu
1               5                   10                  15 ctc ctc tgc ctg ctc tgc ctc ctc cca ccg ccg ctc caa tac gca gcc    96
Leu Leu Cys Leu Leu Cys Leu Leu Pro Pro Pro Leu Gln Tyr Ala Ala
            20                  25                  30 ggg cag agc cag atg ccc aaa gac cag ccc ctg tgg gca ctt ctg gag   144
Gly Gln Ser Gln Met Pro Lys Asp Gln Pro Leu Trp Ala Leu Leu Glu
        35                  40                  45 cag tac tgc cac acc atc atg acc ctc acc aac ctc tca ggt ccc tac   192
Gln Tyr Cys His Thr Ile Met Thr Leu Thr Asn Leu Ser Gly Pro Tyr
    50                  55                  60 tcc tac tgc aac acg acc ttg gac cag atc gga acg tgc tgg ccc cgc   240
Ser Tyr Cys Asn Thr Thr Leu Asp Gln Ile Gly Thr Cys Trp Pro Arg
65                  70                  75                  80 agc gct gcc gga gcc ctc gtg gag agg ccg tgc ccc gag tac ttc aac   288
Ser Ala Ala Gly Ala Leu Val Glu Arg Pro Cys Pro Glu Tyr Phe Asn
                85                  90                  95 ggc gtc aag tac aac acg acc cgg aat gcc tat cga gaa tgc ttg gag   336
Gly Val Lys Tyr Asn Thr Thr Arg Asn Ala Tyr Arg Glu Cys Leu Glu
            100                 105                 110 aat ggg acg tgg gcc tca aag atc aac tac tca cag tgt gag ccc att   384
Asn Gly Thr Trp Ala Ser Lys Ile Asn Tyr Ser Gln Cys Glu Pro Ile
        115                 120                 125 ttg gat gac aag cag agg aag tat gac ctg cac tac cgc atc gcc ctt   432
Leu Asp Asp Lys Gln Arg Lys Tyr Asp Leu His Tyr Arg Ile Ala Leu
    130                 135                 140 gtc gag cat tcg ctg tct gcg gaa tgt gat tca ctg gaa cct cat cac   480
Val Glu His Ser Leu Ser Ala Glu Cys Asp Ser Leu Glu Pro His His
145                 150                 155                 160 cac ctt tat cct gcg aaa tgt cat gtg gtt cct gct gca gct cgt        525
His Leu Tyr Pro Ala Lys Cys His Val Val Pro Ala Ala Ala Arg
                165                 170                 175
```

```
tgaccatgaa gtgcacgaga gcaatgaggt ctggtgccgc tgcatcacca ccatcttcaa      585
ctacttcgtg gtgaccaact tcttctggat gtttgtggaa ggctgctacc tgcacacggc      645
cattgtcatg acctactcca ctgagcgcct gcgcaagtgc ctcttcctct tcatcggatg      705
gtgcatcccc ttccccatca tcgtcgcctg ggccatcggc aagctctact atgagaatga      765
acagtgctgg tttggcaagg agcctggcga cctggtggac tacatctacc aaggccccat      825
cattctcgtg ctcctgatca atttcgtatt tctgttcaac atcgtcagga tcctaatgac      885
aaagttacgc gcgtccacca catccgagac aatccagtac aggaaggcag tgaaggccac      945
cctggtgctc ctgccccctcc tgggcatcac ctacatgctc ttcttcgtca atcccgggga    1005
ggacgacctg tcacagatca tgttcatcta tttcaactcc ttcctgcagt cgttccaggg    1065
tttcttcgtg tctgtcttct actgcttctt caatggagag gtgcgctcag ccgtgaggaa    1125
gaggtggcac cgctggcagg accatcactc ccttcgagtc cccatggccc gggccatgtc    1185
catccctaca tcacccacac ggatcagctt ccacagcatc aagcagacgg ccgctgtgtg    1245
accc                                                                  1249
```

<210> SEQ ID NO 8
<211> LENGTH: 175
<212> TYPE: PRT
<213> ORGANISM: homo sapien

<400> SEQUENCE: 8

```
Met Arg Gly Pro Ser Gly Pro Pro Gly Leu Leu Tyr Val Pro His Leu
1               5                   10                  15

Leu Leu Cys Leu Leu Cys Leu Leu Pro Pro Leu Gln Tyr Ala Ala
            20                  25                  30

Gly Gln Ser Gln Met Pro Lys Asp Gln Pro Leu Trp Ala Leu Leu Glu
        35                  40                  45

Gln Tyr Cys His Thr Ile Met Thr Leu Thr Asn Leu Ser Gly Pro Tyr
    50                  55                  60

Ser Tyr Cys Asn Thr Thr Leu Asp Gln Ile Gly Thr Cys Trp Pro Arg
65                  70                  75                  80

Ser Ala Ala Gly Ala Leu Val Glu Arg Pro Cys Pro Glu Tyr Phe Asn
                85                  90                  95

Gly Val Lys Tyr Asn Thr Thr Arg Asn Ala Tyr Arg Glu Cys Leu Glu
            100                 105                 110

Asn Gly Thr Trp Ala Ser Lys Ile Asn Tyr Ser Gln Cys Glu Pro Ile
        115                 120                 125

Leu Asp Asp Lys Gln Arg Lys Tyr Asp Leu His Tyr Arg Ile Ala Leu
    130                 135                 140

Val Glu His Ser Leu Ser Ala Glu Cys Asp Ser Leu Glu Pro His His
145                 150                 155                 160

His Leu Tyr Pro Ala Lys Cys His Val Val Pro Ala Ala Ala Arg
                165                 170                 175
```

<210> SEQ ID NO 9
<211> LENGTH: 1199
<212> TYPE: DNA
<213> ORGANISM: homo sapien
<220> FEATURE:
<221> NAME/KEY: CDS
<222> LOCATION: (1)..(1197)

<400> SEQUENCE: 9

-continued

| | | |
|---|---|---|
| atg gga aga gag cct tgg cct gaa gac agg gac ctg ggc ttt cct cag<br>Met Gly Arg Glu Pro Trp Pro Glu Asp Arg Asp Leu Gly Phe Pro Gln<br>1               5                   10                  15 | 48 |
| ctc ttc tgc caa ggt ccc tac tcc tac tgc aac acg acc ttg gac cag<br>Leu Phe Cys Gln Gly Pro Tyr Ser Tyr Cys Asn Thr Thr Leu Asp Gln<br>            20                  25                  30 | 96 |
| atc gga acg tgc tgg ccc cgc agc gct gcc gga gcc ctc gtg gag agg<br>Ile Gly Thr Cys Trp Pro Arg Ser Ala Ala Gly Ala Leu Val Glu Arg<br>        35                  40                  45 | 144 |
| ccg tgc ccc gag tac ttc aac ggc gtc aag tac aac acg acc cgg aat<br>Pro Cys Pro Glu Tyr Phe Asn Gly Val Lys Tyr Asn Thr Thr Arg Asn<br>50                  55                  60 | 192 |
| gcc tat cga gaa tgc ttg gag aat ggg acg tgg gcc tca aag atc aac<br>Ala Tyr Arg Glu Cys Leu Glu Asn Gly Thr Trp Ala Ser Lys Ile Asn<br>65                  70                  75                  80 | 240 |
| tac tca cag tgt gag ccc att ttg gat gac aag cag agg aag tat gac<br>Tyr Ser Gln Cys Glu Pro Ile Leu Asp Asp Lys Gln Arg Lys Tyr Asp<br>                85                  90                  95 | 288 |
| ctg cac tac cgc atc gcc ctt gtc gtc aac tac ctg ggc cac tgc gta<br>Leu His Tyr Arg Ile Ala Leu Val Val Asn Tyr Leu Gly His Cys Val<br>            100                 105                 110 | 336 |
| tct gtg gca gcc ctg gtg gcc gcc ttc ctg ctt ttc ctg gcc ctg cgg<br>Ser Val Ala Ala Leu Val Ala Ala Phe Leu Leu Phe Leu Ala Leu Arg<br>        115                 120                 125 | 384 |
| agc att cgc tgt ctg cgg aat gtg att cac tgg aac ctc atc acc acc<br>Ser Ile Arg Cys Leu Arg Asn Val Ile His Trp Asn Leu Ile Thr Thr<br>130                 135                 140 | 432 |
| ttt atc ctg cga aat gtc atg tgg ttc ctg cag ctc gtt gac cat<br>Phe Ile Leu Arg Asn Val Met Trp Phe Leu Leu Gln Leu Val Asp His<br>145                 150                 155                 160 | 480 |
| gaa gtg cac gag agc aat gag gtc tgg tgc cgc tgc atc acc acc atc<br>Glu Val His Glu Ser Asn Glu Val Trp Cys Arg Cys Ile Thr Thr Ile<br>                165                 170                 175 | 528 |
| ttc aac tac ttc gtg gtg acc aac ttc ttc tgg atg ttt gtg gaa ggc<br>Phe Asn Tyr Phe Val Val Thr Asn Phe Phe Trp Met Phe Val Glu Gly<br>            180                 185                 190 | 576 |
| tgc tac ctg cac acg gcc att gtc atg acc tac tcc act gag cgc ctg<br>Cys Tyr Leu His Thr Ala Ile Val Met Thr Tyr Ser Thr Glu Arg Leu<br>        195                 200                 205 | 624 |
| cgc aag tgc ctc ttc ctc ttc atc gga tgg tgc atc ccc ttc ccc atc<br>Arg Lys Cys Leu Phe Leu Phe Ile Gly Trp Cys Ile Pro Phe Pro Ile<br>210                 215                 220 | 672 |
| atc gtc gcc tgg gcc atc ggc aag ctc tac tat gag aat gaa cag tgc<br>Ile Val Ala Trp Ala Ile Gly Lys Leu Tyr Tyr Glu Asn Glu Gln Cys<br>225                 230                 235                 240 | 720 |
| tgg ttt ggc aag gag cct ggc gac ctg gtg gac tac atc tac caa ggc<br>Trp Phe Gly Lys Glu Pro Gly Asp Leu Val Asp Tyr Ile Tyr Gln Gly<br>                245                 250                 255 | 768 |
| ccc atc att ctc gtg ctc ctg atc aat ttc gta ttt ctg ttc aac atc<br>Pro Ile Ile Leu Val Leu Leu Ile Asn Phe Val Phe Leu Phe Asn Ile<br>            260                 265                 270 | 816 |
| gtc agg atc cta atg aca aag tta cgc gcg tcc acc aca tcc gag aca<br>Val Arg Ile Leu Met Thr Lys Leu Arg Ala Ser Thr Thr Ser Glu Thr<br>        275                 280                 285 | 864 |
| atc cag tac agg aag gca gtg aag gcc acc ctg gtg ctc ctg ccc ctc<br>Ile Gln Tyr Arg Lys Ala Val Lys Ala Thr Leu Val Leu Leu Pro Leu<br>        290                 295                 300 | 912 |
| ctg ggc atc acc tac atg ctc ttc ttc gtc aat ccc ggg gag gac gac<br>Leu Gly Ile Thr Tyr Met Leu Phe Phe Val Asn Pro Gly Glu Asp Asp<br>305                 310                 315                 320 | 960 |

```
ctg tca cag atc atg ttc atc tat ttc aac tcc ttc ctg cag tcg ttc      1008
Leu Ser Gln Ile Met Phe Ile Tyr Phe Asn Ser Phe Leu Gln Ser Phe
            325                 330                 335 cag ggt ttc ttc gtg tct gtc ttc tac tgc ttc ttc aat gga gag gtg      1056
Gln Gly Phe Phe Val Ser Val Phe Tyr Cys Phe Phe Asn Gly Glu Val
        340                 345                 350 cgc tca gcc gtg agg aag agg tgg cac cgc tgg cag gac cat cac tcc      1104
Arg Ser Ala Val Arg Lys Arg Trp His Arg Trp Gln Asp His His Ser
    355                 360                 365 ctt cga gtc ccc atg gcc cgg gcc atg tcc atc cct aca tca ccc aca      1152
Leu Arg Val Pro Met Ala Arg Ala Met Ser Ile Pro Thr Ser Pro Thr
370                 375                 380 cgg atc agc ttc cac agc atc aag cag acg gcc gct gtg tga ccc ct       1199
Arg Ile Ser Phe His Ser Ile Lys Gln Thr Ala Ala Val     Pro
385                 390                 395

<210> SEQ ID NO 10
<211> LENGTH: 397
<212> TYPE: PRT
<213> ORGANISM: homo sapien

<400> SEQUENCE: 10

Met Gly Arg Glu Pro Trp Pro Glu Asp Arg Asp Leu Gly Phe Pro Gln
1               5                   10                  15

Leu Phe Cys Gln Gly Pro Tyr Ser Tyr Cys Asn Thr Thr Leu Asp Gln
            20                  25                  30

Ile Gly Thr Cys Trp Pro Arg Ser Ala Ala Gly Ala Leu Val Glu Arg
        35                  40                  45

Pro Cys Pro Glu Tyr Phe Asn Gly Val Lys Tyr Asn Thr Thr Arg Asn
    50                  55                  60

Ala Tyr Arg Glu Cys Leu Glu Asn Gly Thr Trp Ala Ser Lys Ile Asn
65                  70                  75                  80

Tyr Ser Gln Cys Glu Pro Ile Leu Asp Asp Lys Gln Arg Lys Tyr Asp
                85                  90                  95

Leu His Tyr Arg Ile Ala Leu Val Val Asn Tyr Leu Gly His Cys Val
            100                 105                 110

Ser Val Ala Ala Leu Val Ala Ala Phe Leu Leu Phe Leu Ala Leu Arg
        115                 120                 125

Ser Ile Arg Cys Leu Arg Asn Val Ile His Trp Asn Leu Ile Thr Thr
130                 135                 140

Phe Ile Leu Arg Asn Val Met Trp Phe Leu Leu Gln Leu Val Asp His
145                 150                 155                 160

Glu Val His Glu Ser Asn Glu Val Trp Cys Arg Cys Ile Thr Thr Ile
                165                 170                 175

Phe Asn Tyr Phe Val Val Thr Asn Phe Phe Trp Met Phe Val Glu Gly
            180                 185                 190

Cys Tyr Leu His Thr Ala Ile Val Met Thr Tyr Ser Thr Glu Arg Leu
        195                 200                 205

Arg Lys Cys Leu Phe Leu Phe Ile Gly Trp Cys Ile Pro Phe Pro Ile
    210                 215                 220

Ile Val Ala Trp Ala Ile Gly Lys Leu Tyr Tyr Glu Asn Glu Gln Cys
225                 230                 235                 240

Trp Phe Gly Lys Glu Pro Gly Asp Leu Val Asp Tyr Ile Tyr Gln Gly
                245                 250                 255

Pro Ile Ile Leu Val Leu Leu Ile Asn Phe Val Phe Leu Phe Asn Ile
            260                 265                 270
```

```
Val Arg Ile Leu Met Thr Lys Leu Arg Ala Ser Thr Thr Ser Glu Thr
        275                 280                 285

Ile Gln Tyr Arg Lys Ala Val Lys Ala Thr Leu Val Leu Leu Pro Leu
    290                 295                 300

Leu Gly Ile Thr Tyr Met Leu Phe Phe Val Asn Pro Gly Glu Asp Asp
305                 310                 315                 320

Leu Ser Gln Ile Met Phe Ile Tyr Phe Asn Ser Phe Leu Gln Ser Phe
                325                 330                 335

Gln Gly Phe Phe Val Ser Val Phe Tyr Cys Phe Phe Asn Gly Glu Val
                340                 345                 350

Arg Ser Ala Val Arg Lys Arg Trp His Arg Trp Gln Asp His His Ser
            355                 360                 365

Leu Arg Val Pro Met Ala Arg Ala Met Ser Ile Pro Thr Ser Pro Thr
        370                 375                 380

Arg Ile Ser Phe His Ser Ile Lys Gln Thr Ala Ala Val
385                 390                 395

<210> SEQ ID NO 11
<211> LENGTH: 1128
<212> TYPE: DNA
<213> ORGANISM: homo sapien
<220> FEATURE:
<221> NAME/KEY: CDS
<222> LOCATION: (1)..(402)

<400> SEQUENCE: 11 atg gga aga gag cct tgg cct gaa gac agg gac ctg ggc ttt cct cag      48
Met Gly Arg Glu Pro Trp Pro Glu Asp Arg Asp Leu Gly Phe Pro Gln
1               5                   10                  15 ctc ttc tgc caa ggt ccc tac tcc tac tgc aac acg acc ttg gac cag      96
Leu Phe Cys Gln Gly Pro Tyr Ser Tyr Cys Asn Thr Thr Leu Asp Gln
            20                  25                  30 atc gga acg tgc tgg ccc cgc agc gct gcc gga gcc ctc gtg gag agg     144
Ile Gly Thr Cys Trp Pro Arg Ser Ala Ala Gly Ala Leu Val Glu Arg
        35                  40                  45 ccg tgc ccc gag tac ttc aac ggc gtc aag tac aac acg acc cgg aat     192
Pro Cys Pro Glu Tyr Phe Asn Gly Val Lys Tyr Asn Thr Thr Arg Asn
    50                  55                  60 gcc tat cga gaa tgc ttg gag aat ggg acg tgg gcc tca aag atc aac     240
Ala Tyr Arg Glu Cys Leu Glu Asn Gly Thr Trp Ala Ser Lys Ile Asn
65                  70                  75                  80 tac tca cag tgt gag ccc att ttg gat gac aag cag agg aag tat gac     288
Tyr Ser Gln Cys Glu Pro Ile Leu Asp Asp Lys Gln Arg Lys Tyr Asp
                85                  90                  95 ctg cac tac cgc atc gcc ctt gtc gag cat tcg ctg tct gcg gaa tgt     336
Leu His Tyr Arg Ile Ala Leu Val Glu His Ser Leu Ser Ala Glu Cys
            100                 105                 110 gat tca ctg gaa cct cat cac cac ctt tat cct gcg aaa tgt cat gtg     384
Asp Ser Leu Glu Pro His His His Leu Tyr Pro Ala Lys Cys His Val
        115                 120                 125 gtt cct gct gca gct cgt tgaccatgaa gtgcacgaga gcaatgaggt            432
Val Pro Ala Ala Ala Arg
        130 ctggtgccgc tgcatcacca ccatcttcaa ctacttcgtg gtgaccaact tcttctggat    492 gtttgtggaa ggctgctacc tgcacacggc cattgtcatg acctactcca ctgagcgcct    552 gcgcaagtgc ctcttcctct tcatcggatg gtgcatcccc ttccccatca tcgtcgcctg    612 ggccatcggc aagctctact atgagaatga acagtgctgg tttggcaagg agcctggcga    672
```

```
cctggtggac tacatctacc aaggccccat cattctcgtg ctcctgatca atttcgtatt      732
tctgttcaac atcgtcagga tcctaatgac aaagttacgc gcgtccacca catccgagac      792
aatccagtac aggaaggcag tgaaggccac cctggtgctc ctgccctcc  tgggcatcac      852 ctacatgctc ttcttcgtca atcccgggga ggacgacctg tcacagatca tgttcatcta      912
tttcaactcc ttcctgcagt cgttccaggg tttcttcgtg tctgtcttct actgcttctt      972
caatggagag gtgcgctcag ccgtgaggaa gaggtggcac cgctggcagg accatcactc     1032
ccttcgagtc cccatggccc gggccatgtc catccctaca tcacccacac ggatcagctt     1092
ccacagcatc aagcagacgg ccgctgtgtg acccct                               1128

<210> SEQ ID NO 12
<211> LENGTH: 134
<212> TYPE: PRT
<213> ORGANISM: homo sapien

<400> SEQUENCE: 12

Met Gly Arg Glu Pro Trp Pro Glu Asp Arg Asp Leu Gly Phe Pro Gln
1               5                   10                  15

Leu Phe Cys Gln Gly Pro Tyr Ser Tyr Cys Asn Thr Thr Leu Asp Gln
            20                  25                  30

Ile Gly Thr Cys Trp Pro Arg Ser Ala Ala Gly Ala Leu Val Glu Arg
        35                  40                  45

Pro Cys Pro Glu Tyr Phe Asn Gly Val Lys Tyr Asn Thr Thr Arg Asn
    50                  55                  60

Ala Tyr Arg Glu Cys Leu Glu Asn Gly Thr Trp Ala Ser Lys Ile Asn
65                  70                  75                  80

Tyr Ser Gln Cys Glu Pro Ile Leu Asp Asp Lys Gln Arg Lys Tyr Asp
                85                  90                  95

Leu His Tyr Arg Ile Ala Leu Val Glu His Ser Leu Ser Ala Glu Cys
            100                 105                 110

Asp Ser Leu Glu Pro His His His Leu Tyr Pro Ala Lys Cys His Val
        115                 120                 125

Val Pro Ala Ala Ala Arg
    130

<210> SEQ ID NO 13
<211> LENGTH: 32990
<212> TYPE: DNA
<213> ORGANISM: homo sapien
<220> FEATURE:
<221> NAME/KEY: gene
<222> LOCATION: (1)..(32990)

<400> SEQUENCE: 13
tcacacagcg gccgtctgct tgatgctgtg gaagctgatc cgtgtgggtg atgtagggat       60
ggacatggcc cgggccatgg ggactcgaag ggagtgatgg tcctgccagc ggtgccacct      120
cttcctcacg gctgagcgca cctgtgggga aggcagaggc tcagctggct cccagggacc      180
aaccctgggc ttctgggacc atcccctcct ctgctttctg ctctcatggg tcgactgcca      240
ccctcatgac aaggaactgt ctgcttccaa acaggtcct  tccctgatgc tgttgcctct      300
ctccaggggc ctcttcctta tccttttcct ggagaagctt gactccacac ctcctttact      360
ccacactgtc ctcccagatc atccagtttc ctctggacac actgccttcc cttccctgac      420
tcactctgcc acctcaaaat tagcatcttg ggaccagaga gcgcagcttg gagacttggc      480
```

-continued

```
cccctcagcc ttcttgggcc cctgctcctt gcagggcgtt ggtggtgtgc gcccagctca      540
cacacctggt gcgcctcctc ctccctcctg aagaccgtcc cctctgcacc cctccacctt      600
ctctacctcc tgctagactc ccctgcctga ctaaccatgg catttactgc ctgaaaggga      660
aagctctctg tcttggtcat ttctaaagtt ggctctaccc ggtgccattt aagcttcatt      720
tgtttggtaa ttgaattttt ttggaaattg gatggtgtct ctcacatcct agcttgcaca      780
tggttcgaac agaataaatg ctccataaac atcccttgtt tgtttgcctt actggccccc      840
tctcttcttc tcatccagcc cacaggaccc gtctctgctg atggactttg caagtggaat      900
gtgctatcat ccacagagac acaggcctgc atagacacct cgccagtgcc ctgtgcagag      960
acaggcaagt gtattcctct ggagtgttcg gaagctccca ggccctaggg gctgtgtctg     1020
ctctttgctc catgtcctca tccacccag cccaggtacg agtgcgcttc ttccctgcgt     1080
cagctgcact ggggctttgg gcctcatgat tggcttgcac atgccaagct tcacggccgc     1140
ctgactcccc agagcctgct cttggtgtgt gggcttttct gtggcaggta gcgggggaat     1200
gtgctggtct ctcttctgct ccctgagtcc atacagacct gattgcttgg cacacatctc     1260
tttctggaag cttccttctg tcaccactc tgctctggct tctctcttcc atgaggccct      1320
gcggcctggg cttccttgct cacccagctc tgagtgcaca tgtggggtgc tggcatgtta     1380
tttcggggct gcatagttga ccttctaaac tggctccagc ccctgtgaga aggattcctg     1440
ttcccctaag gccgggtggt atctcaaggc ttcctctccc tggcactcca gcaaggccgg     1500
gcagcaccaa tggagctgcc ctggagtggg gtctgaggac ctggatatcc caggccaccc     1560
cgagggccca gcttcatacc tctccattga agaagcagta aagacagac acgaagaaac     1620 cctggaaagg agggaaagga gggagtggtc agtgacctac ctgcggagct gttctgcctg     1680
gtggggtggc actggggaca agatggtggg gggggacaa tttgacccag gaacccctgg     1740
agtcagagct gggtggggtc ctagcctcag ggtgcagata ttccacggtc cactctgagt     1800
gagcagtggt cacaggcctg gagccaggca gactccggtc tcctcaatat tgtgtgacct     1860
gtcccagggc atttggttgg gctgcctgca tcctcagaac aggtgctggg acagtaggtg     1920
cgggctggta ggatgaagac ccaggctggg atggggataa ctggccaggc tcaggctgag     1980
catgtacggg cttctaactc tgtggatgta actgagccat gggtgtgcca gtcccacggg     2040 accccttag tgagggcatg gctgccagag cagcctcagg aaagctcact gtggggcccc      2100
catctggtca caggccccac ctggaacgac tgcaggaagg agttgaaata gatgaacatg     2160
atctgtgaca ggtcgtcctc cccgggattg acgaagaaga gcatgtaggt gatgcccagg     2220
aggggcagga gcaccagggt ggccttcact gccttcctgg gggcgagagg tggacacagg     2280
tctgagccca tgcggcaggc agggcctcac ccagtgggcg gcgggagaca gtggtggtgt     2340
ttcttccggg agcttgagcg agctccctgg gtgaggcctg gggcagaggg ctctgccagg     2400 aagcagggg acgcccgat gacctcctcc tgtccccatt gtggggtcaa ggaccccct      2460 cacatacctg tactggattg tctcggatgt ggtggacgcg cgtaactttg tcattaggat     2520
cctgacgatg ttgaacagaa atacgaaatt gatctggagg gagggcgggc atgggaaaga     2580
gggaaaagga aggagcacgt gtttgagatg agccgagagg cagccccctt ccccgcagac     2640
ccctggaaac cgatgtccca cgcacacacc tatcctacct gtcccctag cacctgccag      2700 catcccaagg cctgtgctcc tccctcgcca ggatggggag acagccccat tttccagggc     2760
ctgtgtctcc agcccaggac tgaggaggaa aggtggcagc ctctgtgggt cgtgaccgag     2820
agcacggggc atgccctctg aggctgagaa agccccaac cctctcccca gtatagggac      2880
```

```
cctatgggag ccccttccc ctcactgcca cggggtccct acttgttgac tgcggggctc    2940
tctgagtccc ttgcactgtc actggctcta ggtcggcctg aggtccttct gactgaggac    3000
agcactgcca tggtggggcg acaaggcca gatggaggga ttaagaactc agttgccgaa     3060
tgagtgatta atctgccagc atcccacccc tgtgcccagg aactccagag ccttcgtagg    3120
caccctagac agggaagatg gatgggctgt ggggctggct ctgaggcccc aggaagggcc    3180
tcatttatct tcattctgag ttttccctca gcaccagagc ctccccaccc agcacctggc    3240
cctggaactg gcctgtgtgg ctccccagct gctccctgct gggtgtgggt cccatgggc    3300 ctgcgagtgt ctgttcatct gtattggctg tgactatgac tgtgttgtcc cctgggagct    3360
gcagtgtggg tctgtgggtc tatcctttaa gcacttgtgc aagtgtgttt gcctcacaga    3420
gcgtgtgcat gtgtgagcat ggatctgggg cccgggcaca tctgcgtttc tcttcacctg    3480
cctccgagca taggcaggca ggcaggcaag ggagtgtgtg tcggcctgac acagtggggc    3540
tgtttcctga caaagtgctc gtgggccaga gggagacaca tgttagccca ggggtgtctg    3600
ctggctcgtg tgcacacacc cactcacaca cacacacaca cacacacaca cctctgacac    3660
tctgtcaaga aaatccattg cttcttaagc ttgggctggg cccttctaac cctcccaagt    3720
tctgaatcct ggctgggaga ggagggacac aggatacaga cagatatcct gagactgtca    3780
acctgtagcc tctggatgct ccccacaagc tttcgggtag ccctaggggc agggagagct    3840
cacaccccac ctcagccact gtctactgct ctcttaccac atagtggtat ggcctggggg    3900
tcccagggag ggctggggat ggaaagcctt cagcgggggct gccatgacct gatacccca     3960 gctttctcct agggctcacc taatttccag ctcctgggtc tctggcatat tccctggat     4020 catgggacac aagtcacctt aacatataag tgaatcctaa ttttctcata caagtaatac    4080
aaagtatttg acctttctg attcttccgg acttccctga gagtagaaac tgttggaatc     4140
aaaatatatt ctcatttctg ccacattttc ttgaattcaa tattaatctt ccaacatcca    4200
tcaacccact aatcaattca attatccacc cactttattc atctatccat ctatccactt    4260
acctaccaac cagttcattc atttacccac ctacttttat ccatccgtcc atccatccat    4320
ccatccagcc attcatccat tcatccttcc ttccttccat ccatccatcc atctacccaa    4380
caaccaattc attcaattat ccacctactg ttttatctat ccatccacgt acccatccat    4440
ctacccatcc atctacctac ccaataacca atccattcag ttatccacct actcttttat    4500
ctgcccatcc actggcccat ccgtctatcc attcatctac ctagcaacca aggccttgtc    4560
tccatcctta cacttggcag acatttagtt atgtggcccc actcatctca gcttgggtct    4620
atgtaacctg aaaatccttc tttcctttga gcctgtttcc cagcctcccc cttcacacca    4680
ccacaggtac cttcctctct ctccagggag ccttctggtc accctgccca cactgagctc    4740
tccggctttc cattcttgga ctctacctcc ctgctaaaaa cacactccag ttctttagta    4800
agaactgtct attgtaccct gccctcgttc agcctgtttc tggttttatt taattgttca    4860
ttcattcaat gaatcaatgg accatgtgtc aggctctgag ccaggcatca gcgatggcga    4920
agtggacagg cagtcacagc ccctgcttgc agagggcttg tggcctagct gggggcctgg    4980
aggggttggg ggtgggggag atgacatctt tcctaaggtg tcaaaagac ctggagaaat     5040 ggcagatggg ctaagaactg aagatgaggc cccctccca aatgaactga agcaccaagt     5100
cctagtctca tggctcaaat tttgactgtt ccaatttgca gttgtgtggc cttgggtaag    5160
ttgcttaacc tcatgagctc ctgcttcctt gtctgcccc gaggggccta accacagagc     5220
```

```
ttgccttaga agatcagcat gggctgaaat agtcacagag accactaaga cctgtgtctg    5280
gcctagtgac tgccaatcct ttcccatgac accaacaatg acaacaccag caagaagtca    5340
ggcttcctgc aaattcaacc acctgattca cttctcagaa ccagaaataa gtgagtgtct    5400
cttagcagca gaaatgcagc tgtgagctgc tggggagtgt agggatggca ggaacaccaa    5460
acacgtgtcc aacctcgagg acaacaggca gatggtgggg acaaagcagg agacctgcct    5520
ttgagcctct gctctgctag ctattagtgg tgaccttggg caagccactt catctctctc    5580
agcttcttcc tctgtaaaat ggagagcata accctacttc ttttaggact tgagcatgca    5640
agggttggaa ataatgtaga tagagcttct ggaagggctc agcttggaat gtggaagccc    5700
ctgttggtgc aaagagctgg gcccaaagga aagaaggaaa gggctcgtga gcacagacgc    5760
aggggtggag ccagagaatg ggtctggaag aggaagcatg gagctgggtc ttgacactga    5820
gctcttgcgt tcctcgcctc cctttctctt ggcatttcct caccacccct ccaacatctt    5880
tacagttggg gcttactctt tgccaccatt ggtcccccat ccaggccagc cttccttggc    5940
tcagttccag gctcatcaaa agccttattc ctccaggatg gcccttggca gctggttggg    6000
agggaaagga tctcatgggg tttccataca cactgagggg tgagtgactc actgcagctg    6060
ggagtccaag gacaatccta ctagctgctg acaaaacctg gcttctgcct ctgaagcgaa    6120
ccaagccctg acggtggaat ttccagcagt gggtgaaaaa ccttcctagt cttcatcagt    6180
tcacatatat caaggacact ccaaagatgg aggtcaaatg aaacccgaag tcacagaaaa    6240
aggagagtaa gaaaataaaa gagataaata ataattgtct ccaaggtaga caaaagaaag    6300
ccccaccagg caccttctgt gtgcaggagg agatggcact ctcgctgagt ctcccagaag    6360
gaactgtggc cctttaagga agctggtaca tacaggagcc tgaaattact gagcctgaaa    6420
taagtcttac gtaaatgcca atttcttacg gggcttttt gtatgtcttt ctttctttat    6480
ctctctctct ttttttaaa ggtatgatat ataatgggtt ccttttgcag aatgcagcct    6540
ctacttgaac tctctcttaa ttaaagctca ttgtggatta aagatgtgtg gcaattatac    6600
cttagatgca aatacatttg gcaaagggca gggagctgga caaggaacaa ttcctcatta    6660
tgctgcatcc cggtattcac cgcttcaggc tgggggtggt gggctggacc tggagagggt    6720
cactgggggc tgaggggaac gtaggtctgg aatgaacaga agcccgcaca ctcttctctt    6780
gtcaccagct gcctgctcac ctggctttct cagcattgta cagtgtcaga ccgggagggc    6840
acaggaagtc tacccatcag atcctttctc ctcccagaga aagagccctg aggtcagcag    6900
agtggtgcag ggctgcgcca gggcatcgag catgaggaag ggaaggccgg gtggtgctgg    6960
ggcacagggt ggcatggaca gggtacgggg gtggcatata gagtgtgtgc gcagggctgc    7020
ccatgccaca tctttcccag cgtctctgcc tgggtgggcc ctcttctgtc ctcttggcac    7080
ccagccccat cccagccacc gctgagggct taccaggagc acgagaatga tggggccttg    7140
gtagatgtag tccaccaggt cgccaggctc cttgccaaac cagcacctgt gaagatgggg    7200
tggctgtagg gggcctcctg agctggaact gggggacccc cacagacttg gcccagggt    7260 cctccagctt tacccttcct gagacccaat ctccaggact gccccttccc agaaagcctt    7320
ggtggaaata ccagctccac tgaccaccct tacccaccag gctgtctttt gctctacatg    7380
gtgggtctga tctccccagc ccgactgagg acaggccatg ggtctctttc tcctcctctt    7440
ttacctgccc cattgcagac tgctaggcat aggactgggc atgcaggagg cacaggaata    7500
aagggagagc tgggctcccc cttgctggcc cagggccaat tgccttaggc cacctgttcc    7560
catattgctt gaaacccgct gttccgtgtg ccaggcactc actcggccac acaaagcagc    7620
```

```
agatgtggaa gtggagcctt cctacctcca gcctgggatt ttgcgtctttt gagccaatgc   7680 ttgtgcaccc agtgaggggga gctgctgcct ggctggcctc actggctgcc agaggcataa   7740
ttcattctcc ggggatgctg gtcaggggaa atgctttagg gtctgggtcg ccagcaact    7800 actggaccac agggaggggc catcaacttt ggggaactca ttcctctgaa atcttggagg   7860
tcatccagtg cagacctgcc tcagatagga ttctccctgt ctcccaggt ttctggcctc    7920 tgcttggagc cctcctttga caggaagctc accacctacc aaggcagccc tcttcttggg   7980
cagcttttac tcttcctaat gttgagctcc tggaactcta ctccattctt               8040
gcccccactc tgagaacaga tccctctgc tctctccagg ctctgagaca gacccttgg     8100 agatttgcat acaggctaat gttccctggt cccgctgct tcagctggt gacacctgac    8160 tttctggctg ctccttggct gacccatggc cagagttgct gtcatttggg ctgtggctca   8220
gcatattaca gcctctggca tagggagaac ctcaggatgg gacactgcac ccaggcagag   8280
actgagactt cagaaaaaaa aacaagctct gttaaatgct catggactct ttaaatgctc   8340
atggacagct ctggatgtca tgtgcggcct tggccccttc cacataccc gggccagagc    8400 tgccacatcc aagtctgagg aggccttaca aagaccaaag gggtcatgcg ttgggtcggg   8460
gggcacttca aggaaccaca attcctaact taattcagca aagttccttg agccctacca   8520
tgtgagtacc tctgagtgca ggactatttt tttcaattta aggacaacag gaacgtggat   8580
ctgtctaggt gtggctacaa ttcctgctcc acggcttggc cagagcccaa ggctgacctg   8640
tcctaacacc cccattccct tccccatgac cccccatgcc tggcccatcc acttactgtt   8700
cattctcata gtagagcttg ccgatggccc aggcgacgat gatggggaag ggatgcctg    8760 aaagaaggaa agacttgggc tgcaggggac agatggacag ggactttctt gtaggacata   8820
ccgtggggta ccacaacagg gctaggatca tgttttact cttccaacag caggccaccc    8880 acaacccag gggtgccctg tccctcaaca cctggcccat gccctgccc ctctctccaa     8940 gcagggctgc gtgattttgt gatagagaag tagagccagc cagtttctga gccagagaca   9000
aaggcctttg acaggtcct tcctggcagg gggagaagag ctatttgagg aatatccttt    9060
ggagagatcc tttgcttgtt cctcaccagc atggagggaa gtagctgcat ccaccggact   9120
gcgctggggg tggagggcag ggccaggctc tggtccttgg acccaagacg aagggaaatg   9180
gcctggtgag aagtcctccc cccaactagg ccctgctgcc cctgggaccc tcacaccatc   9240
cgatgaagag gaagaggcac ttgcgcaggc gctcagtgga gtaggtcatg acaatggccg   9300
tgtgcaggta gcagccttcc acaaacatcc agaagaagtt ggtcaccacg aagtagttga   9360
agatggtggt gatgcagcgg caccagacct gtgtgcaggg cagagaggct gtcaggaggc   9420
agcttggggc ccaggtagga catacccatc cccaggcagg gcaacaagac acagggctcc   9480
ccaaaggggg ttcgtggaca tgccatcaaa taccagcgaa cctcactctg aaaagcttca   9540
tccttctcca gtgctctttc acactttcag attaagttaa ggtgccattc tccactgggg   9600
ccaacgtgtt tttttaact tctctctaac tcttctaat ttttcattct agtaaagaga     9660
gcaagagtct ggctctgagc tttctgtagg cagaggctgg aattcaacca tcttgttgtg   9720
ttttcatttt agtttttttg agtcattttc aatccatagc aagtcagacc tgcttccttt   9780
tggggatggg atatggaatt tcatttagaa aaaaatgaaa aaataaaagt gagtaaagtg   9840
agtcaagggt gtatgaagtg gggctgcggc caggagggg attctccaaa gactctgggt    9900
ttgggaactt ctggacttgg cacaattatt actagctctg gagggagact tgcaaagtac   9960
```

-continued

```
acggccccg gcaagtcact gcacctctct gaacctcaaa aagtaaccct gccttccagg    10020
gtggttgaag gagatagagg atggcaaaga caggcatgag ggtagctgtg ttgtggctgt    10080
ggttgtgcct gctgtggttc cgtgccttcc cagcagaggg gaatgtgtcc ctgtccctct    10140
gagcaaggcc acccttcccc aggcaccaag gctaccttcc caaaggaggc agggagggga    10200
agaccctgcc cctttagagc cacgcagtgg gccatggcag ggccagggtc tagacattgg    10260
gcttccaggc cagagctcct ctcaacagac cccacctggt catcttcccc acaggctcat    10320
ccccagggca ccctgagagc caaggctggg acatggggaa tgatggagcc agctcaaggt    10380
ccggggagct gtgcgtcagg ggctctgctt ctgcacacag cccatcctct ctgtctggct    10440
ctgacagccc cagttctcag ataaccctcc tgtgctgagc tgttggctgc ttctgggctt    10500
ccctgcacag tccctgtggc tggctgtctc ctttttctg agaaagtcct gctgaggtgg    10560
gaagctacca agcccctcct cccaaccta cttttcatcc agggttgatg atgttctatt    10620
agcacaagcc cacgttggag ctagaaggca ccctcaactc gagtgaacct gtttgattct    10680
gaggcagtgt tctatgtggg accatgttaa ggatcacacc aggctggtgt ctgctcaggc    10740
acaggccacc caaaggaaat gtactgagaa gtctctgtcg gtgtgccaca gggctctgtg    10800
atggcccaag actagtctac agttttacaa tagcttggac acagtacaca gcaatggaca    10860
gaaatccaga gtggacagtt agcatgtggg atagccccct atgtagaggt atcatcactg    10920
catgtgacct tggcgagtca cttaacctct gtgagtctca gtttccatgt ctatgtaatg    10980
gggaaaatga tccctgctgg tctcattagg attaagtgag agaaagctca acagaggtta    11040
gttctagctt cctttctca aagggtctt tgagggcacc tgaatccaca agatgaggag    11100
tggactagga taaatgtgtc tagagtcagc tttgtgaagc tcccagcctg gcagcttcct    11160
gctcctccca gcccagctct gttgggacaa tggctagggt ggaggtgagc tcaggtctgg    11220
ttttgcacct gagccacagc ccagatgaca gcattctggc catgggtcag ccaaggagca    11280
gccagaaagt cagttgtcac cagctgagag tagcagggac tggtgaacat cagtctctgt    11340
gtgcaaatct ccaaggggtc tgtctcagag cctggagaga gcagagggga tctgttctca    11400
gagtgggggc aagaatgggg tggagttgca gaagttcaac attaggaaga gcttgtaaga    11460
gtaaaagctg ctcaagaaga agagggctgc tttagcaggt agtgagcttc ctgacaaagg    11520
aggggtccaa gcagagacca gacagacaga tgggtgcccc cggagcccag agccccccag    11580
gtatagcccc gagtctcccc gagcaatgac ctcattgctc tcgtgcactt catggtcaac    11640
gagctgcagc aggaaccaca tgacatttcg caggataaag gtggtgatga ggttccagtg    11700
aatcacattc cgcagacagc gaatgctcct gtgggaggtg caggtcaggg gtcagccagg    11760
ttcagggtc aactgggact gggttccccc tgaggccagg tagagactca gcctgggatg    11820
agggcagggc tgcactagga gccacttccc acccatggtg ccacagttgg gcctctgag    11880
tccagctccc actctgcacc ccacatgcct gctggtgatt catgccctgg caccccaccc    11940
aaacccccact ttctccacgg gcccttttat ctgctgggcc ccagaatgga ggtgagaatg    12000
tctgggagag gtgaaggggg tgctgtaggg ggagggatga ggagaaagca aggcggaagg    12060
gcagactcac cgcagggcca ggaaaagcag gaaggcggcc accagggctg ccacagatac    12120
gcagtggccc aggtagttga cgacaaggc gatgcggtag tgcaggtcat acttcctctg    12180
ctggacagac agacatgggc agggcagatg gaggcatggg cacgtgggggg tggggctggg    12240
tattccagcc gtggccacct ctgtgtcctg accttggggg cagaagtgct ccaggtgtca    12300
ttgccgtgcc tggctcttag ggttcgttcc tgttggccct gggtggctct tgttgttata    12360
```

```
aatggctgtg gtcaggcctt ccaacatgca tttattttta ttttttttaga gatggggtat   12420 cactctgttg cccaagctgg ggtccagtgg ctattcacag gtgtgatcac agtgcaccgc   12480
agccttgatc tgcaggcctg aagcaatcct cccacctcag cctctgaagt agctgggact   12540
acagacaagt gccactgtgc ctggcaccaa catgcatttt tgggggcaca ttttgagagg   12600
tatgggtaca gattcttttt taaaattcta ggctctagaa tgcttctcct gagtttagtc   12660
tcagcccgga tcccagctgg ctgagtgact gagggtgagt cgatttttat ttctggacct   12720 cagtttttgat gtctatacaa tggggccaac ctgccatcct acctaagaag caatggccta   12780
tgggaggcct ggggtggggt gcattgagat tagtctgccc tggagaccac acgaggggggt   12840 gcactgtcta tagagaattt agaaattcta ttcaaaactga ataaaagtca gttgacttttt   12900 aattatcacc aagtgttggc aatttgaaac aaagttagtg atgaaatact ccttcctgcc   12960
agggagagcc acccctccac cctacccaac ccctgtgttg attctccact gctggagggg   13020
cagagagagt ggaggtgagg accaagggct ggaggccccc ctgcccattg agtggcctcc   13080
ctgcagaacc cctgtggctc acattttgca gaatcacttt tcagggcgg gtgaatgttt   13140 ttccctctca atttggactt catctggggc aaagtcccag ccccactgag gactatgctg   13200
ggtaatgagg aggggatgga gctgagatgt atcctttcag gtcaggaatg aggcgtagcc   13260
tcaaggagag gagttcggtg cctcagcagc actgaattga attccagagc gagagctgga   13320
gcagggctcc agagaggcag agcaggaccc agcttctcat ggggacagcc cttgggggggc   13380 tgcatttgtt tccatgtgga gtcacagaat cagaatgcca gatggggaaa ctgaggccca   13440
gagggagagg aaggtgtgca gtcacacaac ccctaagatg ttaggagcat tgattacacg   13500
gttattccct ttttgtgtca catgccacct tggctttgtc ctctagcagc caagctctc   13560 ttgaaggtag gactccatgt ccccttctc tactccccta cagtgtcact aagcacaggg   13620
caggacactg ggggcagggg caggaggtac agaaggggagt gactgggtga caaaaggact   13680 ggtctgccccc ccttgggatc ttctctgctc aacctgagtc caaatacctg tgtgaggcct   13740
ggggtcacag caggtgaggg ccactcacct tgtcatccaa aatgggctca cactgtgagt   13800
agttgatctt tgaggcccac gtcccattct ccaagcattc tcgataggca ttccctacaa   13860
aaaatgccaa ctgccaagag tcaggtcact ccctcctca agaaccctcc ctggctccct   13920
ggtgcccaca ggataaggtg tacgcacctc agctctccta gggcagcaaa tacaatgtgc   13980
atctgaaagt ttacatgtaa gtcacttatg tgaaaatagc acaaaaggct catcttacaa   14040
aatagctaaa ggcatgctaa aacccatttt agacacaatc tttgactagc attttgtaca   14100 cttttcatttt gttcatttgc ttcaaaactg aatccaactg tgaggagtgg ttgtgcctg   14160 aagattcact gctttcagca tgccacataa tttacatcct tgtctcaatt gttttatatt   14220
tatgaggtcc atacttcacc aatatcagca cttccatttt tataatagct accatttata   14280
tagcatatgt ttcccatgta ccacttcctc ttctaactgc tatggatata catgtcaatt   14340
caatctccac aaccatccca tgaaggaggc attaatatga acccatttca aagaggagga   14400
aactgaggca taaagagatt aagctactgg ccaaggatac aaagatgaca agaggattca   14460
aactcagaag ttgtgcttc gggtcttctg ttcttaacct ttaggccata tcaagtagtg   14520
gcaaacagga atgagtgaat gctggggact cagggctggg ccaccgccct cgggctgctg   14580
ctgcctggga ggctaccacg agatgtttct aaatgttcaa gaaccagcct ctgtatttaa   14640
gttggaacat gatttaagtg tgaaaagaca tttcaagcag caatgtcctg tgcacaaaag   14700
```

```
tgcaggtttt gtcaaggggg aaggtaggaa agttaaaaaa tgctcacatt tgcctttctc    14760
tctatctcag ctccaactgt caaggtctgg ctcctaagcc accccctcca tacaccagct    14820
ccaatcagga ggaagccctc ccacctgaga aggcccggag ctctcgaagc ctgcctctgc    14880
ttggccttca tcactagtgt gtttctgacc taccgggtgg gttacaaatg ctgaacgttc    14940
cattgtttgg gggtgatttg taccagggtt cagctctctg actaatgggc agttgtctgt    15000
gaatttttct ttctagcata tgttagatgt acaatgtaaa gctaattaaa ataaatagct    15060
tgcagagcac agagttgcag agctggaggg ggaaccttag gttgtttttg gaagcagtgt    15120
gttctgaaat aattaagtta cttaaaaacc cacttccgtt gagcccgatg agttggaagc    15180
aatggaattg ggaaggagca cttgccgaag agcaaaatca atggggaaga ttctattagc    15240
ttaattgttt tttagtttgg tgcctggagc tcatccattc ttcaaaccca gggacgtgac    15300
tggcctattc cttcctcctg ggccaaggcc catccctggc agggccctgc catcccctg     15360 ccaagtgagt cagggaatgc cctggtctga tgctgattct gactctcagg aagaggaagc    15420
ctgctcccca cccctagcca tggcgcccaa ctccccaggt gggatctaat ttgataccta    15480
gcactatctt tccttaccaa cattcgtgct catgaaagag aaaggttacc tcaactcgtg    15540
agggtcagtg atagtgatgt cactgaacta aaaaagcaaa agtatgtaag gagggtaagt    15600
tcttttgtga aatgaacagt ccctccctga tgggggttta cggtgcctct gaacagtcta    15660
tgtgaggtga ggcagaccag gatcctgcct gtgcttcaaa gggcagaaaa atttatcttc    15720
tatatgttca tagatattat ccagctttcc tgaagctcag tgctaggccc cttccttcag    15780
gaagacctcc ttgattgctt ctactctata gctctctctc tcctgagcac ctccagtcct    15840
gaccgcctga gccccacact ccagcccttg ccccatgacc agcctggagc tgtctaggtg    15900
agtgagtctg gtcactctga tcaatgtggg ggctccctga ggacagggcc ttggaatact    15960
tgtttcccga atatgatatc tcatggtggc actgatcatg gggtgggctt gcaggtggga    16020
gggggtcagg atagaaatgc tgcaaatcag agacctttcc tctccctcac accaatgccc    16080
atggggtccc aagttccatg gattctgtct cctccttttc ttttttccaga gtcaactccc    16140 ctcctgccca tccctccatc tgctctctag tcttcttgcc tgggctgcta caacagcctc    16200
ctctcctctt gcctccctgc ttctttttctt gccaccttga ccatgttgat ttctgcttaa    16260
agccatcagt ggctctttat tgtgctcaag aataaagtcc aatttcttag catgatagtc    16320
aaggcccttg acacccaggt cccagcctaa ctgtcctgac ccatctccag cattctacat    16380
ggccactggc attggcacac ataggtttgg cacataccct ctttgtgtgg atccaccact    16440
taaagcacct cctccttctt acccactgct cacggatgaa ctcctaccca tctttaaccc    16500
cacactcaaa tgccgcctcc tgcatggagc catcccgac acccttaggt ctgaagcagt     16560
cctttctttg tttcctcctc tatcccttcc cttctcttgt aacgtagttt ttccacttta    16620
ttgcccttga accacaataa cacatacatt ttatgttata atccagtaca cacacacaca    16680
cacaaacaca gaatccagct gtactatttt cctttccagc ctattctaat gtcttctatt    16740
catttcacac acactgatca tgacccacta aattgactcc acagtccact cttgtgtcac    16800
aatccatagt ttgaaaaata caaattctgt tttagtgcat ttgccataat tcactatgaa    16860
cttcatctct ttggacctaa tccttctttt ctttgctact ggacttgagc tccttgggga    16920
tagacaagta agtagaagcc atattggagc caccatatct ccctcaggac agagccattg    16980
aggaaatgtc ggctgaacag aattgactca gacctgctga ccctgggaa agcaggtggg      17040 atgcagaagc gggaggggac ttccctctct ggcagcccag ccctgcctgc agatgagctt    17100
```

```
ctggttacag acactgggta tcaaaggact ggaggataga tgtgcccac  tcttcagggg   17160 agctgtctgc tgtggccaat gagggcactg ggccctcagg cacagcctcg acaggaggg   17220 agtaagacag aaagaatctc atccaccccg tgggaaacgt agacggatgg gcacacactc   17280
tgagggctga tggcaaggct agaattgtgg ggctggatgc agagaggtgg gtgcccatta   17340
ccatagcaac acaggtgccc ctgctgagga tcagtgctga tgatgtggag tgtgggcttc   17400 cagggcatt  agggtctgaa tgatgcaggc agggtcttct cttgcaggac tctgtagtct   17460
gggaggcctg gtttccatgc ccagagtggc ccaggcctgc caaaaacccc cattacaatg   17520
ggctctcccc gtttcagatg ctgacacttt gcaaagagtt cctggttcag gcagttacct   17580
ggggtggtcc tgaagcctgg ctgggacatg agaccctata ttctagctgt agttttgtct   17640
ctagatagct aggtgaccat gactaagccc cttccctctt ggtctcagtt ttgcctctta   17700
gaaatattac agtaaattga ttctctatga tgttattggc atctcaggtg gatcaattat   17760
atgttatgtg agactcccca gtctactaaa tgccagttag caccctcaag ctattgtgac   17820
aactccaagc atcctgacat caccatcaaa tggttggcac ttctatctct gatacttct   17880 ggaaagacat ggaccatagg agacagggac catgagggac tactttggt  ggtagttttg   17940 ggggaaggag tacaagggac aggggtaggc atggggaaaa gagttaatgg gactgtggta   18000
aggcacaaca atgggtcat  tggctatttg caaagaaaag acaggaagt  gagggagagg   18060 ctggatatgg tggctcatgc ctgtaatccc aacattttgg gagaccaagg caggtgaatt   18120
gcttgagccc aagagtttga aactagcctg agcaacatga tgaaacccca tctctcaaaa   18180
aaaaaaaaaa aaaaaaaaat agccaggcgt ggtggtgtgc gcctgtagtc tcagctactc   18240
agaaggctga agtgagagaa ttgcttgagc ctggaggca  gaggttgtgg tgagctgaga   18300
ttgtgccact gcactccagc ctgggtgaca gagtgagacc ctgtgatgat gatgatgatg   18360
atgatgatga tgatgatgat gataatgatg atgatgatag aagaagaagg aggatgaaga   18420
ggaggaggag gaggagaaga agaagaggta gtactagtag tagtagtggt ggtgagggag   18480
agaaggtgat gacattgagg tggggagggc cagaagcaat atttacagaa ggaatgaagt   18540
cactacatgg gatcggaact ttcagcaccg cggacagcac aactccattc ttcatccctg   18600
cctatctcta aggttgggga cctcggagag ctcctaagaa ccagccttcc cacccgatat   18660
tccgaccttg gccatgggcc cagcccattg aggtcaagct aattcatgcc ccttttcaag   18720
gcccagctcc agccccagct cctccaggta gtttccatga ctgttccagc tccccaaggg   18780
tccagctgct tgtgactgcc tggctcatgc taggctggga ttgatctttc actgacccct   18840
ataaaggtgt tgtactttcc taaccagccc aggttctctg gagcagaagt ttaccttatt   18900
ttgtacaagg ctgagagcct ctaaaggcat gtcctgggtt gctgtcatct ctggccttt   18960 cttaagcact gcacagagct gagcacacag gatctcagga tggaccaaag ctgatgctgt   19020
ttcctaggtt acttgggaac tcattgaagg taggaggctc agagtgggcc aggaggacag   19080
tctgccacct tgtatgccca tgcttcacca agatgcatgg caaatacaaa acagtcacac   19140
atacatgcag gaggaagcaa ggtctcacac aaagacacca tgggtaggct gacccagctg   19200
ccaaaactgc agacattgca gtccaacccc acatggggga ggggtgtcag tctcaaacag   19260
caaacctgtg ggcagcattc tccaggttcc tggcatgaaa gctttgactg ttccaaggga   19320
agcaagttgg aaactgagtt atcaggcatc tccttgggaa ttaggaagga agacaacttc   19380
tgcatttggt ctggtgggac cagaagagag aaactgacac atctgggtc  actcaaccat   19440
```

```
gaagaggcag aagatctctc tcccttggga cacgcttcct cacgggagac cctggagttg   19500
gtgtacctag gagagacaga ctctccctgt gaccctgtgt ttcagcagat gcagccagtt   19560
atgccacctc ttcagtgtca ttaccacttg gtgtccagat cctcagaaga gaataccttg   19620
ggggccagat atcccaccct cagttccctt tactgcctgt agttgggcca ctccagatcc   19680
agccatcttc ttgtctggcc tggggcctag ttgagaaatc tttgaccatg actttgagtc   19740
accttctta cctactttt tttttttga tgggggtct cactctgtca cccaggttgg      19800
ggggcagtgg tgtgatctta gctcactgca gccttgaact cctatactca agtgatcctc   19860
ctgcctcagc ctcctgagta atgggactac aggcatgtgc caccatgcca tgatcatttg   19920
ttatttttt gtttgttttg tagaaacggg gtctcactat gtggttttgg ctggtctcaa    19980
actcctggcc tcaagtgatc ctcctgcctc agctcccaa aatgttggga ttgcaggcat    20040
gagccaccat gcctggccat ctttcttgct ttctgtggga aaaacctctc aatcaatgtc   20100
tcctcccagc ttggcctcca cttcctgagg tggattgctt ttcatcccca gttaagagac   20160
ttttggggaa ggtggacaga gctgggggtgg tcagacgtac agtcctagta ctaacagcat  20220
ggttttcctg agcttcccaa acgaggtgca tctccttgag tcagcatcct gcattgcttg   20280
gaggccactg caggttaagg aggactgacc aactttgagg cccacctggc atatttctgt   20340
cttgatccga tcacagcaaa ttggtggtca gaggggaaca ggcagctggt gatgttcacc   20400
caagctcaga cccagactga cgtagaagtg ctagattgag tttgggagtc taatattgcc   20460
aaccccagcc actgggtggg aaaggcatcc ccagggccct ttgctggtgc tgtctgggat   20520
tcaggccagg gaacttggat tccatttctt agtgttatat ggacacagct ctctgagcct   20580
cgactgcctg ttctggacct tcagagaccc tcaactccct atttccacag gacttttcac   20640
tcatggtgcc ctgccatcct taagcaggac ctgtaagcac acttacagga gacagtgggg   20700
aaactgagtc atagaggcac tgagcagttt aatggagacc atactgggtc tatgaaaaag   20760
ggaaggggga gtggaaccca gctcactgtg taagctctgc cctccccaga gagggcagt    20820
gggaggaggc ccctacctca tgctcccgcc tctactgtac agggctccct ccttccagcc   20880
atcctagcaa cactcagtgg gctcgtcgcc atgacgccag cctgtggagg aaagtgggga   20940
ggggaccaac acaggacccc tgtggcagaa gctgccttgg aactgagaaa catcactaga   21000
actcatcaag ccctccaccc acctggtgca gatgaactga ggtctgaaga ggggagacca   21060
cctgcccaaa gggagaaaag cagtcagtag gatggccggg attagatctg gctctcagtt   21120
cctagttcct atgaagtaat gcaggagaa acagctggc tggcaggatg ccagcagcat    21180
ccctccaggg gggcaagggg ctgcctttct ctacaggctt ttaggtacca gaccttctca   21240
atctagatag acagaatcct ccctcccagg acatccccag aagccacaga gttctggggg  21300
ctctcagaga tagcaggaga ccaccacccc agaatgagga tagccattct tggtgtgagc   21360
aggatttccc ctacccaagg acatgatggc ccctccttcc aggccccagg ccaccttcaa   21420
ctcccctccc cttgctgaca atgccttagc tgtctacagg gagccccaag cagcatcatc   21480
tccctgtgt gccatggccc cacgaggtca gcatgttctc tgtccccttc acacagataa    21540
gaaaactggg acttggacaa ggagggcctg ccagtccctc agtgagtcat ggcaaaccca   21600
ggacttagat ccagccctgc taaatctgag cccaggttcc tcccactctc ccttgcccca   21660
gctgctctcc tggcaggtgc tgtgtgtgaa agggaccgcc tgcctgactc tgaagcacct   21720
ggtgagggtg gcagtcaga ggggcccaaa tgcctgtacc tggggcccag ccaagaagcc    21780
ctgtggggag ctccctgagg atcactgaga tgggctcct ccttcagccc gtcttcaggg    21840
```

```
ctccaggctc tgctgtggca ctggtggtaa ggagtgcaca gggaaggatg ctgggacctc    21900
tgacttaagg agcaggtggg aggagaggaa agggccaagg cccaggtccc cagccagccc    21960
ttgattgaga tttagatggc acattttgaa aagcagtatc cttccagagt attctggtcc    22020
tgtgccatag ggctacggac aagcagccgc tgtctctaaa gccagcagaa tcgaggccca    22080
tgccctggtc caacatttga ggcctccatg atctggctta ttcttccctc cctcctcttc    22140
cacttccgct cccaccctcc cttccatctg acacatcatt agctcaattt ttcaaggcac    22200
tgttcaacaa cacttcctcc atgaagtctt ccaaatttac tttcccttac tcttggaata    22260
actcccttcc atgtgctctg actgtcttca ctgtgctatt ttacttggga gcctatatca    22320
aaaagttctc tttgagagtc tgcctgtctg tcactcttcc tagaacagga gcccctggaa    22380
ggcaggctca ggtcttatgc atctttgaaa agcttgtctc taggctcctc aattctttct    22440
gggggaaagg gtaaaatact cagaacccca ataaggggtg agcctgagca agacgatcag    22500
gtggctggag gattcctggg gagagcagga gacaggaaag atcaagatgc atgcagaggt    22560
gggtagaagc tagagcagaa gccaggagtt cccagagcca gcagaggcct atcagggccc    22620
agacttgctg tagaactctg agcagctgtg tttccctctc ctggccagtc atttcctacc    22680
cttaagtggg gaggggaagg ctggactcgg aacatagagc gctctgcagc cgggcagctc    22740
tggggtgtct ggatggccac aagggcatcc acttctgctc tatttctctt ccttccttct    22800
tttcttagct aaacctctgt gatggccatg cctgtcccac cttccctctc tcccagcagg    22860
gaagttgttc tcacacatgg agtaacttgt ggcccttgga gaatgaaata gagtcagggg    22920
ggatcaggtc tcgctggagt ctgagaatgc agacctgagt ttccggattt acagcttcta    22980
cttcttcaac ccagagggca gggtctatct ggggtcctcc tgaggcttgc accectgcac    23040 tgcgcctgtc cttaacaaat gtggcatccc aactgctcca agacctttaa agtttacccc    23100
cactccctcc agaaagcctc ccaggaatgt cccagtgtcc accaagcccc tcttcccgat    23160
ctctgactgt tgatttgcac aagcctcctt gataagcagc ctggggcttc ctgagggcag    23220
gtctcagcct ttcttatcac ctctgactct tagggctgaa gaagggattc ctgcataagc    23280
aggcagaccc aatgggagag acccctctgg ctggagacca ctcagcttat gtgtttccat    23340
tgtaacacaa tcagtgctta agcatgtctc tagaatgggg ttctgggaag tggggacccc    23400
taacctcccc atgtggctag gttagatggg atgccccttc ttcccctgtc ctggcagatg    23460
cctcagtaca gatgaccccca gccattccca gtaggacatt gcggagcttg aggtcaagga    23520
ggctgaggct cagccaagct gcacttagtg gttccacaga aggaaaatgg accatggcca    23580
ggagggaggt ggcaagaccc tcctttgcag ccaaaaggac cgtagggaca ggcaagatga    23640
ggtgcaggag gagggcagat agaaggaggg atgggagtgg ggagacagtg ggtttggaga    23700
tggagtcggg ggatgaagaa ggcagtaggg agagatggag aaagagagag agaggtagaa    23760
aatgagagaa tctgagaaag acagaaacat acacccagaa acagaaccac acatagagaa    23820
aatcagaaac agacagggag acaatgagag agacacagag acagagatgt acacacagag    23880
atgggctcag aggagtccgt gtggaatggg gagaggtggg aggaaaatgg aatataagtg    23940
ccccacttct ggccaaacca cttccatgct aatccactte ctttcggcct acagacaggg    24000
agacaggccc acaaaaggga tgagacttgc cccaattaaa ttgtatatgg acatttagga    24060
ttgtttctag ccacccagga tttgaacctg ggttcggaga atcctggggt aagaccgagg    24120
ctacctcccc gcctagagct aaaatgccag atccttactt cccaggatcc cttgtagcca    24180
```

```
gagctttggc atgggatttg gggctccaca tattccccca cccatcagat gcacctaccc   24240
gagggaatta gtgaactgga ggcccccaga tggagacagg gagaaagcct ctccagagat   24300
aactgcagga agcttaagac tccaggttgg ccaggtgcag tggctcacgc ctatactccc   24360
agcactttgg gagccagaga caggaggatc gcttgagtct gggagttcaa gaccagctct   24420
ggcaaaatgg caagatccca actctacaaa aaatttaaaa attagccagg tgtggtggca   24480
tgtgcctgca gtctcagcta ctcgggaggc tgaggcagga ggattgcttg ggcacaggag   24540
tttgagattg cagtgatctt tgatcatgcc actagtggtg ccagggctg tggtgttgg    24600 cagggccttt cagggagagg gaggtcccct cacagggcca gctctgccct gtgttcttgg   24660 cttgggccc caaatctggt tctctagccc actcagtgat tccataagct ccccaatatc    24720
tttttaaaaa atttcttctc tgcttaacct agcagagttg cttttttgaaa ggcagcagaa  24780 cctgggtttg aatccttgtt ctgttacaag tgacttcatt gctccacacc tcagtttccc   24840
catgtgtaaa atgaggataa tgccatgtct ctgtcactcg atggtgcaag gattaaatga   24900
gttaaaccac agtacaaaca tgtggaagct cagccactga agcgccagca caggttgtgt   24960
agagaacacc caaggagact cgtgtgctta acttggctct gccactgact aacatgtgtg   25020
gccatgcgct agtcccttcc cttcccttgg ccctgctgca tctggaaata actctgggta   25080
agatggctca aggctctgac ccagcctccc aaactcacac actgtagcta tttgctaacc   25140
ccacatcctg aggacttcta aacgccttat ctccactctt ggtgctctct tgagcttttc   25200
ccccacccaa ccagctgctt cctgaacatc tccactcagc tgtccctcca gctcctcaaa   25260
gtcaacacat ccccaactgt gctcagctgt ttcctgtgtg cccaaccttt accttgccat   25320
ctctcaccat atcttgtcaa tttcaaatgc ccaaggttgc tggcgtcttc aacctcattt   25380
gctcttacag cctgcggtct acctgggtct gtgcagaaat ccccttactt ctccttcccc   25440
tccagaggac agtgtgctcc caaaattgag cttctctgct cacaagctca cccaggctcc   25500
ctctccagat ggtgaagccc tgtagaatgc cctgcatcac ctgacctcca tgcccctccc   25560
cagcctcatt gtttctttct cctactccct gttctccata caacacactc ctcccaaggc   25620
acaaagccca gcctgtctcc ttgcctttgc tcagtcccct cagcctagag ggcctctcct   25680
gtgcctatta cactcacctg ctaaaatcca acctgtcccc agaagtccag ctcagagggc   25740
taagtcctcc ctgatcctcc aggccggagg tatgagtctt ctttccaaac ctctaagctc   25800
tcctcgcaaa ccgaatgcct cttgtggagg gagtactgcc ccatggttaa tagcgagggc   25860
tgtggattca cctgcctgca ctggtgcata ggagctgatt aggactttca ataagttact   25920
tcatgtgtct gagactcagt gttcttgcct gcaatatggg cataaaagca gtatgtatct   25980
cagagggagt gtgggcgagt gggattatgg atgcctgaga tatggataca aagctctctc   26040
agtggtagct ggcacctgga aaatgatcaa cacttagctt tgtggcagat tctctgtgct   26100
cagctgagtt gaaaaatcgc agagactaat atctaaactg ctatcccac ccgggcgatt    26160 cctgctctct aaggaatgag gcttcaatgc gggtttggct atagcataac aaaattgggg   26220
caggaagtga agcctgaacg ctcctgttct tcccctaggc ttctcgtgga ggtttctccc   26280
tctgtcattc tttttaaagg aaggatccca aggaaaaggc aaacagagaa gcaggaagca   26340
gcactgatgt gaagaaaggg gaggagggaa atcaatcatg catttccaca gccattagca   26400
gcctctgctc ttcccaccta ggctgacctc acacccccagg tgctggttag tggtaagtgc   26460
tccccaccct ccacaagctc ctctcattct ccagcagttg cagtgcaggc agcactttgg   26520
tctaaatgaa gaaaattgtt cattagatac caggggctaa ttggccctac ttttaccagc   26580
```

```
ctgggtggtg ccccaacctt ttatcagctt ctcattagac ttaattgata tgaatggcct    26640
gatatgtgct gtctgcagca cctttgggaa gtcttccttg tcaccccgcc cccacacccc    26700
aatcccatag accttgtgct tcccccctaa ttagggcatt catcattctg ttcttttttgt   26760 ctgttgcaat tgtgagtgag agcctcaata cagtgcctgt gcagtggctg cacatagtg    26820 ggtattccac aaattgactg agtattactg tactcagctt ggctatgaag aagagaccca    26880
ggccctggga aggggggggcc cccaggctgg tcggggagaa caaggcatag cccaggctgg    26940
ggtaagaacg aaagcagagc tccctgaggt tcacaggctg tgggctgaga tgctccatca    27000
ccccacttta ccctggatgg cccttaatct ccgggcccag tctgaatcag gcatgctgat    27060
ctccattgcc ccaccccaca cagctcacgg aatcctaaaa atacagtttt ataaggtcag    27120
gactaggaag gcacagggaa atcattcctt ctgcttgcac acctcctagc ttggggatct    27180
tacttccttc tagggagatc tgttttaatc atggatggga agcatgtgct ccctgggccc    27240
accagagccc tcagctggtg cagccaggag agtgcggctt ggcatcaggt gcaggtacat    27300
ctctcttgcc ttctaaccat ctctcatggc aaagccctca gcctcagctt ctgaaagctt    27360
gtgtgtgtgt gtgtgtgtgt gtgtgtgtgt gtgtgtatgt gtggtggagg tggagctggg    27420
ctaccaatca gacacagaca ctctgaggat gttttccagga tgagaggctt cagacaaaca    27480
atccagatag ggtctcagcg tgcttgacaa ctggggtccg gctggagata tcaggggggt    27540
tctaggtggg gcagtgattg ctgccccac agcctcccgc agaccacaca cctggctccc    27600
atcccatgtt ccagggca cagacaggca cctacccaca cgcacacacc cagaacccac    27660
actgaacgac cccacctgga ggctgtgtaa ctccagcaac ctctactgcc cttttcccca    27720
gagcctcaag ccagtccatg atttgccagg aggaaggcag gcacaggttg ttctccttga    27780
gagatggtgt tggggtgctg attcagacac cactcattat gggggcgcag gaataatgct    27840
gcccacagcc cctgactcag cccagcaggt cagtcctggg acctcggatt agggaagatg    27900
caacaccccg caccctctgg cttagcagaa cctacgcctg catgtcctcc ccacgaaaca    27960
tgcgctcgcc ccagccctcc tgcctcctac cctcctcctc ccctctggta gtagggtctg    28020
gtcactgcac tcactctggg ggatttggga cttagcatat ccgccctcct gggataggtc    28080
cccctcctgg gcagggggaag cattgtctaa acaatgaagc cctaatgggg aacttcaggc    28140
aacgggaacc tacaatgagg gaaggaggtt tacactccaa gaggaggaag tatttccttc    28200 tcccctttttt gggctgtcac cgcatggagc acgggaattg tgggcaaatc actggcttac    28260
tgagattaga cgctgtattg ggggtagaag cagaaggcgc gcccccaaca ctgtaagggg    28320
tccttaacgc ccgcggtccg cggtaccgcg gccgtcagca gctttgtacc gctgggtccg    28380
gaatcctctt tactccctaa accgccttct caggaggccg gtgtagagca ggcagcgagg    28440
gccgggggca ctcacgggtc gtgttgtact tgacgccgtt gaagtactcg ggcacggcc    28500 tctccacgag ggctccggca gcgctgcggg gccagcacgt tccgatctgg tccaaggtcg    28560
tgttgcagta ggagtaggga cctggcggcg ggagagagcg cagtagggct cagaggggcc    28620
cgcagggacg cggggctctc ggagcgcggg gtcagggggcg cacccagcgc gcgagagaag    28680
gagcccgcgc agcctccgac cgctcgcctc ccgcctaccc tcggggtcca ggggtggccc    28740
ccagccgtcc aagagcagct cttcagccag cgccaggctg cagttggcct ccagcaggct    28800
gtggagcagt gccgcgtcca tcgcgtcccg cagccgcgtg cggagaggga gtgggagtgc    28860
gcgcccggcg tgactgcgag ggagtggacg cgagagtgag cggccgagag ggcgcggggt    28920
```

```
cctggccccc gccagcccag ccccgatctc ccgggcagcc tttgggcgcc acctccggtc    28980
gcccagagct gtcaagtggg gaccttcccg gagaggagcc gccgagtgca cggagctgcg    29040
ggtacagccg ctccgccgcg gccaatggct gcgccggggg gcggggccgg gcggctcctc    29100 tcggagggc tcagtctcca gcccccgggc cctccaccct gcccaaagta cggcttctca    29160
gttcgcagct ctcttccact cgcggcgtcc agaggagggc ggtgggctgg agagcgtggg    29220
cctggggtga cggaatgctc tgtgcgggga tcgcaggccc ccgagctgca gggggcagca    29280
aagcgcgccc acctgcccgc ctgcccgagg agaacaccgc agctctgcta atcgagggac    29340
agccgcaacc caaagttcgg cagctttccg cctgagcttc cctccctga gcgaggacac    29400 tggagggagg cagagacgga gagcccatgg gcagatctgc atcctccaaa agcctccata    29460
gcctctggga aggaaatgta tcgaggaggc ctggagggaa gcaggagac acccatgagt    29520 ctaatgagat caagtggcct gagtgggttg aagtccttgg atcagaccgt ggaagctgga    29580
atggagagag atttcggagg ggcagccaga cctggtgagg aggaactgga gtgggtggct    29640
ggttttaagt aggagcccag aggcagggat aacatcaggt ctcctgcttg agtgactggg    29700
tggccattta atcagatgga gtaagtctag gggagaaatt ggctgaaatt atctggaagg    29760
ctttatacac ccagttgtta gtgccttggg caccagaaag aataaaggaa gaagtgagaa    29820
tgtgtctctc ttcctcaagg cttgggcagg gcttcacctg accctggttt ccacaccagt    29880
agcggggcag gggcggggag aatcaggccc cacagcaggt gtggaggagc tggaaacctc    29940
cccagagaac ttgcccaggc cccccacccc accctggccc agaatgcctc cttggtgatc    30000
tgctgtggct gcaccctcag agtgcccagg gcgggcctgc tgtgtctgcc agctgagtgg    30060
ggcattgggc tcgggaagca gggcctgggg taaggcatgc ttccactcag gctgcatttt    30120
ggtccagcct ctgactctgc tctccctgcc atggtacccc aggcaggatg cttgccctct    30180 cttctgggagc tttctccatc agtgaaatct tccccgaggc ccctctcagc tctgagactc    30240
tctggttctg agttatgaga cggagagtct ggggaagaca tacatgtgtg ttgtgtgttg    30300 tttgttttcta tctttagagg gcaaggagag ctggaaccta gtctcagaaa ccagtcctgt    30360
tcccctgcca tcctccacat aaacctaagc tgctaggaaa ggctgaaacc accatgaact    30420
agcaccatgc cctgggcaga gagaggcaaa gcagcaggca ggctgctttt gtgtgctccg    30480
ctctcaccag cctccatatt aatggtgctg tcactgccca ggcagagcga gtgagaccac    30540
actaagacca gggctgagcc ctggaatctc tccaggggcct gctgactggc aggaacaaga    30600
tgctgagcag ccagccaggt ctaccctctg cctcctgaat ggacagtgag agcccaggct    30660
cagctctggg cagctgcaga ggtagaggtt ccttggtctt catattatcc agtgccagga    30720
gcaggggagg acctaggcag agtcctaccc tccgctccta gactgagccc tgttacccag    30780
ggtcccacac aggccagagg gtggctggcc aggtcagccc atgtattcac agggcaatag    30840
tgtccctcat atacaaggga tagcccttca cacagcacgg tgcagcacag aggaagggag    30900
aaatcctaag ccaagcttaa gttattatcc ttgttcatta ctgcagccac cacctaggtg    30960
gtgcctaaag cacctataga tgcagctatg tcaagaggtg gtgtgctccc aatgaccaga    31020
ggccagggac ttctcatctc atgcagattt ctgcagaaca gagggttggc ctgggtgaac    31080
tggattgctc ttaactggga gagctcacat accaaagatt cttctgggaa gtgaccattt    31140
cagtggcaga gtcaaaggct gttctgcatc ctgaatgagc agttggggtc tgagcacata    31200
cccacagacc cacagacccg aggtcccctg gatgtgggc catttcttca tggatcttat    31260
tattataggc acagttgtca ttcgagatgt gacagaggga aaactagaaa aggtagcagt    31320
```

```
ttgggaacaa attgatttta cagctcactt tagtgtctgc aaacaggcaa atgaggaaga      31380
aattgggaag agccccaaaa ttccctcaat tttactaaat ccaagtacaa acaaacaaag      31440 acagggcat ttttgctaac taaagaagca gaggtagatt agaggctttg ggatagtgat       31500
gggttcccag cgctgcaggc cagccccatc ccagctggag gccaggaatt aggggataag      31560
tatttggaac agtttgtgtg tccccaagct gttggggaca ggttggcaaa taggttcagg      31620
gaagtgtgac aggtactttg aagacccct gtgtaccatg agcagcagag taaggcaggt       31680
gcctctggtg ccctgcatcc catcccatgg cccacctctg atgtcagctg cagcagcagt      31740
ggacagttcc aggccagctc agacacactt gcaaagccta atacatggca tcaaacaggc      31800
atgtaggcac aacagaatca cacacagagc cacagttatg catcttcacc atgcacacac      31860
attctctctc taattcatcc cctaccactc aaatgtcagc tggaaaacag gatttaaagg      31920
gacaggatgc atctttgctt ctctaaggga ctgtccttgg ttagactaca tagagaggga      31980
gtctattcag gcacagctgg aatagtcgtg gtgtttcctg ggaattacga cggggttgct      32040
gagggcacag aggttccaga gggccctgaa ggtgctgcac ttttgccctg tagcactgga      32100 gacagggtc ccaggccagg cacccctcc tcacccctatc ctactccact gcaggacaga      32160
ggaattggcc tggtgtcttc atgtcaaacc atgggactaa gctgtgggga cagaaaggac      32220
tctcagtgac atccaatccc acattcttgt tttacagatg gacaatagga ttcccagaca      32280
agcaaaagag gtttccctcc cttacttctc ccaggccatc ctcatctctg cagcagccca      32340
aatgggctcc ctgtctcctc atggcagata aaacgatgtt ttataattac gatcctgtca      32400
ctcttcctca taggagtgcc gccaacccat tgcccttgag atggagacca cctctttggt      32460
attgcaaaga aggtccttcg taatcatcta tccctcatcc tcaccttct gctccatttg       32520 aaaggccctc cagaacaaca tgtcattcct gggaaccatc tttggtattg caaagaaggt      32580
tcttcatgat catcgtcccc catcctcacc ctcctgcttc atttgaaagg ccctccagaa      32640
caatgtgtca ctaccagaaa ccattcgcta tctctgttcc ttgtttgtat ttctgcactg      32700
gaaatggcct tacagctcca cactcatcct tcagacatgc agctccttgg tgaccccatc      32760
tgctgggtgc tggcctatgt cacatccagg ttgcttttta ttcattgtct catctaccag      32820
cccatgcctc cccaagggca gggctggtcc tggttcacta acccatcccc agcacccatt      32880
ggaatgctct agacttcagc ccagtgagtc actaagaaag gacagatacc ttggcagaag      32940
agctgaggaa agcccaggtc cctgtcttca ggccaaggct ctcttcccat                 32990
```

```
<210> SEQ ID NO 14
<211> LENGTH: 644
<212> TYPE: DNA
<213> ORGANISM: mus musculus
<220> FEATURE:
<221> NAME/KEY: CDS
<222> LOCATION: (213)..(521)

<400> SEQUENCE: 14
gcggcccctc agctccgcga gccccgcggc ttctcttggc aaggtcctgg ggtgatcgat       60
caattgcgga gccccgaagc tgcccgactg gccggggtgg gcggggagga gcctggacgc      120
tgcactctct ggctgctcct cgtcgcgccc gctcccctcgc agccacgcgg ggcgcgcact    180
cccactccct ctgcgcgcgg ctccggggcg ca atg gac gcg gcg ctg ctc ctc      233
                                   Met Asp Ala Ala Leu Leu Leu
                                    1               5 agc ctg ctg gag gcc caa ctg cag cct ggc gct ggc cga aga gct gct       281
Ser Leu Leu Glu Ala Gln Leu Gln Pro Gly Ala Gly Arg Arg Ala Ala
```

```
                    10                  15                  20
cct gga cgg ctg ggg agt gcc ccc gga ccc cga agg tcc cta cac cta       329
Pro Gly Arg Leu Gly Ser Ala Pro Gly Pro Arg Arg Ser Leu His Leu
 25                  30                  35 ctg caa cac gac ctt gga cca gat cgg gac ctg ctg gcc aca gag cgc       377
Leu Gln His Asp Leu Gly Pro Asp Arg Asp Leu Leu Ala Thr Glu Arg
 40                  45                  50                  55 acc cgg agc cct agt aga gag acc gtg ccc cga gta ctt caa tgg cat       425
Thr Arg Ser Pro Ser Arg Glu Thr Val Pro Arg Val Leu Gln Trp His
                 60                  65                  70 caa gta caa cac gac ccg gaa tgc cta cag aga gtg cct gga gaa cgg       473
Gln Val Gln His Asp Pro Glu Cys Leu Gln Arg Val Pro Gly Glu Arg
                 75                  80                  85 gac ctg ggc ctc aag ggt caa cta ctc aca ctg cga acc cat ttt gga       521
Asp Leu Gly Leu Lys Gly Gln Leu Leu Thr Leu Arg Thr His Phe Gly
 90                  95                 100 tgacaaggag tatccgctgc ctgaggaatg tgatccactg gaactcatca ccaccttcat     581
tctgagaaac atcgcgtggt tcctgctgca actcatcgac cacgaagtgc acgagggcaa     641
tga                                                                   644

<210> SEQ ID NO 15
<211> LENGTH: 103
<212> TYPE: PRT
<213> ORGANISM: mus musculus

<400> SEQUENCE: 15

Met Asp Ala Ala Leu Leu Ser Leu Leu Glu Ala Gln Leu Gln Pro
 1               5                  10                  15

Gly Ala Gly Arg Arg Ala Ala Pro Gly Arg Leu Gly Ser Ala Pro Gly
                 20                  25                  30

Pro Arg Arg Ser Leu His Leu Leu Gln His Asp Leu Gly Pro Asp Arg
             35                  40                  45

Asp Leu Leu Ala Thr Glu Arg Thr Arg Ser Pro Ser Arg Glu Thr Val
 50                  55                  60

Pro Arg Val Leu Gln Trp His Gln Val Gln His Asp Pro Glu Cys Leu
 65                  70                  75                  80

Gln Arg Val Pro Gly Glu Arg Asp Leu Gly Leu Lys Gly Gln Leu Leu
                 85                  90                  95

Thr Leu Arg Thr His Phe Gly
            100

<210> SEQ ID NO 16
<211> LENGTH: 20
<212> TYPE: DNA
<213> ORGANISM: synthetic

<400> SEQUENCE: 16
ccccgaagct gcccgactgg                                                  20

<210> SEQ ID NO 17
<211> LENGTH: 24
<212> TYPE: DNA
<213> ORGANISM: synthetic

<400> SEQUENCE: 17
ggaaggctgt aaaggatgga gaag                                             24
```

ISOLATED SOLUBLE CORTICOTROPIN RELEASING FACTOR RECEPTOR TYPE 2 (SCRFR2)

This application claims priority to provisional U.S. Patent Application No. 60/650,866, filed Feb. 8, 2005, which is incorporated herein by reference in its entirety.

The United States Government owns rights in present invention pursuant to grant number DK 26741 from the NIDDK.

I. TECHNICAL FIELD

The present invention is directed generally to method and compositions related to molecular biology, neurology, and endocrinology. In certain aspects it is directed to compositions comprising and methods of using soluble G-protein coupled receptors (sGPCRs) as modulators of GPCR activity and/or modulators of the pharmacologic effects of the ligands that bind such soluble GPCRs.

II. BACKGROUND OF THE INVENTION

Receptors, in general, are molecular structures located in the cell membrane or within a cell that form a weak, reversible bond with an agent such as an antigen, hormone, or neurotransmitter. Each receptor is designed to bind with a specific agent(s). A specific family of receptors is the seven transmembrane ("7TM") or G-Protein-Coupled Receptor ("GPCR"). These receptors link with a Guanine Nucleotide-Binding G-protein ("G-protein") in order to signal when an appropriate agent has bound the receptor. When the G-protein binds with Guanine DiPhosphate ("GDP"), the G-protein is inactive, or in an "off position." Likewise, when the G-protein binds with Guanine TriPhosphate ("GTP"), the G-protein is active, or in an "on position" whereby activation of a biological response in a cell is mediated.

GPCRs share a common structural motif. All these receptors have seven sequences of between 22 to 24 hydrophobic amino acids that form seven alpha helices, each of which spans the membrane (i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracelluar loops" or "extracellular" regions). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular loops" or "intracellular" regions). The "carboxy" ("C") terminus of the receptor lies in the intracellular space within the cell, and the "amino" ("N") terminus of the receptor lies in the extracellular space outside of the cell.

Generally, when a ligand binds with the receptor and "activates" the receptor, there is a change in the conformation of the intracellular region that allows for coupling between the intracellular region and an intracellular "G-protein." It has been reported that GPCRs are "promiscuous" with respect to G-proteins, i.e., that a GPCR can interact with more than one G-protein (Kenakin, 1988). Although other G-proteins exist, currently, Gq, Gs, Gi, and Go are G-proteins that have been identified. Ligand-activated GPCR coupling with the G-protein begins a signaling cascade process or signal transduction. Under normal conditions, signal transduction ultimately results in cellular activation or cellular inhibition. It is thought that the third intracellular loop (IC-3) as well as the carboxy terminus of the receptor interact with the G-protein.

In general, the activity of almost every cell in the body is regulated by extracellular signals. A number of physiological events in humans as well as with a wide range of organisms use protein mediated transmembrane signaling via GPCRs. Signals from a specific GPCR cause activation of a G-protein in the cell. The majority of signals are transmitted by means of GPCRs into the cell interior. There are many varying aspects of this signaling process involving multiple receptor subtypes for GPCRs and their G-protein linked counterparts as well as a variety of linked intracellular secondary messengers. The signal transduction may result in an overall or partial activation or inactivation of an intracellular process or processes depending upon the proteins that are involved. Important signaling molecules or neurotransmitters which bind to GPCRs include, but are not limited to corticotropin releasing factor, parathyroid hormone, morphine, dopamine, histamine, 5-hydroxytrytamine, adenosine, calcitonin, gastric inhibitory peptide (GIP), glucagon, growth hormone-releasing hormone (GHRH), parathyroid hormone (PTH), PACAP, secretin, vasoactive intestinal polypeptide (VIP), diuretic hormone, EMR1, latrophilin, brain-specific angiogenesis inhibitor (BAI), cadherin, EGF, LAG, (CELSR), and other similar proteins or molecules.

GPCRs constitute a superfamily of proteins. There are currently over 2000 GPCRs reported in literature, which are divided into at least three families: rhodopsin-like family (family A), the calcitonin receptors (family B), and metabotropic glutamate family (family C) (Ji et al., 1998). The reported GPCRs include both characterized receptors and orphan receptors for which ligands have not yet been identified. (Wilson et al., 1999; Wilson et al., 1998; Marchese et al., 1999). Despite the large number of GPCRs, generally, each GPCR share a similar molecular structure. Each GPCR comprises a string of amino acid residues of various lengths. GPCRs lie within the cell membrane in seven distinct coils called transmembranes. The amino terminus of the GPCR lies outside the cell with the extracellular loops, while the carboxy-terminus lies inside the cell with the intracellular loops.

The ligands for GPCRs comprise small molecules as well as peptides and small proteins. The interactions between these ligands and their receptors vary from system to system but they may require the interaction with residues in several of the four extracellular domains and the N-terminus. In some instances the N-terminus alone may maintain an ability to interact with or bind ligands. GPCRs with known ligands have been associated with many diseases including multiple sclerosis, diabetes, rheumatoid arthritis, asthma, allergies, inflammatory bowel disease, several cancers, thyroid disorders, heart disease, retinitis pigmentosa, obesity, neurological disorders, osteoporosis, Human Immunodeficiency Virus ("HIV") infection and Acquired Immune Deficiency Syndrome ("AIDS") (Murphy et al., 2000; Mannstadt et al., 1999; Berger et al., 1999; Jacobson et al., 1997; Meij, 1996;).

Accordingly, there is a need in the art for methods of producing modulators of GPCRs and the ligands that bind GPCRs for use as therapeutics. These therapeutics may be used to prevent or treat GPCR associated diseases and/or disorders.

BRIEF SUMMARY OF THE INVENTION

The present invention is directed to compositions and methods related to a sGPCR ligand binding domains, as well as effects of the sGPCR on GPCR signaling and interaction between GPCR ligands and their GPCRs.

An embodiment of the invention includes an isolated soluble G-protein coupled receptor (sGPCR) ligand binding domain. A sGPCR comprises all or part of a GPCR extracellular domain. In one aspect of the invention the sGPCR is an soluble form of a GPCR family B member. In a further apsect the sGPCR is a GPCR subfamily B1 member. In still further aspects, a sGPCR is a soluble secretin receptor, $VPAC_1$ receptor, $VPAC_2$ receptor, $PAC_1$ receptor, glucagon receptor, growth hormone releasing hormone (GHRH) receptor, glucagon-related peptide 1 (GLP-1) receptor, glucagon-related peptide 2 (GLP-2) receptor, gastric inhibitory polypeptide (GIP) receptor, corticotropin releasing factor 1 (CRF1) receptor, cortisotropin releasing factor 2 (CRF2) receptor, parathyroid hormone 1 (PTH1) receptor, parathyroid hormone 2 (PTH2) receptor, calcitonin receptor-like receptor, or calcitoinin receptor. The sGPCR can be a soluble PTH1 receptor or PTH2 receptor. An embodiment of the invention also includes a sGPCR that is a soluble form of the corticotropin releasing factor receptor type 2α (sCRFR2α). The amino acid sequence of a sCRFR2α may comprise an amino acid sequence encoded by exons 3, 4, and 5 of the CRFR2α gene or does not contain exon 6 or greater. A recombinant sGPCR of the invention may include 75, 80, 85, 90, 95, 100, 105, 110, 115, 120, 130, 135, 140, 150, 155, 160, 180, 200 or more amino acids, including all ranges there between, of an GPCR extracellular domain(s), including all or part of the amino terminal extracellular domain. In certain apsects, a sGPCR ligand binding domain may comprise an amino acid sequence at least 70, 75, 80, 85, 90, 95, or 98% similar to 50, 75, 100, 125, 150 or more amino acids of SEQ ID NO:4 (sCRFR2α), SEQ ID NO:8 (sCRFR2β), SEQ ID NO:12 (sCRFR2γ), or SEQ ID NO:15 (mCRFR2α). In a further aspect, a sCRFR comprises the amino acid sequence of SEQ ID NO:4, 8, 12, 15 or a combination thereof. In a still further aspect, the invention includes an isolated sGPCR further comprising an affinity tag, a label, a detectable or therapeutic chemical moiety, a biotin/avidin label, a radionuclide, a detectable or therapeutic enzyme, a fluorescent marker, a chemiluminescent marker, an immunoglobulin domain or any combination thereof. In one asepct, the GPCR comprises an immunoglobulin domain, in particular an Fc domain. The sGPCR can be conjugated to a polymer, which includes, but is not limited to polyethylene glycol (PEG).

Embodiments of the invention include polynucleotides encoding sGPCR of the invention. Polynucleotide may further comprise a promoter operably coupled to the polynucleotide encoding the sGPCR. The sGPCR encoding sequence can be included in an expression cassette. The expression cassette may be comprised in an expression vector. The expression vector may include, but is not limited to a linear nucleic acid, a plasmid expression vector, or a viral expression vector. In certain aspects, an expression vector is comprised in a delivery vector, which may include, but is not limited to a liposome, a polypeptide, a polycation, a lipid, a bacterium, or a virus.

Still further embodiments of the invention include methods of modulating the activity of G-protien coupled receptor (GPCR) comprising: a) contacting a target tissue with a sGPCR; and b) binding a GPCR ligand in the vicinity of the target tissue, wherein the activity of the GPCR in the tissue is modulated. The ligand can be a GPCR family B ligand, a GPCR subfamily B1 ligand. In certain aspects the ligand is a corticotropin releasing factor (CRF), urocortin 1, urocortin 2, usorcortin 3, stresscopin, parathyroid hormone, PTH-related hormone, TIP39, calcitonin, amylin, CGRP (CALCA and CALCB), adrenomedullin, secretin, VIP, PACAP, glucagon, GHRH, GLP-1, GLP-2, GIP or any combination thereof. The methods may also include contacting a target tissue comprising the steps of: a) preparing sGPCR ligand binding domain in an apprpriate pharmaceutical solution; and b) adminstering the pharmaceutical solution to an animal, human, subject, and/or patient in an amount to affect binding of a target ligand in the target tissue of the animal. Administration can be, but is not limited to ingestion, injection, endoscopy or perfusion. Injection includes, but is not limited to intravenous, intramuscular, subcutaneous, intradermal, intracranial or intraperitoneal injection. Disorders that may be treated, ameliorated, modulation, reduced in severity, include disorders resulting from hyperactivation of a GPCR or hypersecretion of GPCR ligand. In certain aspects the disorder is insulin sensitivity or type II diabetes. The disorder may also include an anxiety-related disorder; a mood disorder; a post-traumatic stress disorder; supranuclear palsy; immune suppression; drug or alcohol withdrawal symptoms; inflammatory disorders; pain; asthma; psoriasis and allergies; phobias; sleep disorders induced by stress; fibromyalgia; dysthemia; bipolar disorders; cyclothymia; fatigue syndrome; stress-induced headache; cancer; human immunodeficiency virus infections; neurodegenerative diseases; gastrointestinal diseases; eating disorders; hemorrhagic stress; stress-induced psychotic episodes; euthyroid sick syndrome; syndrome of inappropriate antidiarrhetic hormone; obesity; infertility; head traumas; spinal cord trauma; ischemic neuronal damage; excitotoxic neuronal damage; epilepsy; cardiovascular and heart related disorders; immune dysfunctions; muscular spasms; urinary incontinence; senile dementia of the Alzheimer's type; multiinfarct dementia; amyotrophic lateral sclerosis; chemical dependencies and addictions; psychosocial dwarfism, insulin hypersensitivity or hyposensitivity, hypoglycemia, skin disorders; or hair loss. In certain aspects the disorder is an anxiety-related disorder; a mood disorder; bipolar disorder; post-traumatic stress disorder; inflammatory disorder; chemical dependency and addiction; gastrointestinal disorder; or skin disorder. In a further aspect the anxiety-related disorder is generalized anxiety or the mood disorder is depression. In still a fruthre aspect the gastrointestinal disorder is irratable bowel syndrome.

Other embodiments of the invention include methods of detecting a GPCR ligand comprising: a) contacting a sample suspected of containing a GPCR ligand with a sGPCR polypeptide; and b) assessing the presence or absence of sGPCR polypeptide bound ligand. The methods may further comprise characterizing the bound ligand. Characterizing a bound ligand includes, but is not limited to various chromatographies, mass spectrometry, peptide sequencing and the like. The sGPCR polypeptide may or may not be operably coupled to a substrate or surface. The method can further comprise: c) adminstering a radiolabled GPCR ligand; and d) assessing binding or competition for binding of the radiolabeled GPCR ligand to the sGPCR. The GPCR ligand may include, but is not limited to corticotropin releasing factor (CRF), urocortin 1, urocortin 2, usorcortin 3, parathyroid hormone, PTH-related hormone, TIP39, calcitonin, amylin, CGRP (CALCA and CALCB), adrenomedullin, secretin, VIP, PACAP, glucagon, GHRH, GLP-1, GLP-2, or GIP.

Still other embodiments include methods of detecting a sGPCR comprising: a) contacting a sample suspected of containing a sGPCR with a ligand that binds the sGPCR or a related surface bound GPCR; and b) assessing binding of GPCR ligand with components of the sample. The method can further comprise characterizing the bound sGPCR, which can include chromatography, mass spectrometry, protein fragmentation and sequencing, and the like. A GPCR ligand may be operably coupled to a substrate or surface. The methods can further comprise: c) adminstering a radiolabled sGPCR; and d) assessing binding or competition for binding of the radiolabeled sGPCR to the GPCR ligand in the presence and absence of the sample being tested. Exemplary ligands include corticotropin releasing factor (CRF), urocortin 1, urocortin 2, usorcortin 3, parathyroid hormone, PTH-related hormone, TIP39, calcitonin, amylin, CGRP (CALCA and CALCB), adrenomedullin, secretin, VIP, PACAP, glucagon, GHRH, GLP-1, GLP-2, GIP or other know GPCR ligands.

In yet still another embodiment of the invention includes antibodies that specifically bind a sGPCR. In certain aspects an antibody may bind the amino terminus or carboxy terminus of the sGPCR. Aspects of the invention include an antibody that binds a carboxy terminal 5, 10, 15, 20 or more amino acid sequence, which may be derived from an alternative reading frame of a nucleotide sequence that encodes a transmembrane region of a GPCR (typically the result of alternative splicing and may be engineered into a recombinant polynucleotide of the invention).

Embodiments of the invention include methods of detecting the expression of a sGPCR, either using protein, nucleic acid or both protein and nucleic acid evaluation or assessment. Aspects of the invention include methods of detecting a sGPCR mRNA comprising: a) obtaining a nucleic acid sample to be analyzed; and b) assessing the presence of a sGPCR nucleic acid comprising a splice junction resulting in a sGPCR. The method may include assessing the presence of a particular species of mRNA by nucleic hybridization, nucleic acid amplification or other methods of analyzing nucleic acids. In a particular aspect a sGPCR is a soluble B type GPCR, a soluble B1 type GPCR, a soluble CRFR, a sCRFR1, a sCRFR2, or a sCRFR2α. A polynucleotide can include an exon/exon junction that includes the amino terminal amino acids of a GPCR and none or part of an exon encoding a portion of a transmembrane domain. In a particular aspect the splice junction of a sCRFR2α is an exon 5/exon 7 junction, wherein exon desigantion is based on the genomic designation of CRFR2 exons. Based on the CRFR2α transcript the exons would be designated 3 and 5, respectively (see FIG. 1 for an example).

A "soluble" GPCR (sGPCR) means a GPCR that comprises all or part of an extracellular domain of a receptor, but lacks all or part of one or more transmembrane domains which normally retains the full length receptor in the cell membrane, the soluble form is not integrated into the cell membrane. Thus, for example, when such a soluble receptor is produced recombinantly in a mammalian cell, it can be secreted frrom the recombinant host cell through the plasma membrane, rather than remaining at the surface of the cell. In general, a soluble receptor of the invention is soluble in an aqueous solution. However, under certain conditions, the receptor can be in the form of an inclusion body, which is readily solubilized by standard procedures. Such sGPCR may be derived from an engneered nucleic acid, a processed protein (e.g., protealized protein), a synthesized protein, or an isolated splice variant. A polynucleitide encoding such a sGPCR may be isolated or engineered.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the invention means that the isolated protein is substantially free of cellular material and includes preparations of protein having less than about 30%, 20%, 10%, 5% or less (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

So that the matter in which the above-recited features, advantages, and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIG. 2A is a schematic representation and the oligonucleotide primer locations of the amplified portion of mouse CRFR2α (upper panel) and sCRFR2α (lower panel) transcripts. The locations of the oligonuleotide primers, at exons three and seven, which result in the amplification of two products of 418 and 309 corresponding to CRFR2α and sCRFR2α, respectively, are indicated. FIG. 2B is a representative image of electrophoretic analysis of the semiquantitative RT-PCR for mCRFR2α and sCRFR2α mRNA and the ribosomal protein S16 mRNA (upper panels). Southern blot hybridization of amplified mCRFR2α and sCRFR2α cDNA and the ribosomal protein S16 cDNA fragments were also performed (lower panels). The radioactive bands were quantified by PhosphorImager and normalized values (relative to the S16 expression) are presented as relative densitometry units (FIG. 2C).

FIG. 3A is a western immunoblot of mouse sCRFR2α isolated from the medium of COS-M6 cells transiently transfected with sCRFR2αFLAG construct reacted with anti-sCRFR2α-(113-143) serum (left panel) or monoclonal M2 anti-FLAG (right panel). Lanes 1, 2, and 3 correspond to 0.1, 1.0, and 10 µl of sCRFR2α-FLAG extract, respectively. FIG. 3B, Displacement of [$^{125}$I]Tyr$^{113}$ sCRFR2α (aa 113-143) binding to rabbit anti-sCRFR2α (aa113-143) by synthetic sCRFR2α (aa 113-143) and by purified COS-M6 expressed sCRFR2α (aa 113-143)-FLAG. FIG. 3C, Immunofluorescence staining of COS-M6 cells transiently transfected with mouse sCRFR2α construct visualized with the anti-sCRFR2α (aa 113-143) serum followed by a Cy3-conjugated secondary antibody (FIG. 3C(b)). The slides were counterstained with DAPI to visualize both transfected and non transfected cells (FIG. 3C(a)). Cells incubated with normal rabbit serum (NRS), as negative control, followed by a Cy3-conjugated secondary antibody did not show any staining (FIG. 3C(c)).

FIGS. 4A-4F show immunoperoxidase staining for sCRFR2α in select mouse brain regions. Major sites of cellular expression included the principal output neurons of the olfactory bulb (FIG. 4A); the medial septal nucleus (FIG. 4B); and the basolateral (BLA), but not the central (CeA) nucleus of the amygdala (FIG. 4C); cerebral cortex, where stained cells were localized mainly in layers 5 and 2/3 (FIG. 4D); and red nucleus (FIG. 4E). In each of these sites, the pattern of cellular labeling was similar, though not necessarily identical, to that of CRFR1 mRNA expression. Immunolabeled fibers and varicosities were restricted to a handful of cell groups, including the paraventricular nucleus of the hypothalamus (PVH; FIG. 4F). FIG. 4G, sCRFR2α-like immunoreactivity in acid-extracted and partially purified tissue isolated from mouse brain was measured by radioimmunoassay. Tissue extracts were tested at 5-7 dose levels and displaced [$^{125}$I]-labeled Tyr$^{113}$ sCRFR2α (aa 113-143) binding to rabbit anti-sCRFR2α (aa 113-143) in a dose-dependent manner.

FIG. 5A shows activation of CRE-luciferase reporter by Ucn 1 or CRF, with or without sCRFR2α preincubation, in 293T cells transiently transfected with mouse CRFR2α. Luciferase reporter containing a fragment of the CRE promoter of the EVX1 gene was cotransfected into 293T cells with CRFR2α expression vectors. Luciferase activity was measured following treatment (4 h) with 0.0001-100 nM Ucn 1 or CRF, in the presence or absence of 0.1 nM sCRFR2α. Assays were normalized to cotransfected β-galactosidase activity. The representative means of six replicates from one experiment is shown in the graph. FIG. 5B, Equilibrated CATH.a cells were treated with Ucn 1 (10 nM) with or without sCRFR2α (0.4 or 4 nM). After 5 min of receptor stimulation, cell lysates were harvested and subjected to SDS-PAGE immunoblot analysis using phospho-ERK1/2-p42,44 antibody and ERK2-p44 antibody. The ERK activation was calculated by normalizing the levels of phosphorylated ERK1/2-p42,44 to total ERK2-p44. The representative of means of triplicates from one experiment is shown in the graph. *, P<0.05 vs. vehicle treatment, #, P<0.05 vs. Ucn 1 treatment, UD=undetected.

DETAILED DESCRIPTION OF THE INVENTION

Figure 1:
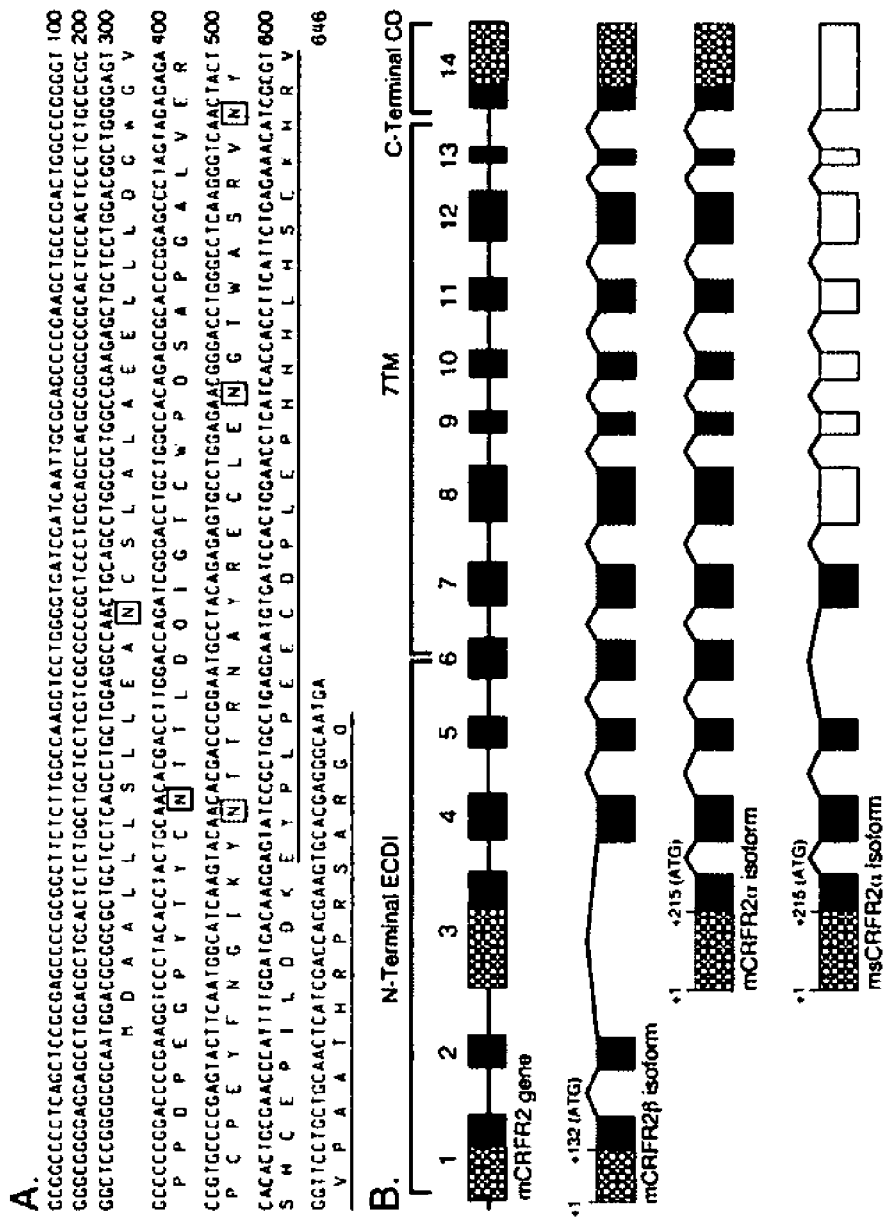
FIGS. 1A-1B. Illustrate an exemplary nucleotide and translated amino acid sequence of a soluble GPCR, the CRF receptor type 2α (sCRFR2α) (FIG. 1A, SEQ ID NO:14). Underlined amino acids indicate the unique C-terminal tail. Boxed residues indicate putative N-linked glycosylation sites. Schematic representation of the structure of the mouse CRFR2 gene (upper panel), the two known functional transcripts in mouse, α and β (middle panels) and the novel sCRFR2α splice variant (lower panel) (FIG. 1B). The locations of the translation start sites (ATG) are indicated. Exons coding for the N-terminal extracellular domain (ECD), the seven transmembrane domains (7TM), and the C-terminal cytoplasmic domain (CD) are indicated. 5' and 3'-UTRs are indicated by hatched boxes. Black boxes represent coding regions and open boxes represent exons downstream to the stop codon.

Useful therapeutic approaches for the treatment of diseases associated with GPCRs and associated signalling pathways include the inhibition or modulation of the activation or inhibition of the GPCR. One approach is the development of small molecule inhibitors, which are costly to develop and bring to market. A drawback of the treatment with small molecule inhibitors or antagonists of GPCRs is the risk of toxicity, particularly with repeated application. Also, many GPCRs have no small molecule receptor antagonists. The development of a GPCR anatagonist that is less costly and/or less toxic than small molecule inhibitors is worthwhile. Embodiments of the invention are directed to compositions and methods related to soluble GPCR (sGPCR) ligand binding domains, as well as its effects on GPCR signaling and interaction between GPCR ligands and their GPCRs. sGPCRs may be used to antagonize the activation or inhibition of GPCRs in vitro and/or in vivo.

I. G-Protein Couples Receptors (GPCRs)

GPCRs constitute a superfamily of proteins, which are divided into three families: rhodopsin-like family (family A), the calcitonin receptors (family B), and metabotropic glutamate family (family C) (Ji et al., 1998), each of which may further be divided into subfamilies. The reported GPCRs include both characterized receptors and orphan receptors, those for which ligands have not yet been identified (Wilson et al., 1999; Wilson et al., 1998; Marchese et al., 1999). Despite the large number of GPCRs, generally, each GPCR share a similar molecular structure. Each GPCR comprises a string of amino acid residues of various lengths. GPCRs lie within the cell membrane in seven distinct coils called transmembranes. The amino terminus of the GPCR is outside the cell as are the extracellular loops, while the carboxy-terminus is inside the cell with the intracellular loops.

GPCR family A (Rhodopsin like) includes, but is not limited to amine, peptide, hormone protein, rhodopsin, olfactory, prostanoid, nucleotide-like, cannabinoid, platelet activating factor, gonadotropin-releasing hormone, thyrotropin-releasing hormone and secretagogue, melatonin, viral, lysosphingolipid and LPA (EDG), leukotriene B4 receptor and other similar receptor proteins.

GPCR family B (Secretin like) includes, but is not limited to receptors for calcitonin, corticotropin releasing factor (CRF), gastric inhibitory peptide (GIP), glucagon, growth hormone-releasing hormone (GHRH), parathyroid hormone (PTH), pituitary adenylate cyclase-activating polypeptide (PACAP), secretin, vasoactive intestinal polypeptide (VIP), diuretic hormone, EMR1, latrophilin, brain-specific angiogenesis inhibitor (BAI), methuselah-like proteins (MTH), cadherin/EGF/LAG (CELSR), and other similar ligands. Harmar (2001) describes three subfamilies of GPCR family B, subfamily B1, B2 and B3.

Subfamily B1—Subfamily B1 includes, but is not limited to the classical hormone receptors, which are encoded by at least 15 genes in humans, with at least five putative members in *Drosophila* and three in *C. elegans*. The ligands for receptors in this family are polypeptide hormones of approximately 27-141 amino-acid residues; at least nine of the mammalian receptors respond to ligands that are structurally related to one another (glucagon, glucagon-like peptides (GLP-1, GLP-2), glucose-dependent insulinotropic polypeptide, secretin, vasoactive intestinal peptide (VIP), PACAP, and growth-hormone-releasing hormone (GHRH). All members of this subfamily have been shown to be capable of regulating intracellular concentrations of cAMP by coupling to adenylate cyclase through a stimulatory G protein (Gs). Some members of the subfamily are capable of signaling through additional G-protein-coupled signaling pathways, for example through activation of phospholipase C.

Subfamily B2—Subfamily B2 consists of a large number of family-B GPCRs with long extracellular amino termini, containing diverse structural elements linked to the core 7TM motif. The prototype members of this subfamily were an EGF-module-containing, mucin-like hormone receptor (EMR1) isolated from a human neuroectodermal cDNA library (Baud et al., 1995) and the leukocyte cell-surface antigen CD97 (Hamann et al., 1995). Subfamily B2 also includes the calcium-independent receptors for α-latrotoxin. Three genes encoding calcium-independent latrotoxin receptors (CL-1 CL-2 and CL-3) have been identified. Secondly, the brain-specific angiogenesis inhibitors 1, 2 and 3 (BAI1, BAI2, BAI3), a group of proteins that have been implicated in the vascularization of glioblastomas are also included in this subfamily. Thirdly, the protein encoded by the *Drosophila* gene flamingo and its orthologs in humans (the cadherin EGF LAG seven-pass G-type receptors Celsr1, Celsr2 and Celsr3) and in *C. elegans* (F15B9.7) is also included in the B2 subfamily. Finally, the subfamily includes a fourth, diverse group of receptors that contain some motifs common to receptors in subfamily B2 but are otherwise structurally unrelated (human epididymis 6 (HE6), EGF-TM7-latrophilin-related protein (ETL), the immunoglobulin-repeat-containing receptor Ig hepta, G-protein-coupled receptor 56 (GPR56) and very large G-protein-coupled receptor 1 (VLGR1)). Analysis of the sequenced human genome (1 Apr. 2001, UCSC Human Genome Project Working Draft (genome.ucsc.edu)) indicates that there are at least 18 human genes encoding members of subfamily B2, and there are at least four in *Drosophila* and three in *C. elegans*. The structure and functions of members of subfamily B2 have been reviewed recently by Stacey et al. (2000).

Subfamily B3—The prototype of a third group (subfamily B3) of family-B GPCRs is methuselah (mth), a gene isolated in a screen for single-gene mutations that extended average lifespan in *D. melanogaster* (Lin et al., 1998). The gene encodes a polypeptide that displays sequence similarity to other family-B GPCRs solely within the TM7 region. A least eight paralogs of methuselah are encoded within the *Drosophila* genome sequence.

The characteristic feature of all family-B GPCRs is the 7TM motif, which is distantly related to comparable regions of some other GPCR families but much more highly conserved within family B. Conserved cysteine residues within extracellular loops EC1 and EC2 probably form a disulphide bridge, by analogy with family-A GPCRs in which this feature is also conserved (Palczewski et al., 2000). In contrast to family-A GPCRs, however, many of which appear to rely on internal hydrophobic sequences for targeting to the plasma membrane, most family-B GPCRs appear to have an amino-terminal signal peptide. Studies using site-directed mutagenesis and the construction of chimeras between hormone receptors in family B have shown that the amino-terminal extracellular domain is essential for ligand binding but that the transmembrane domains and associated extracellular loop regions of the receptors provide information necessary for specific interaction with ligands. All of the hormone receptors in family B contain a conserved region within the amino-terminal extracellular domain close to TM1 that may play a role in ligand binding. Splice variation in this region of the PAC1 receptor has been shown to influence ligand-binding specificity and affinity (Dautzenberg et al., 1999).

Receptors in subfamily B2 contain a variety of additional structural motifs in their large amino-terminal extracellular domains that suggest a role for this domain in cell-cell adhesion and signaling. These include EGF domains (in Celsr1, Celsr2, Celsr3, EMR1, EMR2, EMR3, CD97 and Flamingo), laminin and cadherin repeats (in Flamingo and its human orthologs Celsr1, Celsr2 and Celsr3), olfactomedin-like domains (in the latrotoxin receptors), thrombospondin type 1 repeats (in BAI1, BAI2 and BAI3) and, in Ig hepta, an immunoglobulin C-2-type domain also found in fibroblast growth factor (FGF) receptor 2 and in the neural cell adhesion molecule L1. VLGR1 has two copies of a motif (Calx-beta) present in Na+-Ca2+exchangers and integrin subunit β4.

Family C (Metabotropic glutamate/pheromone) GPCR includes Metabotropic glutamate, calcium-sensing like, putative pheromone receptors, GABA-B, orphan GPRC5, orphan GPCR6, bride of sevenless proteins (BOSS), taste receptors (T1R) and other similar proteins.

In certain embodiments, the sGPCRs of the invention are class B receptors. In aspect, the sGPCRs of the invention are subfamily B1 receptors, and in a further aspect, the sGCPRs are CRFR1 and CRFR2, and parathyroid hormone receptor. Table 1 includes a non-limiting set of exemplary members of the GPCR family, accession numbers and associated UNI-GENE and OMIM entries are incorporated herein by reference as of the priority date and the date of filing of this application. Unigene entries can be accessed by internet links contained in OMIM webpage. Numerous other GPCRs and their accession numbers may be found at the website defined by the following address on the world wide web gpcr.org/7tm/htmls/entries.html.

TABLE 1

Exemplary GPCRs.

| GPCR description | Protein acc. #/mRNA ace #/ OMIM # (each of which are incorporated by reference) |
|---|---|
| BRAIN-SPECIFIC ANGIOGENESIS INHIBITOR 1 (BAI 1) | O14514/AB005297/602682 |
| BRAIN-SPECIFIC ANGIOGENESIS INHIBITOR 2 (BAI 2) | O60241/CR623649/602683 |
| BRAIN-SPECIFIC ANGIOGENESIS INHIBITOR 3 (KIAA0550a)(BAI 3) | O60242/AB005299/602684 |
| CALCITONIN RECEPTOR (CT-R, CALCR) | P30988/NM_001742/114131 |

TABLE 1-continued

Exemplary GPCRs.

| GPCR description | Protein acc. #/mRNA acc #/ OMIM # (each of which are incorporated by reference) |
|---|---|
| LEUCOCYTE ANTIGEN CD97 | P48960/X84700/601211 |
| CALCITONIN GENE-RELATED PEPTIDE TYPE 1 RECEPTOR, CGRP TYPE 1 RECEPTOR, CALCRL, CGRPR | Q16602/NM_005795/114190 |
| CORTICOTROPIN RELEASING FACTOR RECEPTOR 1 (CRF-R, CRF1, CRHR1, CRHR, CRFR) | P34998/NM_004382/122561 |
| CORTICOTROPIN RELEASING FACTOR RECEPTOR 2 (CRF-R, CRF2, CRHR2, CRF2R, CRH2R) | Q13324/NM_001883/602034 |
| CELL SURFACE GLYCOPROTEIN EMR1 (EMR1 HORMONE RECEPTOR) | Q14246/X81479/600493 |
| EGF-LIKE MODULE EMR2 | AAF21974/AF114491/606100 |
| EGF-LIKE MODULE-CONTAINING MUCIN-LIKE RECEPTOR EMR3 | AAK15076/AF239764/606101 |
| GASTRIC INHIBITORY POLYPEPTIDE RECEPTOR (GIP-R, GLUCOSE-DEPENDENT INSULINOTROPIC POLYPEPTIDE RECEPTOR) | P48546/NM_000164/137241 |
| GLUCAGON-LIKE PEPTIDE 1 RECEPTOR (GLP-1 RECEPTOR, GLP-1-R, GLP1R) | P43220/NM_002062/138032 |
| GLUCAGON RECEPTOR (GL-R, GCGR) | P47871/NM_000160/138033 |
| GLUCAGON-LIKE PEPTIDE 2 RECEPTOR (GLP-2 RECEPTOR, GLP-2-R, GLP-2R, GLP2R) | O95838/NM_004246/603659 |
| G PROTEIN-COUPLED RECEPTOR 56 | AAD30545/NM_005682/604110 |
| GROWTH HORMONE-RELEASING HORMONE RECEPTOR (GHRH RECEPTOR, GRF RECEPTOR, GRFR, GHRHR) | Q02643/NM_000823/139191 |
| PITUITARY ADENYLATE CYCLASE ACTIVATING POLYPEPTIDE TYPE I RECEPTOR (PACAP TYPE I RECEPTOR, PACAP-R-1, ADCYAP1R1) | P41586/NM_001118/102981 |
| PARATHYROID HORMONE RECEPTOR (PTH2) | P49190/NM_005048/601469 |
| PARATHYROID HORMONE/PARATHYROID HORMONE-RELATED PEPTIDE RECEPTOR (PTHR1) | Q03431/NM_000316/168468 |
| SECRETIN RECEPTOR (SCT-R, SCTR) | P47872/NM_002980/182098 |
| VASOACTIVE INTESTINAL POLYPEPTIDE RECEPTOR 1 (VIPR1, VPAC1) | P32241/NM_004624/192321 |
| VASOACTIVE INTESTINAL POLYPEPTIDE RECEPTOR 2 (VIPR2, VIP2R, VPAC2, etc.) | P41587/NM_003382/601970 |

A. Corticotropin Releasing Factor (CRF) and its Receptors

As an example of GPCRs contemplated by the invention, the CRF receptors are described in detail. One of skill in the art would be able to adapt these specific teachings to other members of the GPCR family, particularly type B and more particularly to subfamily B1 receptors. In certain aspects the invention includes, but is not limited to the sGPCR derived from the soluble corticotropin releasing factor receptors (sCRFR), in particular sCRFR2α. The hypothalamic hypophysiotropic peptide corticotropin releasing factor (CRF), originally isolated from the hypothalamus (Vale et al., 1981), plays an important role in the regulation of the hypothalamo-pituitary-adrenal (HPA) axis under basal and stress conditions (River and Vale, 1983; Muglia et al., 1995). Further, CRF acts to integrate endocrine, autonomic, and behavioral responses to stressors (River and Vale, 1983; Muglia et al., 1995; Koob and Heinrichs, 1999). The mammalian CRF peptide family comprises urocortin 1 (Ucn 1) (Vaughan et al., 1995) and the peptides, urocortin 2 (Ucn 2) and urocortin 3 (Ucn 3) also known as stresscopin-related peptide (Reyes et al., 2001; Hsu and Hsueh, 2001), and stresscopin (Hsu and Hsueh, 2001; Lewis et al., 2001), respectively.

The effects of CRF-related peptides are mediated through activation of two high affinity membrane receptors, CRFR1 (Chen et al., 1993; Vita et al., 1993; Chang et al., 1993) and CRFR2 (Perrin et al., 1995; Stenzel et al., 1995; Kishimoto et al., 1995; Lovenberg et al., 1995; Chen et al., 2005), which belong to the B1 subfamily of seven-transmembrane domain (7TMD) receptors that signal by coupling to G-proteins. One functional variant of the CRFR1 gene is expressed both in humans and rodents, along with several non-functional variants, which are produced by differential splicing of various exons (Pisarchik and Slominski, 2004; Grammatopoulos et al., 1999). The CRFR2 has three functional splice variants in human (α, β, and γ) and two rodent variants (α and β) that are produced by the use of alternate 5' exons (Perrin et al., 1995; Stenzel et al., 1995; Kishimoto et al., 1995; Lovenberg et al., 1995; Chen et al., 2005; Grammatopoulos et al., 1999; Kostich et al., 1998). CRFR1 mRNA is widely expressed in mammalian brain and pituitary, with high levels found in the anterior pituitary, cerebral cortex, cerebellum, amygdala, hippocampus, and olfactory bulb (Van Pett et al., 2000). In the periphery, CRFR1 is expressed in testes, ovary, skin, and spleen. CRFR2 mRNA is expressed in a discrete pattern in the brain with highest densities in the lateral septal nucleus (LS), bed nucleus of stria terminalis (BNST), ventromedial hypothalamic nucleus (VMH), olfactory bulb, and mesencephalic raphe nuclei (Van Pett et al., 2000). The CRFR2α is the major splice variant expressed in the rodent brain (Lovenberg et al. 1995) while CRFR2β is expressed in peripheral tissues, with highest levels in the skeletal muscle, heart, and skin (Perrin et al., 1995).

The distributions of CRFR1 and CRFR2 are distinct and imply diverse physiological functions, as demonstrated by the divergent phenotypes of the CRFR1 or CRFR2 null mice. Mice deficient for CRFR1 display decreased anxiety-like behavior and have an impaired stress response (Smith et al., 1998; Timpl et al., 1998), while the CRFR2-null mice have increased anxiety-like behaviors and an exaggerated HPA response to stress (Zhu et al., 1999; Valerio et al., 2001; Khan et al., 1993). However, the responses to administration of CRFR2 agonists and antagonists into specific brain regions reveal both anxiolytic and anxiogenic roles for CRFR2 (Bale and Vale, 2004).

Radioreceptor and functional assays have demonstrated that CRFR1 and CRFR2 differ pharmacologically: Ucn 1 has equal affinities for both receptors and is more potent than CRF on CRFR2, whereas Ucn 2 and Ucn 3 appear to be selective for CRFR2 (Vaughan et al, 1995; Reyes et al., 2001; Lewis et al., 2001). The activation of specific CRFRs in distinct tissues or cell types by receptor-selective CRF peptides initiates a variety of signaling pathways, including coupling to different G-proteins, stimulation of PKB, PKC, intracellular calcium, and mitogen-activated protein kinase (MAPK) (for reviews see Bale and Vale, 2004; Perrin and Vale, 1999; Brar et al., 2002).

CRFR1 and CRFR2 both exist as multiple splice variants. The inventors have identified a cDNA from mouse brain encoding an exemplary splice variant of sCRFR2α in which exon six is deleted from the nucleic acid encoding CRFR2α. Translation of this isoform produces a predicted 143 amino acid soluble protein. The translated protein includes a majority of the first extracellular domain (ECD1) of the CRFR2α followed by a unique 38 amino acid hydrophilic C-terminus resulting from a frame shift produced by deletion of exon six. Studies have demonstrated high levels of expression of sCRFR2α in the olfactory bulb, cortex, and midbrain regions. A protein corresponding to sCRFR2α, expressed and purified from either mammalian or bacterial cell systems, binds several CRF family ligands with low nanomolar affinities. Further, the purified sCRFR2α protein inhibits cellular responses to CRF and urocortin 1. Thus, a sCRFR2α protein can be a biological modulator of CRF family ligands. The modulation of CRF family ligands is not limited to brain and may be used in any tissue that is exposed to one or more members of the CRF family of ligands.

Aspects of the invention generally relate to compositions and methods of achieving a therapeutic effect, including the modulation of GPCR ligand activity, such as CRF family ligands, using a soluble GPCR ligand binding polypeptide, such as CRF binding polypeptide, as an antagonist either alone or together with one or more other hormone antagonist (e.g., small molecule antagonist), including but not limited to antagonist of ligand(s) of the CRF family.

One manner in which to antagonize the action of a ligand is to subject the ligand to a decoy or soluble receptor so as to limit the local concentration of ligand(s) that bind the decoy and modulate the ligands ability to signal via its cell surface receptor. Soluble proteins related to membrane receptors can be generated by enzymatic truncation of membrane bound receptors as suggested for the GHRH receptor (Rekaski et al., 2000), dopamine D3 receptor (Liu et al., 1994), and calcitonin receptor (Seck et al., 2003), or by alternative splicing in the case of the glutamate receptors (Malherbe et al., 1999; Zhu et al., 1999; Valerio et al., 2001). Splice variants containing only the extracellular region of GPCRs have been reported (Pisarchik and Slominski, 2004; Grammatopoulos et al., 1999; Kostich et al., 1998; Malherbe et al., 1999; Zhu et al., 1999; Valerio et al., 2001; Khan et al., 1993; Graves et al., 1992; You et al., 2000; Schwarz et al., 2000). In the majority of cases, these proteins act as binding, non-signaling molecules also referred to as decoy receptors. Two partial cDNA fragments (CRFR1e and CRFR1h), comprising deletion of exon 3 and 4, and addition of a cryptic exon in CRFR1 were identified in human skin and predicted to exist as a soluble proteins (Pisarchik and Slominski, 2004). One of these fragments, CRFR1e, exhibited dominant negative effects when co-transfected with the wildtype CRFR1.

Kehne and Lombaert (2002) disucuss non-peptidic CRF receptor antagonists for the treatment of anxiety, depression, and stress disorders. CRF is implicated in psychiatric disorders, such as anxiety and depression. Since the identification of corticotropin releasing factor (CRF) an extensive research effort has solidified the importance of this 41 amino acid peptide and its related family members in mediating the body's behavioral, endocrine, and autonomic responses to stress.

Preclinical and clinical evidence implicate CRF, in general, and CRF receptors, in particular, in anxiety and depression. Clinical studies have demonstrated a dysfunctional hypothalamic-pituitary-adrenal (HPA) axis and/or elevated CRF levels in depression and in some anxiety disorders. Preclinical data utlilizing correlational methods, genetic models, and exogenous CRF administration techniques in rodents and non-human primates supports a link between hyperactive CRF pathways and anxiogenic and depressive-like symptoms. Studies employing the use of receptor knockouts and selective, non-peptidic antagonists of the CRFR1 have demonstrated anxiolytic and antidepressant effects under certain types of laboratory conditions. A Phase II, open-label, clinical trial in major depressive disorder has reported that a CRFR1 antagonist was safe and effective in reducing symptoms of anxiety and depression.

Various nonlimiting activities of CRF antagonists are described by Owens et al. (1991). CRF antagonists are described as being effective in the treatment of stress-related illnesses; mood disorders such as depression, major depressive disorder, single episode depression, recurrent depression, child abuse induced depression, postpartum depression, dysthemia, bipolar disorders, and cyclothymia; chronic fatigue syndrome; eating disorders such as anorexia and bulimia nervosa; generalized anxiety disorder; panic disorder; phobias; obsessive-compulsive disorder; post-traumatic stress disorder; pain perception such as fibromyalgia; headache; gastrointestinal diseases; hemorrhagic stress; ulcers; stress-induced psychotic episodes; fever; diarrhea; post-operative ileus; colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiuretic hormone; obesity; chemical dependencies and addictions; drug and alcohol withdrawal symptoms; infertility; cancer; muscular spasms; urinary incontinence; hypoglycemia and immune dysfunctions including stress induced immune dysfunctions, immune suppression, and human immunodeficiency virus infections; and stress-induced infections in humans and animals. These and other conditions amenable to CRF modulation are set out in the literature, that includes Lovenberg et al. (1995); Chalmers et al. (1996); and U.S. Pat. No. 5,063,245, each of which is incorporated in its entirety by reference.

II. Polypeptides

Polypeptides of the invention include soluble forms of GPCRs or soluble receptors. Soluble receptors of the invention may comprise subunits which have been changed from a membrane bound to a soluble form. Thus, soluble peptides may be produced by truncating the polypeptide to remove, for example, the 7 transmembrane regions and/or the cytoplasmic tail. Alternatively, the transmembrane domains may be abolished by deletion, or by substitutions of the normally hydrophobic amino acid residues which comprise a transmembrane domain with hydrophilic ones. In either case, a substantially hydrophilic or soluble polypeptide is created which will reduce lipid affinity and improve aqueous solubility. Deletion of the transmembrane domains is preferred over substitution with hydrophilic amino acid residues because it avoids introducing potentially immunogenic epitopes. Soluble receptors of the invention may include any number of well-known leader sequences at the N-terminus. Such a sequence would allow the peptides to be expressed and targeted to the secretion pathway in a eukaryotic system.

A. Fusion Proteins

Receptors are powerful tools to elucidate biological pathways and to treat various disease states via their easy conversion to immunoglobulin fusion proteins. These dimeric soluble receptor forms are good inhibitors of events mediated by either secreted or surface bound ligands. By binding to these ligands they prevent the ligand from interacting with cell associated receptors. Not only are these receptor-Ig fusion proteins useful in an experimental sense, but they have been successfully used clinically in the case of TNF-R-Ig to treat inflammatory bowel disease, rheumatoid arthritis, and the acute clinical syndrome accompanying OKT3 administration (Eason et al., 1996; van Dullemen et al., 1995). The inventors contemplate that manipulation of the many events mediated by signaling through the GPCRs will have wide application in the treatment of GPCR associated diseases.

Preferably, stable plasma proteins—which typically have a half-life greater than hours in the circulation of a mammal—can be used to construct the receptor fusion proteins. Such plasma proteins include but are not limited to: immunoglobulins, serum albumin, lipoproteins, apolipoproteins and transferrin. Sequences that can target the soluble receptors to a particular cell or tissue type may also be attached to the receptor ligand binding domain to create a specifically localized soluble receptor fusion protein.

All or a functional fragment of GPCR extracellular region comprising the GPCR ligand binding domain may be fused to an immunoglobulin constant region like the Fc domain of a human IgG1 heavy chain. Soluble receptor-IgG fusions proteins are common immunological reagents and methods for their construction are well known in the art (see, for example U.S. Pat. No. 5,225,538, which is incorporated herein in its entirety by reference).

A functional GPCR ligand binding domain may be fused to an immunoglobulin (Ig) Fc domain. The Ig Fc may be derived from an immunoglobulin class or subclass including but not limited to IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system or to cross the placenta. The properties of the different classes and subclasses of immunoglobulins are described in the art.

One skilled in the art will appreciate that different amino acid residues forming the junction point of the receptor-Ig fusion protein may alter the structure, stability and ultimate biological activity of the sGPCR fusion protein. One or more amino acids may be added to the C-terminus of the selected sGPCR fragment to modify the junction point with the selected fusion domain.

The N-terminus of the sGPCR fusion protein may also be varied by changing the position at which the selected sGPCR DNA fragment is cleaved at its 5' end for insertion into the recombinant expression vector. The stability and activity of each sGPCR fusion protein may be tested and optimized using routine experimentation, including but not limited to assays for ligand binding.

Using sGPCR ligand binding domain sequences within the extracellular domain as shown herein, amino acid sequence variants may also be constructed to modify the affinity of the sGPCR molecules for their ligands. The soluble molecules of this invention can compete for binding with endogenous receptors. It is envisioned that any soluble molecule comprising a GPCR ligand binding domain that can compete with native receptors for ligand binding is a receptor blocking agent or ligand trapping agent that falls within the scope of the present invention.

B. Protien Conjugates

With respect to the protein's half-life, one way to increase the circulation half-life of a protein is to ensure a reduction in the clearance of the protein, in particular via renal clearance and receptor-mediated clearance. This may be achieved by conjugating the protein to a chemical moiety which is capable of increasing the apparent size, thereby reducing renal clearance and increasing the in vivo half-life. Furthermore, attachment of a chemical moiety to the protein may effectively block proteolytic enzymes from physical contact with the protein, thus preventing degradation by non-specific proteolysis. Polyethylene glycol (PEG) is one such chemical moiety that has been used in the preparation of therapeutic protein products. Recently, G-CSF molecule modified with a single, N-terminally linked 20 kDa PEG group (Neulastam) was approved for sale in the United States. This PEGylated G-CSF molecule has been shown to have an increased half-life compared to non-PEGylated G-CSF and thus may be administered less frequently than current G-CSF products, but it does not reduce the duration of neutropenia significantly compared to non-PEGylated G-CSF.

Polyethylene glycol (PEG) modification is important for pharmaceutical and biotechnological applications. PEGylation (the covalent attachment of PEG) leads for example to shielding of antigenic or immunogenic epitopes. Moreover, it reduces receptor-mediated uptake by the reticuloendothelial system or prevents recognition and degradation by proteolytic enzymes. PEGylation of proteins has been shown to increase their bioavailability by reducing the renal filtration.

The term "conjugate" is intended to indicate a heterogeneous molecule formed by the covalent attachment of one or more polypeptides, typically a single polypeptide, to one or more non-polypeptide moieties such as polymer molecules, lipophilic compounds, carbohydrate moieties or organic derivatizing agents. The term covalent attachment means that the polypeptide and the non-polypeptide moiety are either directly covalently joined to one another, or else are indirectly covalently joined to one another through an intervening moiety or moieties, such as a bridge, spacer, or linkage moiety or moieties. Preferably, the conjugate is soluble at relevant concentrations and conditions, i.e., soluble in physiological fluids such as blood. Compositions and methods for preparing a conjugate of the invention are described in U.S. Pat. No. 6,831,158, which is incorporated herein by reference in its entirety. The methods described in U.S. Pat. No. 6,831,158 are directed to conjugation of G-CSF, but can be readily adapted to conjugation of the sGPCRs of the present invention.

The "polymer molecule" is a molecule formed by covalent linkage of two or more monomers. The term "polymer" may be used interchangeably with the term "polymer molecule". The term is intended to cover carbohydrate molecules including carbohydrate molecules attached to the polypeptide by in vivo N- or O-glycosylation, such molecule is also referred to as "an oligosaccharide moiety". Except where the number of polymer molecule(s) is expressly indicated every reference to "a polymer", "a polymer molecule", "the polymer" or "the polymer molecule" contained in a polypeptide of the invention or otherwise used in the present invention shall be a reference to one or more polymer molecule(s).

The term "attachment group" is intended to indicate an amino acid residue group of the polypeptide capable of coupling to the relevant non-polypeptide moiety. For instance, for polymer conjugation, in particular to PEG, a frequently used attachment group is the ϵ-amino group of lysine or the N-terminal amino group. Other polymer attachment groups include a free carboxylic acid group (e.g., that of the C-terminal amino acid residue or of an aspartic acid or glutamic acid residue), suitably activated carbonyl groups, oxidized carbohydrate moieties and mercapto groups. Useful attachment groups and their matching non-peptide moieties are exemplified in Table 2.

Substitutional variants typically contain the exchange of one amino acid for another at one or more sites within the protein, and may be designed to modulate one or more properties of the polypeptide such as stability against proteolytic cleavage or immunogenicity. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also

TABLE 2

| Attachment Group | Amino Acid | Example of non-peptide moiety | Conjungation method/ activated PEG | Reference |
|---|---|---|---|---|
| —NH$_2$ | N-terminal Lys, Arg, His | Polymer, e.g., PEG with amide or imine group | mPEG-SPA Tresylated mPEG | Shearwater Corp. Delgado et al., 1992. |
| —COOH | C-terminal Asp and Glu | Polymer, e.g., PEG with ester or amide group Oligosaccharide moiety | mPEG-Hz in vitro coupling | Shearwater Corp. |
| —SH | Cys | Polymer, e.g. PEG, with disulfide, maleimide or vinyl sulfone group Oligosaccharide moiety | PEG vinylsullphone PEG-maleimide In vitro coupling | Shearwater Corp. Delgado et al., 1992 |
| —OH | Ser, Thr, —OH, lys | Oligosaccharide moiety PAG with ester, ether, carbamate, carbonate | In vivo O-linked glycosylation | |
| —CONH$_2$ | Asn as part of an N-glycosylation site | Oligosaccharide moiety Polymer, e.g. PEG | In vivo N-glycosylation | |
| Aromatic —CONH$_2$ | Phe, Tyr, Trp, Gln | Oligosaxxharide moiety | In vitro coupling | Yan and Wold, 1984 |
| Aldehyde Ketone | Oxidized oligosaccharide | Polymer, e.g. PEG PEG hydroxide | PEGylation | Andresz et al., 1978 WO 92/16655 WO 00/23114 |
| Guanidino | Arg | Oligosaccharide moiety | In vitro coupling | Lunblad and Noyes, Chemical reagents for protein modification, CRC Press |
| Imidazole ring | His | Oligosaccharide moiety | In vitro coupling | Lunblad and Noyes, Chemical reagents for protein modification, CRC Press |

C. Site-Specific Mutagenesis

In one embodiment, amino acid sequence variants of a polypeptide can be prepared. These may, for instance, be minor sequence variants of polypeptides that arise due to natural variation within the population or they may be homologs found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below.

Amino acid sequence variants of the polypeptide can be substitutional, insertional, or deletion variants. Deletion variants lack one or more residues of the native protein which are not essential for function or immunogenic activity, and are exemplified by the variants of a receptor lacking a transmembrane sequence.

can include hybrid proteins containing sequences from other proteins and polypeptides. For example, an insertional variant could include portions of the amino acid sequence of a polypeptide from one species, together with portions of the homologous polypeptide from another species. Other insertional variants can include those in which additional amino acids are introduced within the coding sequence of the polypeptide, for example a protease cleavage site(s) may be introduced.

Modification and changes may be made in the structure of a polynucleotide and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological activity certain amino acid substitutions can be made in a protein sequence still obtain a protein with like properties. It is thus contemplated by the inventors that various changes may be made in the DNA sequences of genes, mRNA or polynucleotides without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982).

TABLE 3

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUG GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. It is known in the art that certain amino acids may be substituted by other amino acids having a similar hydropathic index or score and still result in a protein with similar biological activity. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. In general, the technique of site-specific mutagenesis is well known in the art. The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site-directed mutagenesis, which eliminates the step of transferring the gene of interest from a phage to a plasmid.

The preparation of sequence variants of a GPCR, including but not limted to, sCRFR2α, polynucleotide using site-directed mutagenesis is provided as a means of producing potentially useful species, i.e., species with altered ligand binding properties that include an increased affinity for a particular ligand, and is not meant to be limiting, as there are other ways in which sequence variants of nucleic acids may be obtained. For example, recombinant vectors encoding the desired gene may be treated with mutagenic agents, such as hydroxylamine, to obtain sequence variants.

D. Expression and Purification of Polypeptides

The polynucleotides of the invention, in particular 100, 150, 200 250, 300, 400, 450, 500, 550 or more contiguous nucleotides of the DNA encoding a GPCR, a family B GPCR, a family B1 GPCR, or a polynucleotide that is 70, 75, 80, 85, 90, 95, 98, or 100% identical to the sequence specified in the accompaning sequence listing, e.g., SEQ ID NO:1, 3, 5, 7, 9, 11, 13, or 14 can be expressed as encoded peptides or proteins. In a particular aspect the DNA encodes all or part of a GPCR extracellular domain and in particular an amino terminal extracellular domain. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

In certain embodiments, the present invention concerns novel compositions comprising at least one proteinaceous molecule, such as sGPCR, asCRFR, or a sCRFR2. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein. Furthermore, these terms may be applied to fusion proteins as well.

In certain embodiments the size of the at least one proteinaceous molecule may comprise, but is not limited to, about or at least 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000, 1100, 1200, 1300, 1400, 1500, 1750, 2000, 2250, 2500 or greater amino molecule residues, and any range derivable therein, particularly 50, 60, 70, 80, 90, 100, 110, 120, 130, 140, 150, 160, 170, 180, 190, or more contiguous amino acid sequences of such lengths of a GPCR, a family B GPCR, a family B1 GPCR, or SEQ ID NO:2, 4, 6, 8, 10, 12 or 15, including the full length of SEQ ID NO:4, 8, 12, or 15. Both cDNA and genomic sequences are suitable for eukaryotic expression, as the host cell will generally process the genomic transcripts to yield functional mRNA for translation into protein.

As used herein, the terms "engineered" and "recombinant" cells are intended to refer to a cell into which an exogenous DNA segment or polynucleotide, such as a cDNA or polynucleotide has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic DNA, and may also include genes positioned adjacent to a promoter not naturally associated with the particular introduced gene.

To express a recombinant protein or polypeptide, whether mutant or wild-type, in accordance with the present invention one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli, B. subtilis, E. coli strain RR1, E. coli LE392, E. coli B, E. coli χ 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species transformed with recombinant phage DNA, plasmid DNA or cosmid DNA expression vectors.

The polynucleotide or polynucleotide fragment encoding a polypeptide can be inserted into an expression vector by standard subcloning techniques. In one embodiment, an E. coli expression vector is used that produces the recombinant polypeptide as a fusion protein, allowing rapid affinity purification of the protein. Examples of such fusion protein expression systems are the glutathione S-transferase system (Pharmacia, Piscataway, N.J.), the maltose binding-protein system (New England Biolabs, Beverley, Mass.), the FLAG system (IBI, New Haven, Conn.), and the 6xHis system (Qiagen, Chatsworth, Calif.). Further useful vectors include pIN vectors (Inouye et al., 1985); and pGEX vectors, for use in generating glutathione S-transferase (GST) soluble fusion proteins. Other suitable fusion proteins are those with β-galactosidase, ubiquitin, or the like.

For expression in Saccharomyces, the plasmid YRp7, for example, is commonly used (Stinchcomb et al., 1979; Kingsman et al., 1979; Tschemper et al., 1980). This plasmid contains the trp1 gene, which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture including mammalian and insect cells (e.g., U.S. Pat. No. 4,215,051).

Examples of useful mammalian host cell lines are VERO and HeLa cells, Chinese hamster ovary (CHO) cell lines, WI38, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. The efficiency of expression may be enhanced by the inclusion of appropriate transcription enhancer elements or transcription terminators (Bittner et al., 1987).

For long-term, high-yield production of recombinant proteins, stable expression is preferred. For example, cell lines that stably express constructs encoding G-proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk⁻, hgprt⁻ or aprt⁻ cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colbere-Garapin et al., 1981); and hygro, which confers resistance to hygromycin.

Once the polynucleotide sequence coding a particular polypeptide has been determined or engineered, the polynucleotide can be inserted into an appropriate expression system. In this case, the inventors contemplate a polynucleotide encoding a sGPCR ligand binding domain polypeptide. The polynucleotide can be expressed in any number of different recombinant DNA expression systems to generate large amounts of the polypeptide product, which can then be purified and/or isolated to be used as a therapeutic or to vaccinate animals to generate antisera, and in certain aspects of the invention as an antagonist of GPCR ligand and/or GPCR activation. In further aspects, sGPCRs of the invention can be used in methods to detect, screen, or identify ligands, receptors, or agonist and/or antagonist of GPCRs. A polynucleotide of the invention may be expressed to obtain a GPCR ligand binding domain, a family B GPCR ligand binding domain, a family B1 GPCR ligand binding domain, a sCRFR ligand binding domain or a CRFR2 ligand binding domain polypeptide comprising an amino acid sequence including all or part of the amino acid sequence as set forth in the sequence listing, e.g., SEQ ID NO:2, 4, 6, 8, 10, 12, or 15.

As an alternative to recombinant polypeptides, synthetic peptides corresponding to the polypeptides of the invention can be prepared, including antigenic peptides. Such antigenic peptides are at least six amino acid residues long, and may contain up to approximately 35 residues. Automated peptide synthesis machines include those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

1. Purification of Expressed Proteins

Further aspects of the present invention concern the purification for isolation, and in particular embodiments, the substantial purification, of a protein or peptide comprising all or part of a sGPCR ligand binding domain. The term "purified or isolated protein or peptide" as used herein, is intended to refer to a composition, isolatable from other components, wherein the protein, polypeptide or peptide is purified to any degree relative to its naturally-obtainable state, i.e., in this case, relative to its purity within a organism or tissue. A purified or isolated protein or peptide therefore also refers to a protein or peptide, free from the environment in which it may naturally occur. A purified or isolated protein or polypeptide may have a purity greater than or at least 70, 75, 80, 85, 90, 95, 98, or 99% purity.

Generally, "purified" will refer to a protein or peptide composition that has been subjected to fractionation to remove various other components, and which composition substantially retains its expressed activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity (e.g., binding affinity for GPCR ligand including, but not limited to CRF or a ligand of the CRF family) of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity, which may include binding activity or affinity, will, of course, be dependent upon the particular assay technique chosen.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite, and/or affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

E. Preparation of Antibodies Specific for sGPCRs

For some embodiments, it will be desired to produce antibodies that bind with high specificity to the protein product(s) of an isolated nucleic acid encoding for sGPCR, including but not limted to sCRFR2α. In certain aspects, an antibody preparation is contemplated that recognizes or binds the c-terminus of a GPCR, particularly a splice variant such as a sCRFR2α splice variant and thus can be used to distingush a sGPCR polypeptide from a membrane associated receptor. Such antibodies may be used in any of a variety of applications known to those of skill in the art, including but not limited to: immunodetection methods, immunoprecipitation methods, ELISA assays, protein purification methods, etc. Means for preparing and characterizing antibodies are well known in the art (See, e.g., Harlow and Lane, 1988, incorporated herein by reference).

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig, a horse, or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The animals are injected with antigen as described above. Following immunization, somatic cells with the potential for producing antibodies, specifically B lymphocytes (B cells), are selected for use in the MAb generating protocol. Often, a panel of animals will have been immunized and the spleen of the animal with the highest antibody titer will be removed and the spleen lymphocytes obtained by homogenizing the spleen with a syringe.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas). Any one of a number of myeloma cells may be used, as are known to those of skill in the art (Goding, 1986). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM 1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of a monoclonal antibody can be obtained by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or by expression of full-length polynucleotide or of polynucleotide fragments encoding all or part of Mab.

Antibody conjugates may be prepared by methods known in the art, e.g., by reacting an antibody with an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3H$, $^{125}I$, $^{131}I$ $^{32}P$, $^{35}S$, $^{14}C$, $^{51}Cr$, $^{36}Cl$, $^{57}Co$, $^{58}Co$, $^{59}Fe$, $^{75}Se$, $^{152}Eu$, and $^{99m}Tc$. Radioactively labeled antibodies of the present invention can be produced according to well-known methods. For instance, antibodies can be iodinated by contact with sodium or potassium iodide and a chemical oxidizing agent such as sodium hypochlorite, or an enzymatic oxidizing agent, such as lactoperoxidase. Antibodies according to the invention may be labeled with technetium-$^{99}$ by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as $SnCl_2$, a buffer solution such as sodium-potassium phthalate solution, and the antibody.

III. Nucleic Acids Encoding sGPCR Polypeptides

The present invention includes nucleic acids that encode all or part of a sGPCR, such as but not limited to a GPCR, a family B GPCR, a family B1 GPCR, a CRFR, or a CRFR2 polypeptide, and may include various nucleic acid sequences needed for delivery of the nucleic acid sequence as well as the transcription and/or translation of the nucleic acid seqeunce. Nucleic acid molecules of the invention may include various contiguous stretches of the nucleic acid, for example about 10, 15, 17, 20, 25, 30, 35, 40, 45, 50, 55, 60, 70, 75, 80, 85, 90, 95, 100, 125, 150, 175, 200, 250, 300, 350, 400, 500, 600, 700, 800, 900, 1000, 1250, 1500, 1750, 2000, 2100, including all or part of the full length nucleic acid sequences in the sequence listing, e.g., SEQ ID NO:1, 3, 5, 7, 9, 11, 13, or 14, or polynucleotides of those GPCRs referenced herein, fragments thereof, mRNAs, or cDNAs comprising sequences described or referenced herein, and mutants of each are contemplated. Also contemplated are molecules that are complementary to the above mentioned sequences and that bind to these sequences under high stringency conditions. These probes will be useful in a variety of hybridization embodiments, such as Southern and northern blotting.

Various probes and primers can be designed around the disclosed nucleotide sequences. Primers may be of any length but, typically, are 10-20 bases in length. In particular aspects, the probe or primer can be used to identify or screen for the presence of an alternatively spliced form of a GPCR, such as but not limited to the CRFR2 gene that includes an exon 5/exon 7 splice junction (may also be described as an exon 3/exon 5 juction as it relates to CRFR2α transcrition). These probes or primers may either hybridize unique sequence of the engineered nulceic acid or splice junction, or amplify a nucleic acid characteristic of the engineered nucleic acid or the splice junction. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

In certain aspects the nucleic acid seqeunces of the invention may be used to encode various polypeptides described herein. In one embodiment of the present invention, the nucleic acid sequences may be used as hybridization probes or amplification primers. In certain embodiments, these probes and primers consist of oligonucleotide fragments. Such fragments should be of sufficient length to provide specific hybridization to an RNA or DNA sample extracted from tissue. The sequences typically will be 10-20 nucleotides, but may be longer. Longer sequences, e.g., 40, 50, 100, 500 and even up to full length, are preferred for certain embodiments.

The use of a hybridization probe of between 17 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production. Accordingly, the nucleotide sequences of the invention may be used for their ability to selectively form duplex molecules with complementary stretches of genes, polynucleotides or RNAs, or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent or high stringency conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

In certain embodiments, it will be advantageous to employ nucleic acid sequences of the present invention in combination with an appropriate means of detection, such as a fluorescent or radiolabel, for determining hybridization. A wide variety of appropriate indicator means are known in the art, including fluorescent, radioactive, enzymatic or other ligands, such as avidin/biotin, which are capable of being detected.

For applications in which the nucleic acid segments of the present invention are incorporated into expression vectors, such as plasmids, cosmids or viral polynucleotides, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific polynucleotide may be introduced into recombinant host cells and employed for expressing a sGPCR, such as but not limited to a sCRFR2α polypeptide. Alternatively, through the application of genetic engineering techniques, subportions or derivatives of selected polynucleotides may be employed.

Throughout this application, the term "expression construct" is meant to include any type of genetic construct containing a nucleic acid having a sequence defining a product, such as but not limited to a product encoding a polypeptide, in which part or all of the nucleic acid sequence is capable of being transcribed. The transcript may be translated into a protein, but it need not be. Thus, in certain embodiments, expression includes both transcription of a polynucleotide and translation of a RNA into a polypeptide product.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a polynucleotide. The phrase "under transcriptional control" means that the promoter is in the correct location and orientation in relation to the nucleic acid to control RNA polymerase initiation and expression of the polynucleotide. The term promoter will be used here to refer to a group of transcriptional control modules that are clustered around the initiation site for a RNA polymerase, in particular RNA polymerase II. In certain aspects, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Several elements/promoters, as described below, may be employed, in the context of the present invention, to regulate the expression of a polynucleotide, such as a transgene. This list is not intended to be exhaustive of all the possible elements involved in the promotion of transgene expression but, merely, to be exemplary thereof.

Any promoter/enhancer combination (as per the Eukaryotic Promoter Data Base EPDB) could also be used to drive expression of a polynucleotide. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct. Use of the baculovirus system will involve high level expression from the powerful polyhedrin promoter.

Promoters include, but are not limited to Immunoglobulin Heavy Chain, Immunoglobulin Light Chain, T-Cell Receptor, HLA DQ α and DQ β, β-Interferon, Interleukin-2, Interleukin-2 Receptor, MHC Class II 5, MHC Class II HLA-DRα, β-Actin, Muscle Creatine Kinase, Prealbumin (Transthyretin), Elastase I, Metallothionein, Collagenase, Albumin Gene, α-Fetoprotein, α-Globin, β-Globin, c-fos, c-HA-ras, Insulin, Neural Cell Adhesion Molecule (NCAM), $α_1$-Antitrypsin, H2B (TH2B) Histone, Mouse or Type I Collagen, Glucose-Regulated Proteins (GRP94 and GRP78), Rat Growth Hormone, Human Serum Amyloid A (SAA), Troponin I (TN I), Platelet-Derived Growth Factor, Duchenne Muscular Dystrophy, SV40, Polyoma, Retroviruses, Papilloma Virus, Hepatitis B Virus, Human Immunodeficiency Virus, Cytomegalovirus, Gibbon Ape Leukemia Virus.

Various element (inducers) include, but are not limited to MT II (Phorbol Ester (TPA) Heavy metals); MMTV (Glucocorticoids, β-Interferon, poly(rI)X, poly(rc)); Adenovirus 5 E2 (E1a); c-jun (Phorbol Ester (TPA), $H_2O_2$); Collagenase (Phorbol Ester (TPA)); Stromelysin (Phorbol Ester (TPA), IL-1); SV40 (Phorbol Ester (TPA)); Murine MX Gene (Interferon, Newcastle Disease Virus); GRP78 Gene (A23187); α-2-Macroglobulin (IL-6); Vimentin (Serum); MHC Class I Gene H-2kB (Interferon); HSP70 (E1a, SV40 Large T Antigen); Proliferin (Phorbol Ester-TPA); Tumor Necrosis Factor (FMA); and Thyroid Stimulating Hormone α Gene (Thyroid Hormone).

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated is the inclusion of a terminator as an element of an expression cassette. These elements can serve to enhance message levels and to minimize read through from the cassette into other sequences.

In various embodiments of the invention, an expression construct may comprise a virus or engineered construct derived from a viral genome. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressinG-proteins of interest or (ii) to transform cells in vitro or in vivo to provide therapeutic polypeptides in a gene therapy scenario.

In an alternative embodiment, the sGPCR encoding nucleic acids employed may actually encode antisense constructs that hybridize, under intracellular conditions, to a sGPCR or other encoding nucleic acid. The term "antisense construct" is intended to refer to nucleic acids, preferably oligonucleotides, complementary to the base sequences of a target DNA or RNA.

As used herein, the terms "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

A. Detection and Quantitation of Nucleic Acids

One embodiment of the instant invention comprises a method for identification of sGPCR nucleic acid, such as but not limited to CRFR2α nucleic acids, in a biological sample by amplifying and detecting nucleic acids corresponding to sGPCR. The biological sample can be any tissue or fluid in which the polynucleotide might be present. Nucleic acid used as a template for amplification is isolated from cells contained in the biological sample, according to standard methodologies (Sambrook et al., 1989). The nucleic acid may be fractionated or whole cell RNA.

Pairs of primers that selectively hybridize to nucleic acids corresponding to sGPCR are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. The amplification products may be detected. In certain applications, the detection may be performed by visual means. Alternatively, the detection may involve indirect identification of the product via chemiluminescence, radioactive scintigraphy of incorporated radiolabel or fluorescent label, or even via a system using electrical or thermal impulse signals (Affymax technology; Bellus, 1994).

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety. Polymerase chain reaction methodologies are well known in the art.

Another method for amplification is the ligase chain reaction ("LCR"), disclosed in EPA No. 320 308, which is incorporated herein by reference in its entirety. U.S. Pat. No. 4,883,750 describes a method similar to LCR for binding probe pairs to a target sequence. Also, Qbeta Replicase, described in PCT Application No. PCT/US87/00880, may be used as still another amplification method in the present invention. An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992), incorporated herein by reference in its entirety. Still further, Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. Target specific sequences can also be detected using a cyclic probe reaction (CPR). Still another amplification method described in GB Application No. 2 202 328, and in PCT Application No. PCT/US89/01025, each of which is incorporated herein by reference in its entirety, may be used in accordance with the present invention. Other nucleic acid amplification procedures include transcription-based amplification systems (TAS), including nucleic acid sequence based amplification (NASBA) and 3SR (Kwoh et al., 1989); PCT Application WO 88/10315, incorporated herein by reference in their entirety).

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

IV. Methods for sGPCR Gene Expression

In one embodiment of the present invention, there are provided methods for increased sGPCR expression in a cell, such as but not limited to sCRFR2α expression. This is particularly useful where there is an aberration in the protein or protein expression is not sufficient for normal function. This will allow for the alleviation of symptoms of disease experienced as a result of deficiency of sGPCR, hyperactivation of GPCR or an abundance of GPCR ligand.

The general approach to increasing sGPCR is to contact or administer to a cell, tissue, animal, or subject a sGPCR polypeptide. While it is preferred that the protein may be delivered directly, a conceivable embodiment involves providing a nucleic acid encoding a sGPCR polypeptide to the cell or neighboring cells. Following this provision, the sGPCR polypeptide is synthesized by the host cell's transcriptional and translational machinery, as well as any that may be provided by the expression construct. Cis-acting regulatory elements necessary to support the expression of the sGPCR polynucleotide will be provided, in the form of an expression construct. It also is possible that expression of virally-encoded sGPCR could be stimulated or enhanced, or the expressed polypeptide be stabilized, thereby achieving the same or similar effect.

In order to effect expression of constructs encoding sGPCR polynucleotides, the expression construct must be delivered by a delivery vector into a cell. One mechanism for delivery is via viral infection, where the expression construct is encapsidated in a viral particle which will deliver either a replicating or non-replicating nucleic acid.

The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et. al., 1990), and receptor-mediated transfection (Wu and Wu, 1987; Wu and Wu, 1988). Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well. Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Other expression constructs which can be employed to deliver a nucleic acid encoding a sCRFR2α polynucleotide into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

V. Pharmaceuticals and Methods for the Treatment of Disease

In additional embodiments, the present invention concerns formulation of one or more of the polynucleotide, polypeptide, and/or antibody compositions disclosed herein in pharmaceutically-acceptable solutions for administration to a cell, tissue, animal, patient, or subject either alone, or in combination with one or more other modalities of therapy.

Aqueous pharmaceutical compositions of the present invention will have an effective amount of a sGPCR expression construct, an expression construct that encodes a therapeutic gene along with sGPCR, or a sGPCR protein and/or compound that modulates GPCR ligand activity or sensititvy, or other endocrine function. Such compositions generally will be dissolved or dispersed in a pharmaceutically acceptable carrier or aqueous medium. An "effective amount," for the purposes of therapy, is defined at that amount that causes a clinically measurable difference in the condition of the subject. This amount will vary depending on the substance, the condition of the patient, the type of treatment, etc.

The phrases "pharmaceutically or pharmacologically acceptable" refer to molecular entities and compositions that do not produce a significant adverse, allergic or other untoward reaction when administered to an animal, or human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredients, its use in the therapeutic compositions is contemplated.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains sGPCR alone or in combination with a conventional therapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" (1980)). Some variation in dosage will necessarily occur depending on the condition of the subject being treated. The person responsible for administration will, in any event, determine the appropriate dose for the individual subject.

In certain aspects of the methods of the invention, the route the therapeutic composition is administered may be by parenteral administration. The parenteral administration may be intravenous injection, subcutaneous injection, intramuscular injection, intramedullary injection, ingestion or a combination thereof. In certain aspects, the composition comprising sGPCR is administered from about 0.1 to about 10 microgram/kg/body weight per dose. In certain aspects, the composition comprising sGPCR is administered from about 1 to about 5 microgram/kg/body weight per dose. In certain aspects, the composition comprising sGPCR is administered from about 1.2 to about 3.6 microgram/kg/body weight per dose. In certain aspects, the composition comprising sGPCR is administered from about 1.2 to about 2.4 microgram/kg/body weight per dose. In preferred aspects, the amount of sGPCR administered per dose may be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, abot 3.1, about 3.2, about 3.3, about 3.4, about 3 5, about 3.6, about 3.7, about 3.8, about 3.9, about 4.0, about 4.1, about 4.2, about 4.3, about 4.4, about 4.5, about 4.6, about 4.7, about 4.8, abotu 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, or more micrograms/kg/body.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

A. Alimentary Delivery

The term "alimentary delivery" refers to the administration, directly or otherwise, to a portion of the alimentary canal of an animal. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastro-intestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

1. Oral Delivery

In certain applications, the pharmaceutical compositions disclosed herein may be delivered via oral administration to an animal, patient, or subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active components may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active component sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

2. Rectal Administration

Therapeutics administered by the oral route can often be alternatively administered by the lower enteral route, i.e., through the anal portal into the rectum or lower intestine. Rectal suppositories, retention enemas or rectal catheters can be used for this purpose and may be preferred when patient compliance might a otherwise be difficult to achieve (e.g., in pediatric and geriatric applications, or when the patient is vomiting or unconscious). Rectal administration may result in more prompt and higher blood levels than the oral route, but the converse may be true as well (Harvey, 1990). Because about 50% of the therapeutic that is absorbed from the rectum will bypass the liver, administration by this route significantly reduces the potential for first-pass metabolism (Benet et al., 1996).

B. Parenteral Delivery

The term "parenteral delivery" refers to the administration of a therapeutic of the invention to an animal, patient or subject in a manner other than through the digestive canal. Means of preparing and administering parenteral pharmaceutical compositions are known in the art (see, e.g., Avis, 1990).

C. Intraluminal Administration

Intraluminal administration, for the direct delivery of a therapeutic to an isolated portion of a tubular organ or tissue (e.g., such as an artery, vein, ureter or urethra), may be desired for the treatment of patients with diseases or conditions afflicting the lumen of such organs or tissues. To effect this mode of administration, a catheter or cannula is surgically introduced by appropriate means. After isolation of a portion of the tubular organ or tissue for which treatment is sought, a composition comprising a therapeutic of the invention is infused through the cannula or catheter into the isolated segment. After incubation for from about 1 to about 120 minutes, during which the therapeutic is taken up or in contact with the cells of the interior lumen of the vessel, the infusion cannula or catheter is removed and flow within the tubular organ or tissue is restored by removal of the ligatures which effected the isolation of a segment thereof (Morishita et al., 1993). Therapeutic compositions of the invention may also be combined with a biocompatible matrix, such as a hydrogel material, and applied directly to vascular tissue in vivo.

D. Intraventricular Administration

Intraventricular administration, for the direct delivery of a therapeutic to the brain of a patient, may be desired for the treatment of patients with diseases or conditions afflicting the brain. One method to affect this mode of administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., 1984; Shaw, 1993). The pump is used to inject the therapeutic and allows precise dosage adjustments and variation in dosage schedules with the aid of an external programming device. The reservoir capacity of the pump is 18-20 mL and infusion rates may range from 0.1 mL/h to 1 mL/h. Depending on the frequency of administration, ranging from daily to monthly, and the dose of drug to be administered, ranging from 0.01 µg to 100 g per kg of body weight, the pump reservoir may be refilled at 3-10 week intervals. Refilling of the pump may be accomplished by percutaneous puncture of the self-sealing septum of the pump.

E. Intrathecal Drug Administration

Intrathecal drug administration, for the introduction of a therapeutic into the spinal column of a patient may be desired for the treatment of patients with diseases of the central nervous system. To effect this route of administration, a silicon catheter may be surgically implanted into the L3-4 lumbar spinal interspace of a human patient, and is connected to a subcutaneous infusion pump which has been surgically implanted in the upper abdominal region (Luer and Hatton, 1993; Ettinger et al., 1978; Yaida et al., 1995). The pump is used to inject the therapeutic and allows precise dosage adjustments and variations in dose schedules with the aid of an external programming device. The reservoir capacity of the pump is 18-20 mL, and infusion rates may vary from 0.1 mL/h to 1 mL/h. Depending on the frequency of drug administration, ranging from daily to monthly, and dosage of drug to be administered, ranging from 0.01 µg to 100 g per kg of body weight, the pump reservoir may be refilled at 3-10 week intervals. Refilling of the pump is accomplished by a single percutaneous puncture to the self-sealing septum of the pump.

To effect delivery to areas other than the brain or spinal column via this method, the silicon catheter is configured to connect the subcutaneous infusion pump to, e.g., the hepatic artery, for delivery to the liver (Kemeny et al., 1993).

F. Vaginal Delivery

Vaginal delivery provides local treatment and avoids first pass metabolism, degradation by digestive enzymes, and potential systemic side-effects. Vaginal suppositories (Block, Chapter 87 In: Remington's Pharmaceutical Sciences, 18th Ed., Gennaro, ed., Mack Publishing Co., Easton, Pa., 1990, pages 1609-1614) or topical ointments can be used to effect this mode of delivery.

G. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the cells and methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

A. Materials and Methods

Isolation of the mouse soluble CRFR2α cDNA. The soluble CRFR2α splice variant was isolated in parallel with that of the mouse CRFR2α ortholog. PCR primers were designed based on the homology between known mammalian CRFR2 genes. The following oligonucleotide primers, 5' CCCCGAAGCTGCCCGACTGG 3' (SEQ ID NO:16) (sense) and 5' GGAAGGCTGTAAAGGATGGAGAAG 3' (SEQ ID NO:17) (antisense) were used to screen cDNA prepared from mouse whole brain poly(A)+ RNA which was reverse transcribed using oligo dT or random primers. PCR was performed at 62° C. for 35 cycles with 90 sec extension at 72° C. The amplified fragments were subcloned into pCRIITOPO vector (Invitrogen, Carlsbad, Calif.), sequenced, and found to encode the full-length CRFR2α novel splice variant lacking exon six, sCRFR2α (Chen et al., 2005).

Semi-quantitative RT-PCR and Southern analysis. The following mouse peripheral and CNS tissues were dissected and directly subjected to total RNA isolation as previously described (Chen et al., 2005): total brain, olfactory bulb, hypothalamus, cortex, cerebellum, hippocampus, midbrain, pons/medulla oblongata, spinal cord and pituitary. The cDNA products were used as templates for semi-quantitative and RT PCR analysis using specific primers for CRFR2α, sCRFR2α and the ribosomal protein S 16. The locations of the oligonucleotide primers at exons three and seven result in the amplification of two products of 418 and 309 corresponding to CRFR2α and sCRFR2α, respectively. Oligonucleotide primers sequence and PCR conditions can be found in the supporting text.

Extracellular receptor kinase 1/2 (ERK1/2) assay. CATH.a cells were equilibrated with DMEM supplemented with 1% (w/v) bovine serum albumin (BSA) for 6 hr and then stimulated with 0.1% DMEM/BSA (vehicle) or 10 nM Ucn I in the presence or absence of 0.4 or 4 nM sCRFR2α diluted in 0.1% DMEM/BSA. Cells were harvested immediately and analyzed for phosphorylated ERK1/2-p42, 44, as previously described (Chen et al., 2005).

Transient transfections and luciferase assay. The HEK293T cells were transfected with a luciferase reporter containing a fragment of the EVX1 gene containing a potent CRE site. The cells were harvested and the luciferase reporter activity was assayed as previously described (Chen et al., 2005). Twenty hours posttransfection, cells were treated for 4 h with vehicle or with Ucn 1 (0.0001-100 nM) in the presence or absence of 0.1 nM sCRFR2α.

Radio-Immuno Assays (RIA). Antisera was raised in rabbits immunized with a synthetic peptide fragment encoding the unique C-terminal tail (aa 113-143) of mouse sCRFR2α conjugated to Keyhole Limpet Hemocyanin using a protocol previously described for inhibin subunits (Vaughan et al., 1989). The analog $Tyr^{113}$ sCRFR2α (113-143) was radiolabelled with $Na^{125}I$ using chloramine-T and purified by HPLC (Vaughan et al., 1989) for use as tracer in the HA. The procedure for sCRFR2α RIA was similar to that previously described in detail for inhibin subunits (Vaughan et al., 2005). Briefly, anti-sCRFR2α was used at 1/300,000 final dilution and synthetic sCRFR2α (113-143) was used as standard. Murine tissues were acid extracted and partially purified using octadecyl silica cartridges as described (Vaughan et al., 1989). Lyophilized samples were tested at three to seven dose levels. Free tracer was separated from bound by the addition of sheep anti-rabbit γ-globulins and 10% (wt/vol) polyethylene glycol. The EC50 and minimum detectable dose for sCRFR2α are ~5 pg and 100 pg per tube, respectively.

Immunohistochemistry. Adult male C57B6J mice (Jackson Laboratories) and Sprague-Dawley albino rats (Harlan Sprague-Dawley) were anesthetized with chloral hydrate (350 mg/kg, ip) and perfused with Zamboni's fixative (Bittencourt et al., 1999), followed by 0-4 hr. post-fixation. Regularly spaced (1-in-4) series of 30 μm thick frontal sections throughout the brain were prepared for nickel-enhanced avidin-biotin-immunoperoxidase localization of sCRFR2α-ir using Vectastain Elite reagents (Vector Laboratories, Burlingame, Calif.). Primary sCRFR2α antisera were adsorbed against the carrier, affinity purified and used at a dilution of 1:2000. Specificity of immunostaining was evaluated using primary antisera preincubated overnight at 4° C. with 0-300 μM synthetic immunogen. Labeling was also evaluated in mutant mice deficient in either or both CRFRs (Smith et al., 1998; Bale et al. 2000). Detailed description of the fluorescence immunocytochemical analysis of COSM6 cells transfected with sCRFR2α can be found in the supporting text.

Mammalian expression of sCRFR2α: A cDNA corresponding to amino acids 1-143, modified by PCR to include a FLAG epitope following amino acid 143, was subcloned into pSec-Tag2 HygroA (Invitrogen, Carlsbad, Calif.) and used for transfection of COSM6 cells as described (Perrin et al., 2001). After 4 days, the media was collected and sCRFR2α was enriched by purification using FLAG-agarose (Sigma, St. Louis, Mo.) immunoaffinity chromatography. The protein was detected by immunoblot analysis using either the anti-FLAG antibody or the antibody generated to the unique sCRFR2α C-terminus.

Bacterial expression of sCRFR2α: A cDNA corresponding to amino acids 20-143 was generated by PCR using mCRFR2α as the template. The cDNA was subcloned into pET-32a(+) (Novagen, La Jolla, Calif.) and the protein purified by S-protein affinity chromatography as described (Perrin et al., 2001). The protein was detected by immunoblot analysis using the antibody generated to the unique sCRFR2α C-terminus.

Radioreceptor assays. The soluble protein, purified either from COS M6 cell media or *E. coli* was incubated in triplicate wells with [$^{125}$I-DTyr$^O$]-astressin and increasing concentration of unlabeled peptides as described (Perrin et al., 2003).

B. Results

A cDNA transcript of smaller (~100 bp) size was observed during the isolation of the mouse CRFR2α (Van Pett et al., 2000). This smaller fragment was isolated and found to encode a variant of CRFR2α bearing a deletion of exon six. Translation of the variant transcript predicts a novel 143 amino acid protein, sCRFR2α, comprising the majority of the first extracellular domain of CRFR2α followed by a unique 38 amino acid C terminus (FIG. 1A). Screening of GenBank showed homology of the C-terminus to no other protein. The genomic arrangement of the sCRFR2α is shown in FIG. 1B.

Figure 2:
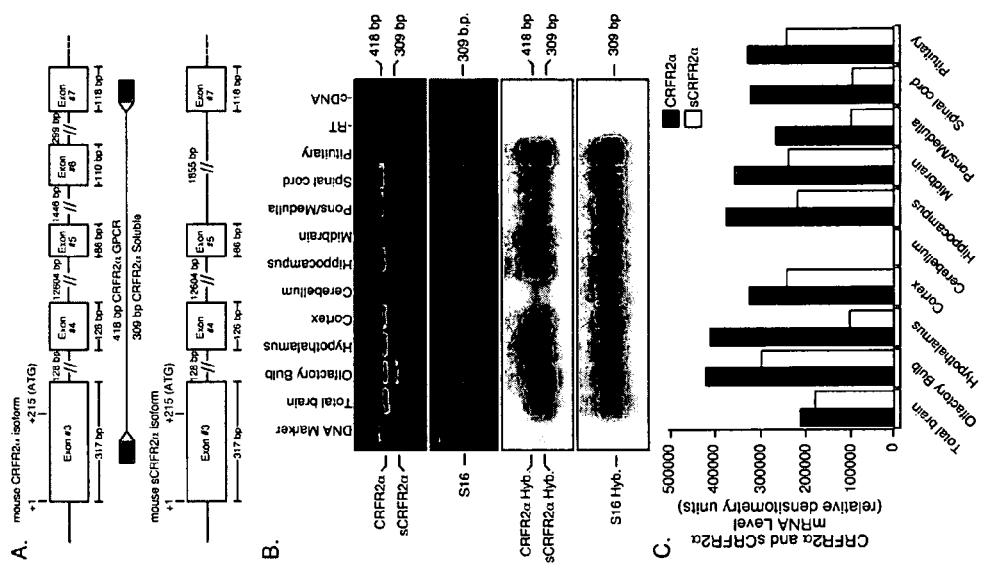
FIGS. 2A-2C. Show expression of CRFR2α and sCRFR2α mRNA in mouse brain and pituitary.

If the sCRFR2α mRNA is merely a product of splicing errors, it should be much less abundant than the correctly spliced RNA. In order to examine this question, semi-quantitative RT-PCR followed by Southern hybridization analysis was used to compare the relative abundance of CRFR2α and sCRFR2α mRNA in several brain regions. Total RNA prepared from mouse tissues was reverse-transcribed to generate cDNAs that were used as templates for semi-quantitative RT-PCR analysis, followed by Southern hybridization, using specific primers and probes for CRFR2α and sCRFR2α (FIG. 2). The oligonucleotide primer pair (located in exons three and seven) allowed the simultaneous amplification of both the soluble form and the full-length membrane bound receptor in a single reaction (FIG. 2A). The sCRFR2α is highly expressed in the olfactory, cortex, midbrain and the pituitary (FIGS. 2B and 2C). Lower levels of expression were found in the hippocampus, hypothalamus, pons, medulla and spinal cord (FIGS. 2B and 2C). As shown in FIG. 2, the abundance of sCRFR2α mRNA is lower, but comparable, to that of CRFR2α mRNA. The sequences of cDNA fragments from RT-PCR were found to encode a splice variant of the mouse CRFR2α gene (FIG. 1A).

Figure 3:
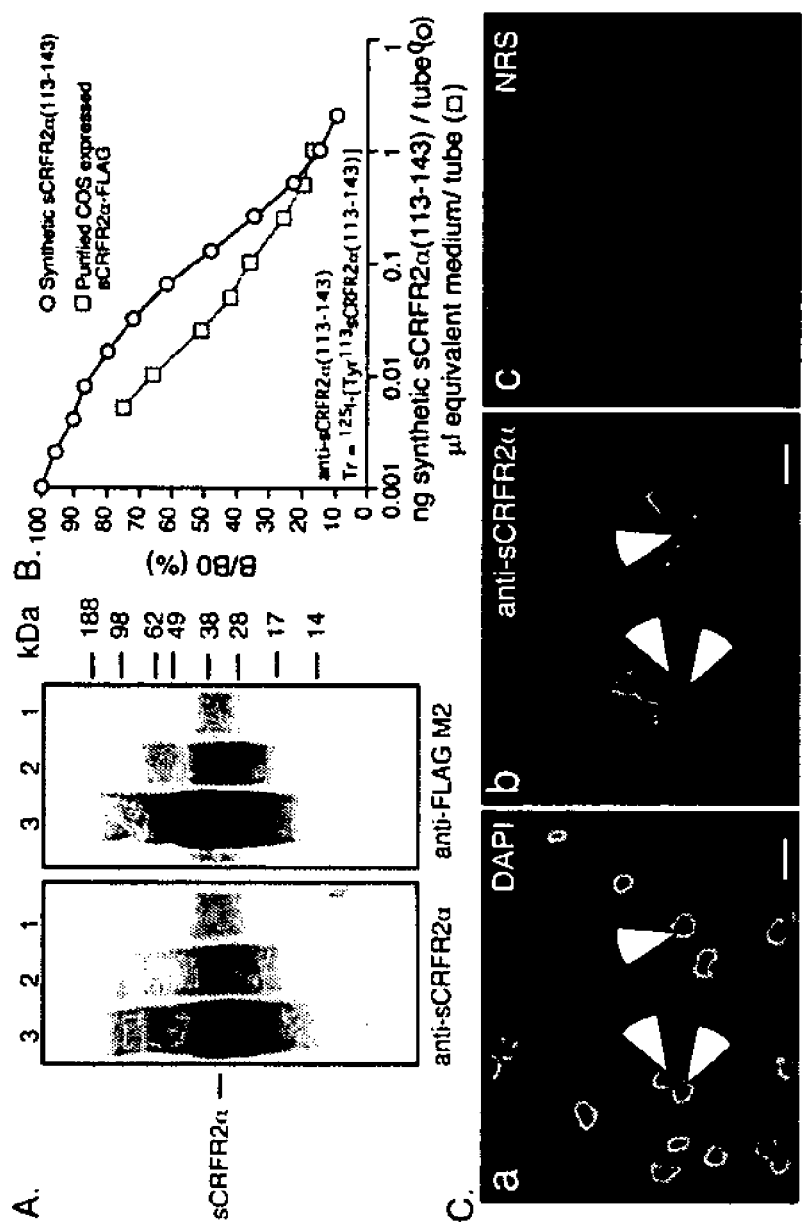
FIGS. 3A-3C. A highly specific antiserum raised in rabbit using a synthetic peptide fragment encoding the unique C-terminal tail of mouse sCRFR2α protein (aa 113-143) was used to develop a sCRFR2α radioimmunoassay, used for immunoblot analysis and for immunocytochemistry.

Computer analysis of the sequence predicted that the first 19 amino acids serve as a putative signal peptide. Because the sequence contains no obvious sites for membrane attachment, the protein is hypothesized to be secreted as a soluble form. To explore this hypothesis, the protein was expressed in COS M6 cells. Following purification from the media, a protein band of ~30 kD was visualized by immunoblot analyses using either anti-FLAG antiserum or the anti-sCRFR2α, an antiserum raised against a synthetic peptide fragment encoding the unique C-terminal tail of sCRFR2α protein (aa 113-143) (FIG. 3A). The larger size of the protein compared to that predicted from the cDNA is probably a result of glycosylation.

In order to obtain a larger quantity of sCRFR2α, a protein lacking the putative signal peptide was expressed as a fusion protein in E. coli (Perrin et al., 2001). Following cleavage and purification, the protein was visualized (using the anti-sCRFR2α) by immunoblot analysis as a narrow band of size ~20 kD. The anti-sCRFR2α serum detects the sCRFR2α proteins both in radioimmunoassay (FIG. 3B) as well as in immonocytochemistry (FIG. 3C).

Immunohistochemical studies using anti-sCRFR2α serum revealed the distribution of sCRFR2α-ir in rodent brain. The cellular distribution of immunolabeling for sCRFR2α-ir was widespread and conformed more closely to the location of CRFR1 mRNA expression pattern than to that of CRFR2 (FIGS. 4A-4F). The results described are from studies in mice; a similar pattern of labeling was observed in rats. Major sites of cellular expression include mitral and tufted cells of the olfactory bulb, the medial septavdiagonal band complex, piriform cortex, substantia nigra, red nucleus, basolateral amygdaloid, deep cerebellar and dorsal column nuclei, all of which are prominent sites of CRFR1 expression. Similar to CRFR1, sCRFR2α-ir cell bodies are numerous throughout isocortex, although the laminar distributions are only partly overlapping. Thus, while both CRFR1- and sCRFR2α-expressing cell bodies are numerous in layer 2/3, the dominant cortical seat of CRFR1 expression is in layer 4, while that of sCRFR2α is in layer 5. Major sites of CRFR2 expression, including the lateral septal, midbrain raphe, ventromedial hypothalamic and medial amygdaloid nuclei were all lacking in sCRFR2α-stained cell bodies, although interestingly the latter two sites were among the few invested with labeled varicosities that the inventors take to be representative of sCRFR2α-ir terminal fields. The paraventricular nucleus of the hypothalamus also contained a presumed sCRFR2α-ir terminal field of moderate density.

Labeling throughout the brain was blocked by pre-incubation of the antiserum with low micromolar concentrations ($\geq$30 µM) of the sCRFR2α (113-143) peptide used as immunogen; competition with the corresponding peptide predicted from the CRFR1 sequence did not interfere with immunolabeling at concentrations as high as 3 mM. Further support for the specificity of labeling are observations that all immunolocalizations persisted in CRFR1- and/or CRFR2-deleted mice; note that the targeting construct used for generating each of the existing receptor-knockout lines would be expected to spare the sCRFR2α coding region (Smith et al., 1998; Timpl et al., 1998; Bale et al., 2000).

Figure 4:
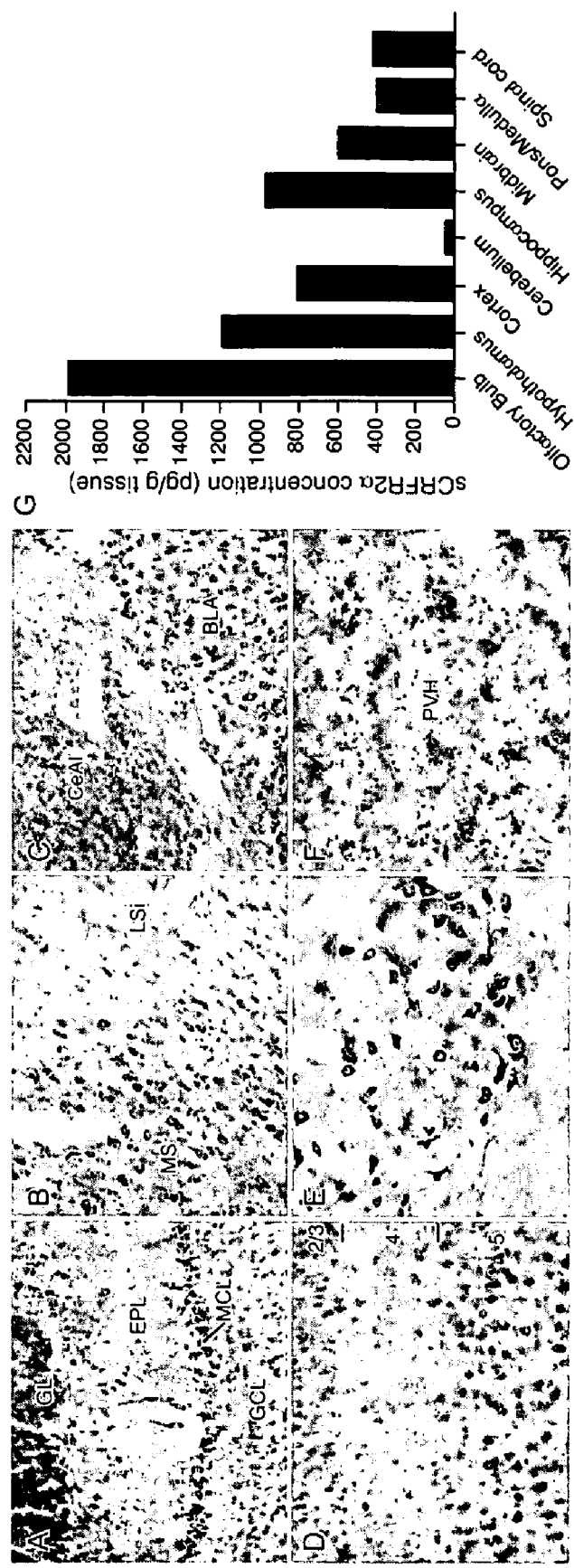
FIGS. 4A-4G. Illustrates the presence of sCRFR2α-like immunoreactivity (ir) in the mouse brain using immunohistochemistry and radioimmunoassay (RIA).

In order to determine the presence of sCRFR2α-like ir in brain, a highly specific radioimmunoassay was developed using anti-sCRFR2α-and [$^{125}$I-Tyr$^{113}$] sCRFR2α (113-143)] as the tracer. Tissue from mouse brain was acid-extracted, partially purified on C18 cartridges and assayed at multiple doses in the radioimmunoassay. The tissue extracts displaced [$^{125}$I-Tyr$^{113}$] sCRFR2α (113-143)] bound to anti-sCRFR2α in a dose-dependent manner (FIG. 4G). Highest levels of expression were found in the olfactory bulb, hypothalamus, cortex and midbrain, all of which correlate with the presence of ir cells and fibers, determined by the immunohistochemical studies (FIG. 4). A putative soluble form of CRFR1 (generated by deletion of exon 5) would comprise a different unique C-terminal sequence. A protein corresponding to that sequence did not displace [$^{125}$I-Tyr$^{113}$] sCRFR2α(113-143) in the radioimmunoassay. These results further confirm the existence of sCRFR2α protein in rodent CNS.

The interactions of the sCRFR2α with CRF family ligands were assessed by radioreceptor assay using competitive displacement of [$^{125}$I-D Tyr$^0$]-astressin bound to sCRFR2α. The soluble proteins, secreted by COS M6 cells or produced in bacteria, bind the agonists, Ucn 1 and CRF, as well as the antagonist, astressin, with nanomolar affinities, whereas, the affinities for Ucn 2 and Ucn 3 are much lower (Table 2).

TABLE 2

Inhibitory binding constants, Ki (nM) for CRF ligands binding to sCRFR2αproteins.

| Protein | CRF | rUcn1 | mUcn2 | mUcn3 | Astressin |
|---|---|---|---|---|---|
| mam sCRFR2α | 23 (14-39) | 6.6 (3.5-12) | 113 (68-190) | >200 | 6.7 (3.6-12) |
| bact sCRFR2α | 14.8 (9.2-24) | 5.8 (2.5-13.3) | 116 (85-158) | >200 | 10 (7.9-12.5) |

Binding of CRF family members to sCRFR2αproteins purified from either COS M6 cell media (mam sCRFR2α) or E. coli (bactsCRFR2α). See Methods for details.

Figure 5:
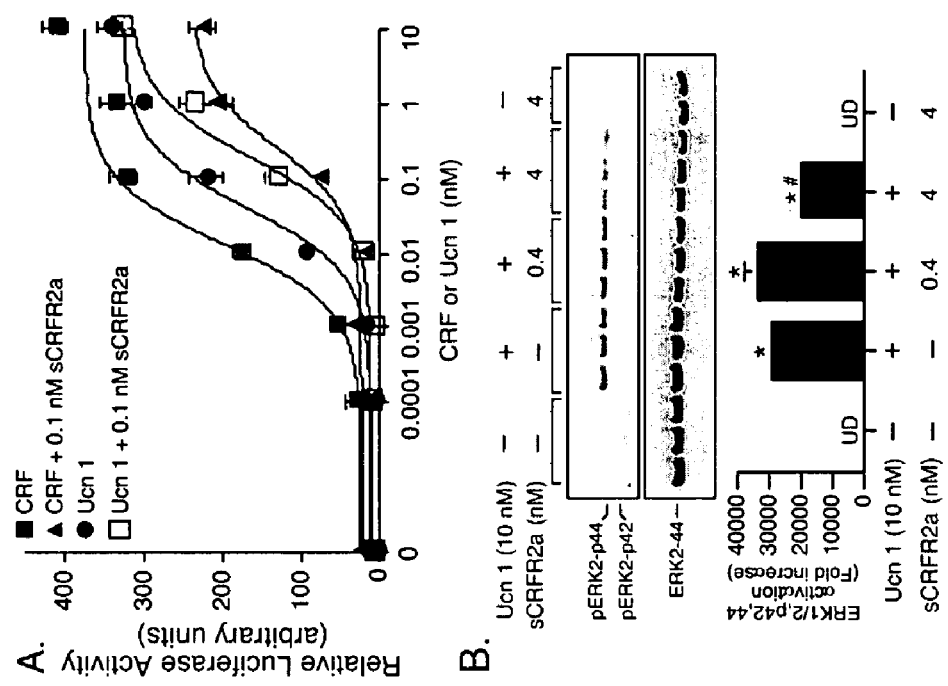
FIGS. 5A-5B. sCRFR2α protein interferes with the induction of cAMP and MAPK signaling mediated by Ucn 1 or CRF.

To delineate the possible functions of sCRFR2α, the inventors studied its effects on signaling by CRF family ligands. Both the mammalian and bacterially expressed sCRFR2α proteins inhibit, in a dose dependent manner, the cAMP response to Ucn 1 and CRF in HEK293T cells transfected with mouse CRFR2α as measured by the CRE luciferase activity of the EVX1 gene (FIG. 5A). Because the urocortins activate MAPK signaling (Brar et al., 2002), the inventors measured the ability of sCRFR2α to inhibit the activation by Ucn 1 of ERK1/2-p42,44 in CATH.a cells, which endogenously express CRFR1 and CRFR2α. The sCRFR2α inhibits the induction of phosphorylated ERK by Ucn 1 in CATH.a cells (FIG. 5B).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

The references listed below are incorporated herein by reference to the extent that they supplement, explain, provide a background for, or teach methodology, techniques, and/or compositions employed herein.

U.S. Pat. No. 4,196,265
U.S. Pat. No. 4,215,051
U.S. Pat. No. 4,554,101
U.S. Pat. No. 4,683,195
U.S. Pat. No. 4,683,202
U.S. Pat. No. 4,800,159
U.S. Pat. No. 4,883,750
U.S. Pat. No. 5,795,587
U.S. Pat. No. 5,063,245
U.S. Pat. No. 5,145,684
U.S. Pat. No. 5,225,538
U.S. Pat. No. 5,552,157
U.S. Pat. No. 5,565,213
U.S. Pat. No. 5,567,434
U.S. Pat. No. 5,580,579
U.S. Pat. No. 5,641,515
U.S. Pat. No. 5,738,868
U.S. Pat. No. 5,741,516
U.S. Pat. No. 5,792,451,
U.S. Pat. No. 6,831,158
Allen and Choun, *FEBS Lett.*, 223:42-46, 1987.
Andresz et al., *Makromol. Chem,* 179: 301, 1978
Avis, Remington's Pharmaceutical Sciences, 18th Ed., Gennaro (Ed.), Mack Publishing Co., Pa., 84:1545-1569, 1990.
Baichwal and Sugden, In: *Gene Transfer,* Kucherlapati (Ed.), NY, Plenum Press, 117-148, 1986.
Bale and Vale, *Annu. Rev. Pharmacol. Toxicol.,* 44, 525-557, 2004.
Bale et al., *Nat. Genet.,* 24, 410-414, 2000.
Baud et al., *Genomics,* 26(2):334-344, 1995.
Bellus, *J. Macromol. Sci. Pure Appl. Chem.,* A31(1): 1355-1376, 1994.
Benet et al., In: *Goodman & Gilman's The Pharmacological Basis of Therapeutics,* Hardman et al. (Eds.), McGraw-Hill, NY, Chap. 1, 9th Ed., 1996.
Berger et al., *Annu. Rev. Immunol.,* 17:657-700, 1999.
Bittencourt et al., *J. Comp. Neurol.,* 415, 285-312, 1999.
Bittner et al., *Methods in Enzymol,* 153:516-544, 1987.
Block, Remington's Pharmaceutical Sciences, 18th Ed., Gennaro (Ed.), Mack Publishing Co., Pa., 87:1609-1614, 1990.
Brar et al., In: *Encyclopedia of Hormones & Related Cell Regulators,* Henry (Ed.), AN (Academic Press), 3:13-325, 2002.
Chalmers et al., *Trends Pharmacol. Sci.,* 17(4):166-172. 1996.
Chandran et al., *Indian J. Exp. Biol.,* 35(8):801-809, 1997.
Chang et al., *Neuron.,* 11, 1187-1195, 1993.
Chen and Okayama, *Mol. Cell Biol.,* 7(8):2745-2752, 1987.
Chen et al. *Mol. Endocrinol.,* 19:441-458, 2005.
Chen et al., *Proc. Natl. Acad. Sci. USA,* 90:8967-8971, 1993.
Colbere-Garapin et al., *J. Mol. Biol.,* 150:1-14, 1981.
Coupar et al., *Gene,* 68:1-10, 1988.
Couvreur et al., *FEBS Lett.,* 84(2):323-326, 1977.
Couvreur et al., *J. Pharm. Sci.,* 69(2): 199-202, 1980.
Couvreur, *Crit. Rev. Ther. Drug Carrier Syst.,* 5(1):1-20, 1988.
Dautzenberg et al., *J. Neuroendocrinol.,* 11(12):941-949, 1999.
Delgado et al., *Crit Rev Ther Drug Carrier Syst.,* 9(3-4):249-304, 1992.
Douglas et al., *Crit Rev Ther Drug Carrier Syst.,* 3(3):233-61, 1987.
Eason et al., *Transplantation,* 61(2):224-228, 1996.
Ettinger et al., *Cancer,* 41:1270, 1978.
Fechheimer, et al., *Proc Natl. Acad. Sci. USA,* 84:8463-8467, 1987.
Fraley et al., *Proc. Natl. Acad. Sci. USA,* 76:3348-3352, 1979.
Freifelder, In: *Physical Biochemistry Applications to Biochemistry and Molecular Biology,* 2nd Ed. Wm. Freeman and Co., NY, 1982.
Friedmann, *Science,* 244:1275-1281, 1989.
Gabizon and Papahadjopoulos, *Proc. Natl. Acad. Sci. USA,* 85(18):6949-6953, 1988.
GB Appln. 2 202 328
Ghosh and Bachhawat, In: *Liver Diseases, Targeted Diagnosis and Therapy Using Specific Receptors and Ligands,* Wu et al. (Eds.), Marcel Dekker, NY, 87-104, 1991.
Goding, In: *Monoclonal Antibodies: Principles and Practice,* 2d ed., Academic Press, Orlando, Fla., pp 60-61, 71-74, 1986.
Gopal, *Mol. Cell Biol.,* 5:1188-1190, 1985.
Graham and Van Der Eb, *Virology,* 52:456-467, 1973.
Grammatopoulos et al., *Mol. Endocrinol.,* 13:2189-2202, 1999.
Graves et al., *Biochem. Biophys. Res. Commun.,* 187: 1135-1143, 1992.
Hamann et al., *J. Immunol.,* 155(4):1942-1950, 1995.
Harlow and Lane, In: *Antibodies: A Laboratory Manual,* Cold Spring Harbor Laboratory, Cold Spring Harbor, N.Y., 346-348, 1988.
Harvey, Remington's Pharmaceutical Sciences, 18th Ed., Gennaro Ed.), Mack Publishing Co., Pa., 35:711, 1990.
Henry-Michelland et al., *Int J Pharm,* 35: 121-7, 1987.
Hermonat and Muzycska, *Proc. Natl. Acad. Sci. USA,* 81:6466-6470, 1984.
Hess et al., *J. Adv. Enzyme Reg.,* 7:149, 1968.
Hitzeman et al., *J. Biol. Chem.,* 255:2073, 1980.
Holland et al., *Biochemistry,* 17:4900, 1978.
Horwich et al. *J. Virol.,* 64:642-650, 1990.
Hsu and Hsueh, *Nat. Med.,* 7605-611, 2001.
Hwang et al., *Crit. Rev. Ther. Drug Carrier Syst.,* 15(3):243-284, 1998.
Innis, et al., In: *PCR Protocols. A guide to Methods and Application,* Academic Press, Inc. San Diego, 1990.
Jacobson et al., *J. Acquir. Immune. Defic. Syndr.,* 21(1):S34-41, 1999.

Ji et al., *Biochem. Biophys. Res. Commun.*, 247:414-419, 1998.
Jones, *Genetics*, 85: 12, 1977.
Kehne and Lombaert, *Curr. Drug Targets CNS Neurol. Disord.*, 1(5):467-493, 2002.
Kemeny et al., *Cancer*, 71:1964, 1993.
Kenakin, *Life Sci.*, 43(14):1095-1101, 1988.
Khan et al., *Biochem. Biophys. Res. Commun.*, 190:888-894, 1993.
Kingsman et al., *Gene*, 7:141, 1979.
Kishimoto et al., *Proc Natl. Acad. Sci. USA*, 92:1108-1112, 1995.
Klein et al., *Nature*, 327:70-73, 1987.
Koob and Heinrichs, *Brain Res.*, 848:141-152, 1999.
Kostich et al., *Mol. Endocrinol.*, 12:1077-1085, 1998.
Kwoh et al., *Proc. Natl. Acad. Sci. USA*, 86:1173, 1989.
Kyte and Doolittle, *J. Mol. Biol.*, 157(1):105-132, 1982.
Lasic, *Trends Biotechnol.*, 16(7):307-321, 1998.
Lewis et al., *Proc. Natl. Acad. Sci. USA*, 98:570-7575, 2001.
Lin et al., *Science*, 282(5390):943-946, 1998.
Liu et al., *J. Biol. Chem.*, 269:29220-29226, 1994.
Lovenberg et al., *Endocrinology*, 136:4139-4142, 1995.
Lovenberg et al., *Proc. Natl. Acad. Sci. USA*, 92:836-840, 1995.
Lowy et al., *Cell*, 22:817-823, 1980.
Luer and Hatton, In: *The Annals of Pharmacotherapy*, 27:912, 1993.
Malherbe et al., *Brain Res. Mol. Brain Res.*, 67:201-210, 1999.
Mannstadt et al., *Am. J. Physiol.*, 277(5 Pt 2):F665-675, 1999.
Marchese et al., *Trends Pharmacol Sci.*, 20(9):370-375., 1999.
Margalit, *Crit. Rev. Ther. Drug Carrier Syst.*, 12(2-3):233-261, 1995.
Mathiowitz et al., *Nature*, 386(6623):410-414, 1997.
Meij et al., *Mol. Cell Biochem.*, 157(1-2):31-38, 1996.
Morishita et al., *Proc. Natl. Acad. Sci. USA*, 90:8474, 1993.
Muglia et al., *Nature*, 373:427-432, 1995.
Mulligan et al., *Proc. Natl. Acad. Sci. USA*, 78:2072, 1981.
Murphy et al., *J. Virol.*, 74(17):7745-7754, 2000.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
O'Hare et al., *Proc. Natl. Acad. Sci. USA*, 78: 1527, 1981.
Owens et al., *J. Pharmacol. Exp. Ther.*, 258(1):349-356, 1991.
Palczewski et al., *Science*, 289(5480):739-745, 2000.
PCT Appln. PCT Application WO 88/10315
PCT Appln. PCT/US87/00880
PCT Appln. PCT/US89/01025
PCT Appln. WO 00/23114
PCT Appln. WO 92/16655
Perrin and Vale, *Ann. N. Y. Acad. Sci.*, 885:312-328, 1999.
Perrin et al., *J. Biol. Chem.*, 276:31528-31534, 2001.
Perrin et al., *J. Biol. Chem.*, 278:15595-15600, 2003.
Perrin et al., *Proc. Natl. Acad. Sci. USA*, 92:2969-2973, 1995.
Pinto-alphandary et al., *J. Drug Target*, 3(2):167-169, 1995.
Pisarchik and Slominski, *Eur. J. Biochem.*, 2'71:2821-2830, 2004.
Potter et al., *Proc. Natl. Acad Sci. USA*, 81:7161-7165, 1984.
Quintanar-Guerrero et al., *Pharm. Res.*, 15(7):1056-1062, 1998.
Rekasi et al., *Proc. Natl. Acad, Sci. USA*, 97:0561-10566, 2000.
Remington's Pharmaceutical Sciences, 15$^{th}$ ed., pages 1035-1038 and 1570-1580, Mack Publishing Company, Easton, Pa., 1980.
Reyes et al., *Proc. Natl. Acad, Sci. USA*, 98:2843-2848, 2001.
Ridgeway, In: *Vectors: A survey of molecular cloning vectors and their uses*, Stoneham: Butterworth, pp. 467-492, 1988.
Rippe, et al., *Mol. Cell Biol.*, 10:689-695, 1990.
Rivier and Vale, *Nature*, 305:325-327, 1983.
Sambrook et al., In: *Molecular cloning: a laboratory manual*, 2$^{nd}$ Ed., Cold Spring Harbor Laboratory Press, Cold Spring Harbor, N.Y., 1989.
Schwarz et al., *J. Biol. Chem.*, 275:32174-32181, 2000.
Seck et al., *J. Biol. Chem.*, 278:23085-23093, 2003.
Shaw, *Cancer*, 72(11):3416, 1993.
Smith et al., *Neuron.*, 20:1093-1102, 1998.
Stacey et al., *Trends Biochem. Sci.*, 25(6):284-289, 2000.
Stenzel et al., *Mol. Endocrinol.*, 9:637-645, 1995.
Stinchcomb et al., *Nature*, 282(5734):39-43, 1979.
Szybalska et al., *Proc. Natl. Acad. Sci. USA*, 48:2026, 1962.
Takakura, *Nippon Rinsho.*, 56(3):691-695, 1998.
Temin, In: *Gene Transfer*, Kucherlapati (Ed.), NY, Plenum Press, 149-188, 1986.
Timpl et al., *Nat. Genet.*, 19:162-166, 1998.
Tschemper et al., *Gene*, 10: 157, 1980.
Tur-Kaspa et al., *Mol. Cell Biol.*, 6:716-718, 1986.
Vale et al., *Science*, 213:1394-1397, 1981.
Valerio et al., *Neuroreport*, 12:2711-2715, 2001.
van Dullemen et al., *Gastroenterology*, 109, 129-35, 1995.
VanPett et al., *J. Comp. Neurol.*, 428:191-212, 2000.
Vaughan et al., *Methods Enzymol.*, 168:588-617, 1989.
Vaughan et al., *Nature*, 378:287-292, 1995.
Vita et al., *FEBS Lett.*, 335:1-5, 1993.
Walker et al., *Proc. Natl. Acad. Sci. USA*, 89:392-396, 1992.
Wigler et al., *Cell*, 11(1):223-232, 1977.
Wigler et al., *Proc. Natl. Acad. Sci. USA*, 77(6):3567-3570, 1980.
Wilson et al., *Br. J. Pharmacol.*, 125(7):1387-1392, 1998.
Wilson et al., In: *G-protein-coupled receptors*, CRC press, Boca Raton, 97-116, 1999.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Yaida et al., *Regul. Pept.*, 59:193, 1995.
Yan and Wold, *Biochemistry*, 23(16):3759-3765.1984.
Yang and Russell, *Proc. Natl. Acad. Sci. USA*, 87:4144-4148, 1990.
You et al., *Biol. Reprod.*, 62:108-116, 2000.
Zambaux et al., *J. Control Release*, 50(1-3):31-40, 1998.
Zhu et al., *Brain Res. Mol. Brain Res.*, 73:3-103, 1999.
Zimm et al., *Cancer Research*, 44:1698, 1984.
zur Muhlen et al., *Eur. J. Pharm. Biopharm.*, 45(2):149-155, 1998.

What is claimed is:

1. An isolated, soluble corticotropin releasing factor receptor type 2 (sCRFR2) comprising an amino acid sequence that is at least 98% identical to the amino acid sequence of SEQ ID NO:4, wherein the sCRFR2 binds a corticotropin releasing factor receptor type 2 (CRFR2) ligand.

2. The sCRFR2 of claim 1, wherein the isolated sCRFR2 is attached to an affinity tag.

3. The sCRFR2 of claim 1, wherein the isolated sCRFR2 is attached to a fluorescent marker.

4. The sCRFR2 of claim 1, wherein the isolated sCRFR2 is attached to an immunoglobulin domain.

5. The sCRFR2 of claim 4, wherein the immunoglobulin domain comprises an immunoglobulin Fc domain.

6. The sCRFR2 of claim 1, further comprising a leader sequence.

7. The sCRFR2 of claim 1, wherein the sCRFR2 is conjugated to a polymer.

8. The sCRFR2 of claim 7 wherein the polymer is polyethylene glycol (PEG).

9. The sCRFR2 of claim 1 comprised in a pharmaceutically acceptable carrier.

10. The sCRFR2 of claim 1, wherein the sCRFR2 comprises the amino acid sequence of SEQ ID NO:4.

11. The sCRFR2 of claim 10, wherein the isolated sCRFR2 is attached to an affinity tag.

12. The sCRFR2 of claim 10, wherein the isolated sCRFR2 is attached to a fluorescent marker.

13. The sCRFR2 of claim 10, wherein the isolated sCRFR2 is attached to an immunoglobulin domain.

14. The sCRFR2 of claim 13, wherein the immunoglobulin domain is an immunoglobulin Fc domain.

15. The sCRFR2 of claim 10, further comprising a leader sequence.

16. The sCRFR2 of claim 10, wherein the sCRFR2 is conjugated to a polymer.

17. The sCRFR2 of claim 16 wherein the polymer is polyethylene glycol (PEG).

18. The sCRFR2 of claim 10 comprised in a pharmaceutically acceptable carrier.

19. A method of decreasing activity of a corticotropin releasing factor receptor (CRFR) comprising administering an effective dose of a sCRFR2 of claim 1 to a subject in need thereof, wherein binding of a CRFR ligand to a cell surface CRFR is reduced.

20. The method of claim 19, where the ligand is corticotropin releasing factor (CRF), urocortin 1, urocortin 2, urocortin 3, or stresscopin.

21. A method of decreasing activity of a corticotropin releasing factor receptor (CRFR) comprising administering an effective dose of a sCRFR2 of claim 10 to a subject in need thereof, wherein binding of a CRFR ligand to a cell surface CRFR is reduced.

22. The method of claim 21, where the ligand is corticotropin releasing factor (CRF), urocortin 1, urocortin 2, urocortin 3, or stresscopin.

* * * * *

UNITED STATES PATENT AND TRADEMARK OFFICE
CERTIFICATE OF CORRECTION

PATENT NO. : 7,507,794 B2  Page 1 of 1
APPLICATION NO. : 11/350411
DATED : March 24, 2009
INVENTOR(S) : Alon Chen et al.

It is certified that error appears in the above-identified patent and that said Letters Patent is hereby corrected as shown below:

In column 1, lines 8-10, delete
"The United States Government owns rights in present invention pursuant to grant number DK 26741 from the NIDDK." and insert
--This invention was made with government support under grant number DK 26741 awarded by The National Institute of Diabetes and Digestive and Kidney Diseases (NIDDK). The government has certain rights in the invention.-- therefor.

Signed and Sealed this

Twenty-sixth Day of May, 2009

JOHN DOLL
*Acting Director of the United States Patent and Trademark Office*